United States Patent
Blanc et al.

(10) Patent No.: US 6,833,382 B2
(45) Date of Patent: Dec. 21, 2004

(54) STREPTOGRAMINS AND METHOD FOR PREPARING SAME BY MUTASYNTHESIS

(75) Inventors: Véronique Blanc, Paris (FR); Denis Thibaut, Paris (FR); Nathalie Bamas-Jacques, Paris (FR); Francis Blanche, Paris (FR); Joël Crouzet, Sceaux (FR); Jean-Claude Barriere, Bures-sur-Yvette (FR); Laurent Debussche, Athis-Mons (FR); Alain Famechon, Janville-sur-Juine (FR); Jean-Marc Paris, Vaires-sur-Marne (FR); Gilles Dutruc-Rosset, Paris (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/987,614

(22) Filed: Nov. 15, 2001

(65) Prior Publication Data

US 2002/0142947 A1 Oct. 3, 2002

Related U.S. Application Data

(62) Division of application No. 08/765,907, filed as application No. PCT/FR95/00889 on Jul. 4, 1995, now Pat. No. 6,352,839.

(30) Foreign Application Priority Data

Jul. 8, 1994 (FR) .............................. 94 08478

(51) Int. Cl.[7] .................. A61K 31/40; C07D 213/02
(52) U.S. Cl. ..................... 514/410; 546/194
(58) Field of Search ......................... 546/194; 514/410

(56) References Cited

U.S. PATENT DOCUMENTS 4,082,736 A * 4/1978 Jones et al. ................. 536/53
4,156,734 A   5/1979 Stone
5,891,695 A   4/1999 Blanc et al.

FOREIGN PATENT DOCUMENTS

| EP | 133 196 | 3/1985 |
|----|---------|--------|
| WO | WO 93/20182 | 11/1993 |
| WO | WO 94/08014 | 4/1994 |

OTHER PUBLICATIONS

Anteunis, Marc J.O., et al., "Solution Conformation of Virginiamycins (Staphylomycins)," *Eur. J. Biochem.* 58: 259–268 (1975).

Breslow, Ronald, et al., "Artificial Transaminases Linking Pyridoxamine to Binding Cavities: Controlling the Geometry," *J. Amer. Chem. Soc.*, 112(13): 5212–19 (1990).

Craik, Charles S., "Use of Oligonucleotides for Site–Directed Mutagenesis," *Biotechniques*, pp. 12–19 (Jan./Feb. 1985).

International Search Report for PCT/FR95/00889.

Sadakane, Noriaki, et al., "Hybrid Biosynthesis of Derivatives of Protylonolide and M–4365 by Macrolide–Producing Microorganisms," *J. Antibiotics* 35(5): 680–687 (1982).

Zeller, E. Albert, et al., "Ophidian L–Amino Acid Oxidases," *Helvet. Chim. Acta*, 57(8): 2406–20 (1974).

* cited by examiner

*Primary Examiner*—Joseph K. McKane
*Assistant Examiner*—Binta Robinson

(57) ABSTRACT

Novel group B streptogramin-like compounds of general formula (I), and a method for preparing streptogramines by mutasynthesis using a mutated micro-organism to influence the biosynthesis of at least one of the precursors of group B streptogramins are disclosed. Novel nucleotide sequences involved in the biosynthesis of said precursors, and their uses, are also disclosed.

27 Claims, 15 Drawing Sheets

Figure 1:
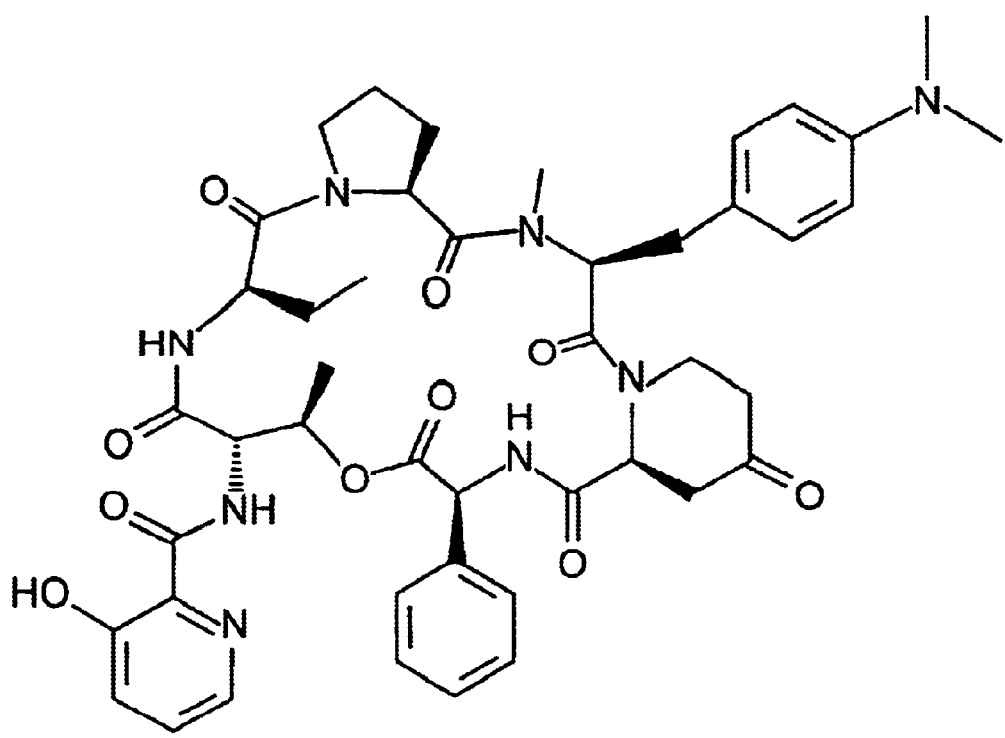

$R_1=H, R_2=Me$    $PI_H$
$R_1=H, R_2=H$    $PI_I$ $PI_B$ = PRISTINAMYCIN $I_B$, VERNAMYCIN Bβ, OSTREOGRYCIN $B_2$
$PI_C$ = PRISTINAMYCIN $I_C$, VERNAMYCIN Bγ, OSTREOGRYCIN $B_1$

ETAMYCIN A (neoviridogrisein IV, viridogrisein)

$R_1$=OH(cis), $R_2$=Me

NEOVIRIDOGRISEIN I, $R_1$=H, $R_2$=Et, $R_3$=Me
II, $R_1$=H, $R_2$=Me, $R_3$=Me
III, $R_1$=OH, $R_2$=Et, $R_3$=Me
Cl-c, $R_1$=Cl (cis), $R_2$=Me, $R_3$=Me
Cl-t, $R_1$=Cl (trans), $R_2$=Me, $R_3$=Me VIRIDOGRISEIN II, $R_1$=OH, $R_2$=Et, $R_3$=H

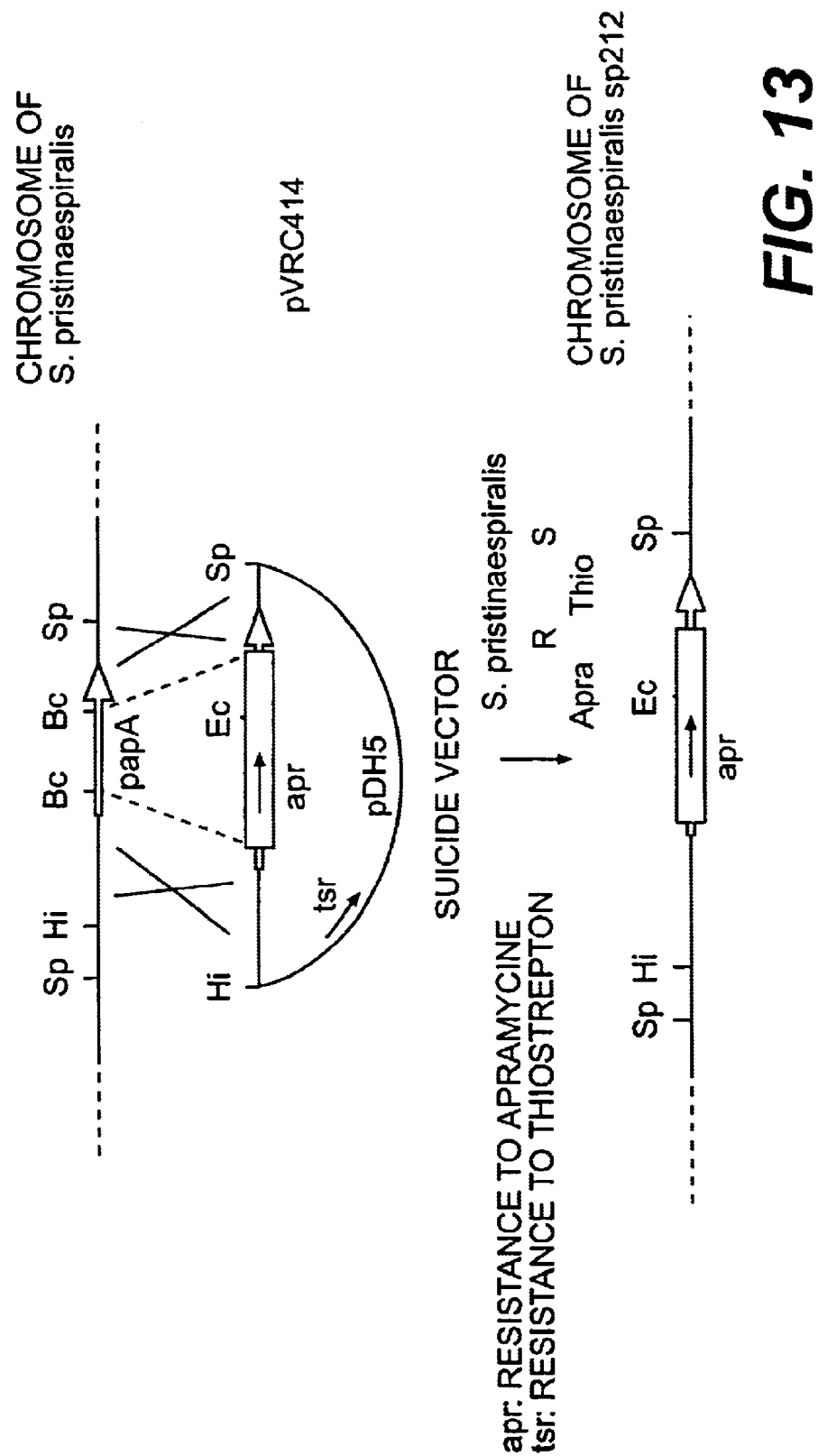

STREPTOGRAMINS AND METHOD FOR PREPARING SAME BY MUTASYNTHESIS

This application is a DIV of Ser. No. 08/765,907 filed Mar. 20, 1997, now U.S. Pat. No. 6,352,839, which is a 371 of PCT/FR95/00889 filed Jul. 4, 1995.

The present invention relates principally to novel compounds which are related to the group B streptogramins, and to a process for preparing streptogramins by mutasynthesis. It also relates to novel genes which are involved in the biosynthesis of precursors of the group B streptogramins, and to their uses.

The streptogramins form a homogeneous group of antibiotics consisting of an association of two types of chemically different molecules; on the one hand polyunsaturated macrolactones (group A components) and, on the other hand, depsipeptides (group B components). This group comprises numerous antibiotics which are known under different names according to their origin and includes pristinamycins, mikamycins and virginiamycins (Cocito 1979, 1983).

The A and B components have a synergistic antibacterial activity which can amount to 100 times that of the separate components and which, contrary to that of each component, is bactericidal (Cocito 1979). This activity is more particularly effective against Grai-positive bacteria such as *Staphylococci* and *Streptococci* (Cocito 1979, Videau 1982). Components A and B inhibit protein synthesis by binding to the 50S subunit of the ribosome (Cocito 1979; Di Giambattista et al., 1989).

While knowledge of the routes by which each of the components is biosynthesized still remains partial to date, earlier studies, presented in Patent Application PCT/FR93/0923, have made it possible to identify several proteins, and the corresponding structural genes, which are involved in the biosynthesis of the two types of component.

Two parts can be distinguished in the process for biosynthesizing group B streptogramins:

1) Biosynthesis of the precursors, or their analogues, of the macrocycle: 3-hydropicolinic acid, L-2-aminobutyric acid, 4-dimethylamino-L-phenylalanine, L-pipecolic acid and L-phenylglycine.

2) Formation of the macrocycle from the precursors listed above, from L-threonine and from L-proline, or their analogues, with (a) possible subsequent modification(s) of the peptide N-methylation, epimerisation, hydroxylation and oxidation type.

Patent Application PCT/FR93/0923 relates, in particular, to the enzymes which catalyze incorporation of the precursors into the peptide chain of B streptogramins in the process of elongation, and also to their structural genes. These results have demonstrated the non-ribosomal peptide synthesis character of the type B components.

Figure 2:
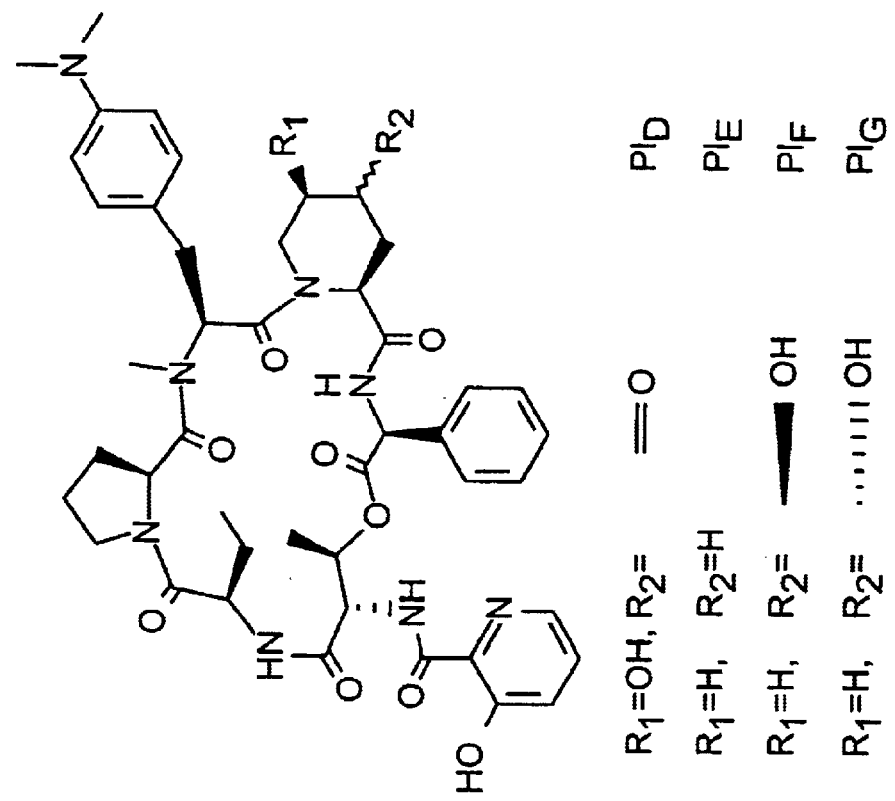
Figure 2:
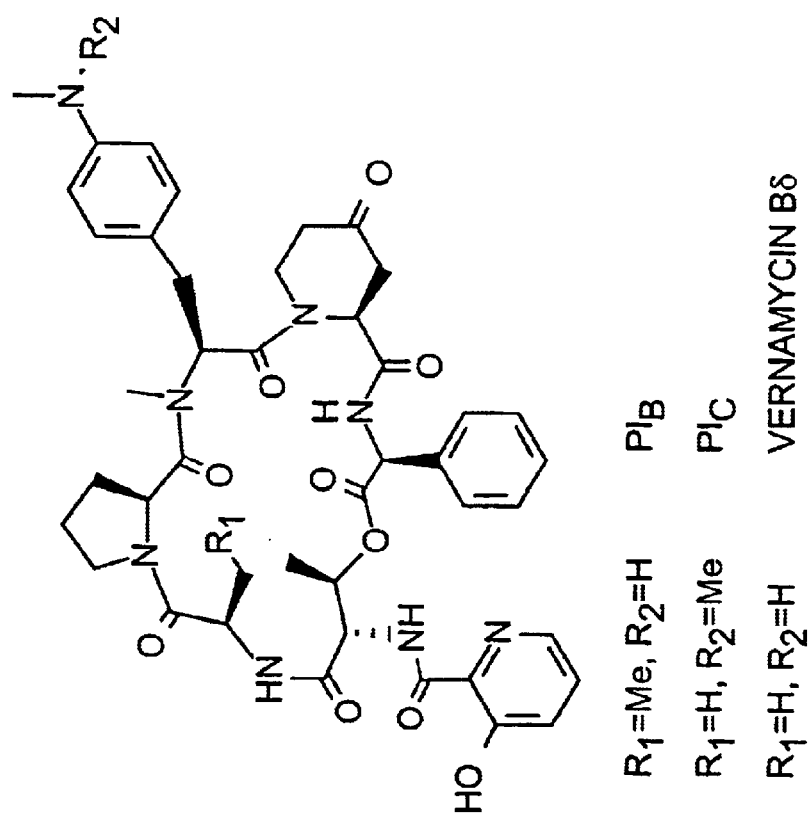
Figure 2:
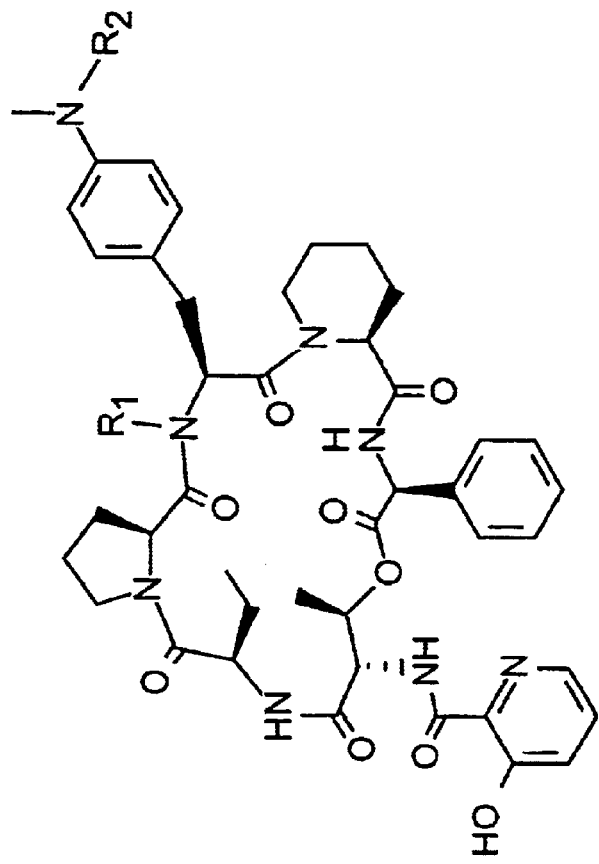
Figure 2:
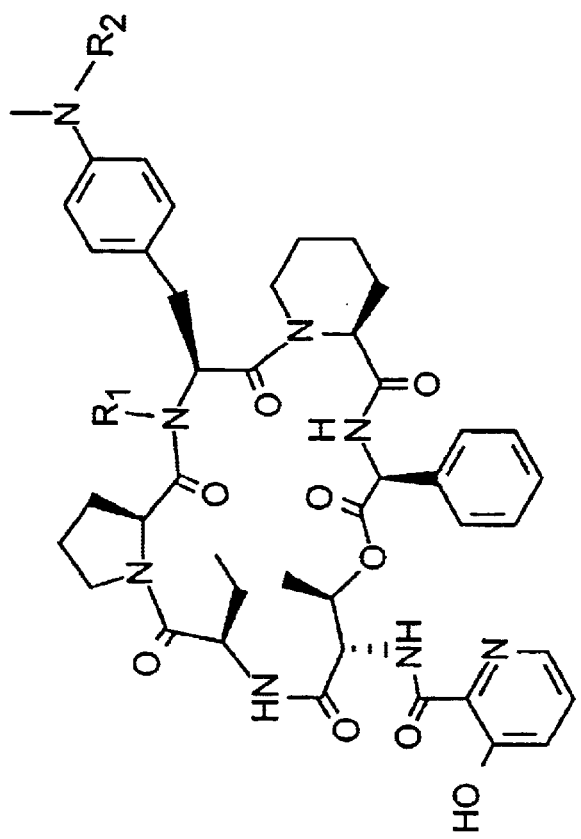
Figure 3:
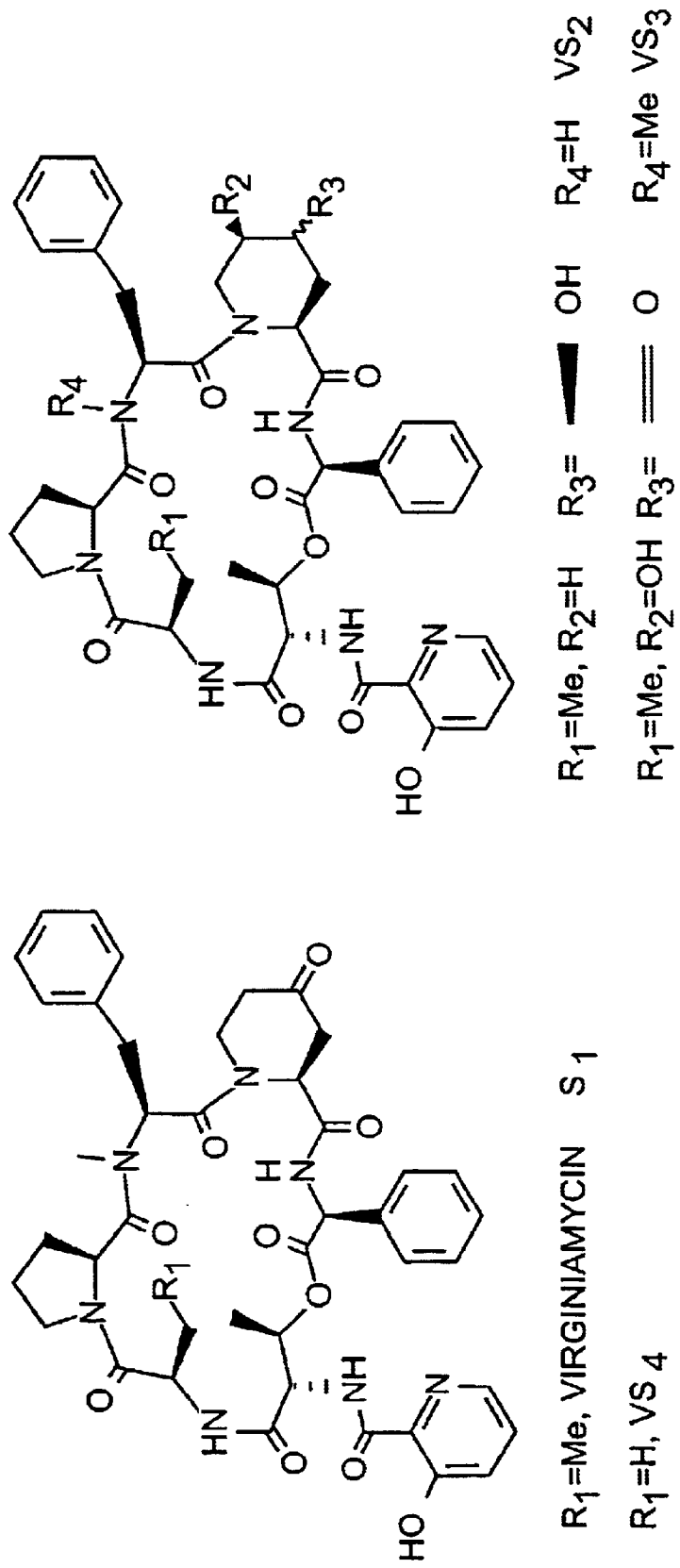
Figure 3:
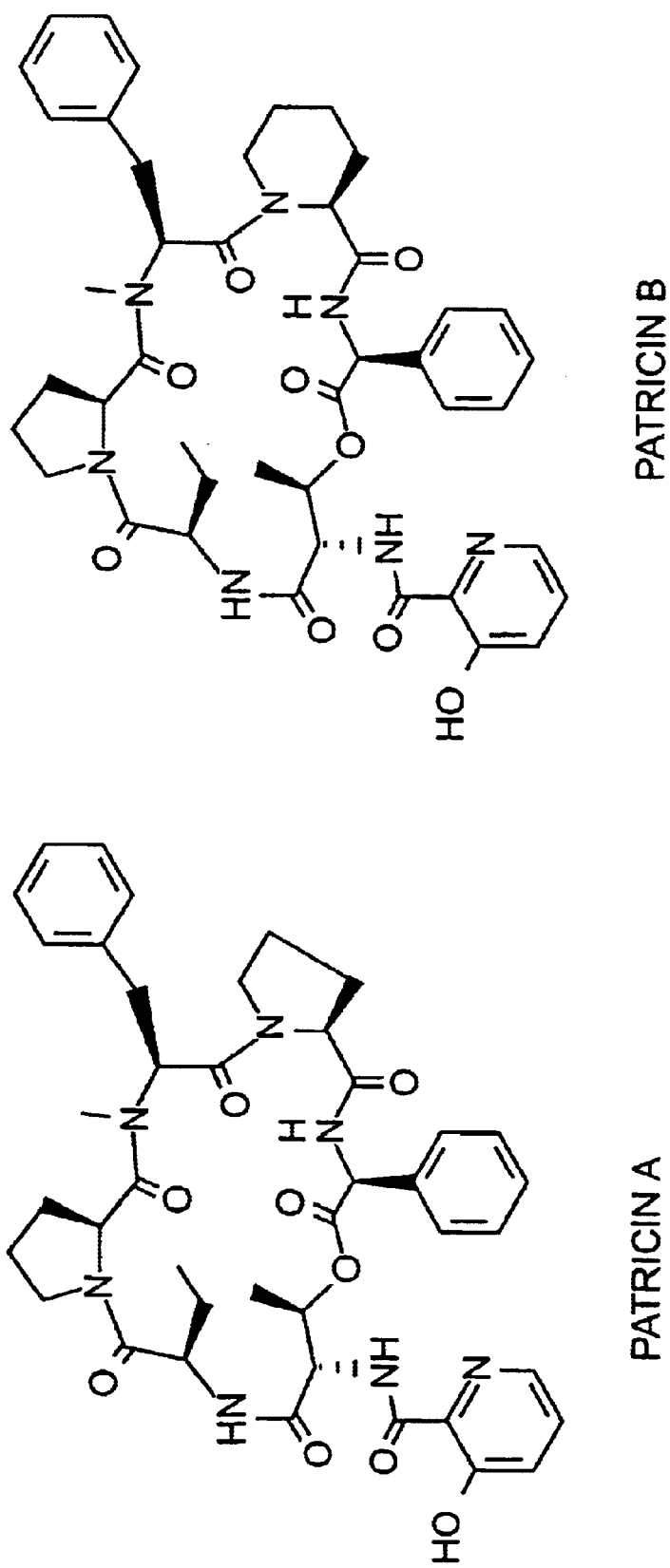
Figure 3:
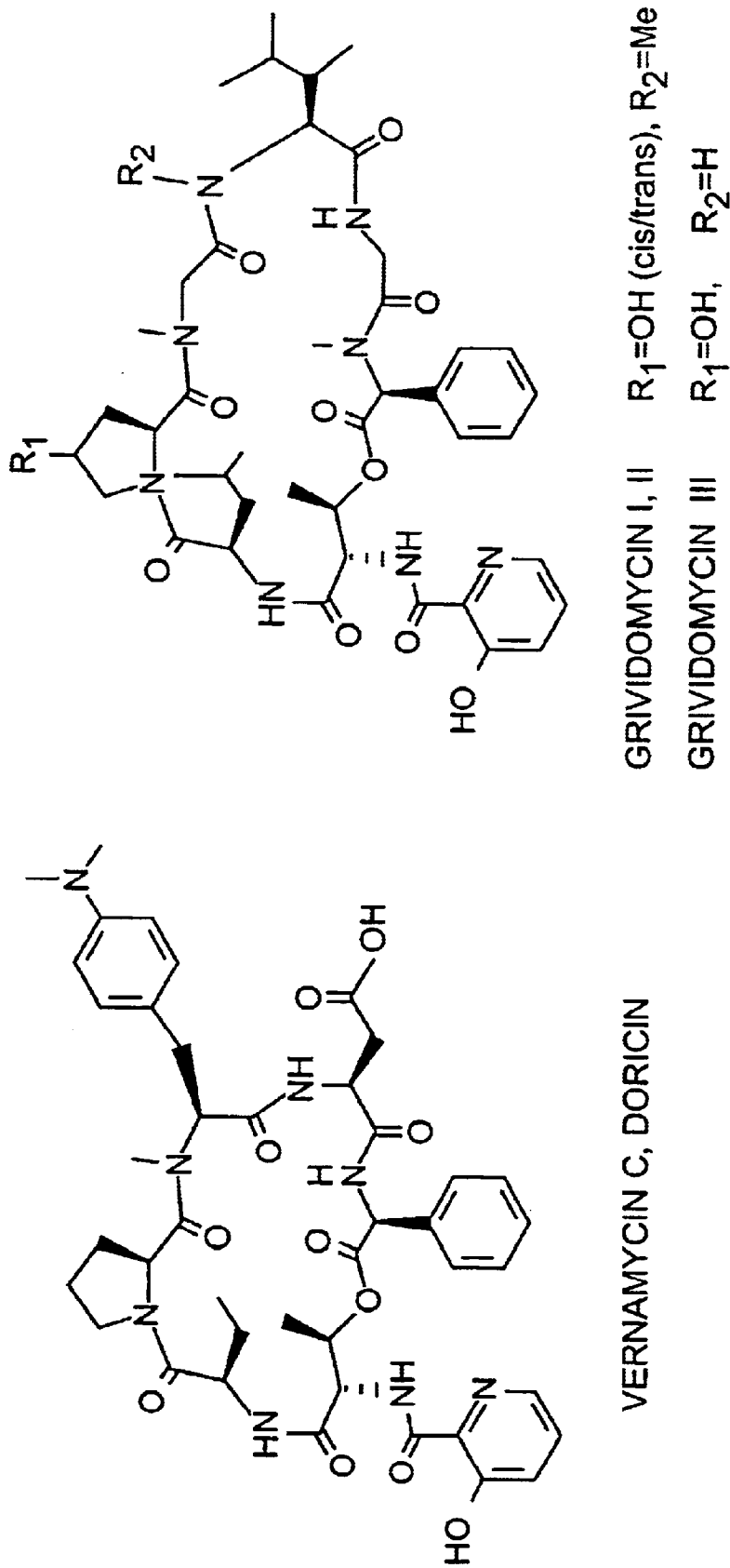
Figure 3:
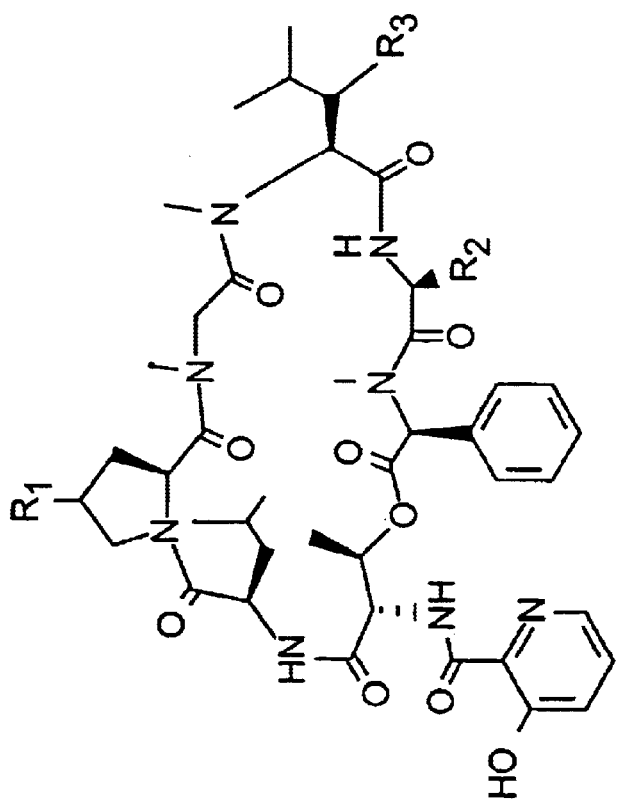

The present invention relates, more particularly, to novel compounds which are related to group B streptogramins and, more precisely, to novel compounds of the pristinamycin I family (FIGS. 1 and 2), termed PI below, or of the virginiamycin S family (FIG. 3).

The major constituent of the I pristinamycins (PI) is $PI_A$ (FIG. 1), which represents approximately 94% of the PI, with the remaining approximately 6% being represented by minor constituents of the depsipeptide ($PI_B$, to $PI_I$) whose structures are depicted in FIG. 2. PI results essentially from the condensation of amino acids, certain of which are essential for protein synthesis (threonine and proline) and others of which are novel and themselves considered to be secondary metabolites (L-2-aminobutyric acid, 4-dimethylamino-L-phenylalanine (DMPAPA), L-pipecolic acid and L-phenylglycine for $PI_A$), and also of an aromatic precursor, 3-hydroxypicolinic acid.

The virginiamycin S derivatives result from condensation of the same acids as in the case of PI, apart from 4-DMPAPA, which is replaced by a phenylalanine (see FIG. 3).

Production of these different compounds by biosynthesis therefore requires preliminary synthesis, by a producer strain, of the novel precursors identified above.

The present invention results specifically from a novel process for preparing streptogramins which employs, as a strain for producing streptogramins, a microorganism strain which is mutated so as to alter the biosynthesis of the precursors of the group B streptogramins. According to this process, the said mutant strain is cultured in a medium which is supplemented with a novel precursor which is different from the precursor whose biosynthesis is altered. Unexpectedly, this results in the production of novel compounds which are related to the group B streptogramins and which are of value in the therapeutic sphere.

More precisely, the present invention relates to novel compounds which are represented by the general formula I:

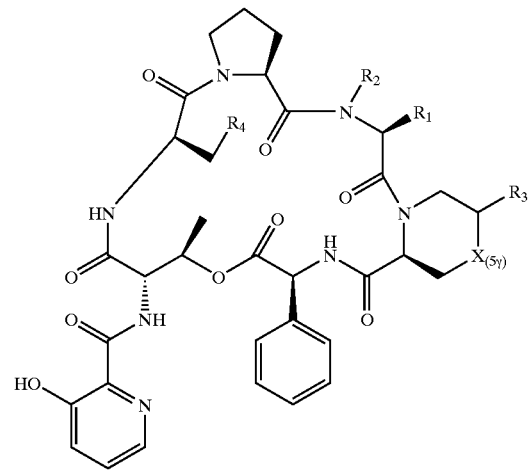

in which:
$R_2$ and $R_4$ represent, independently of each other, a hydrogen atom or a methyl group,
$R_3$ represents a hydrogen atom or a hydroxyl group,
X represents a CO, CHOH or $CH_2$ group, and
$R_1$ represents:

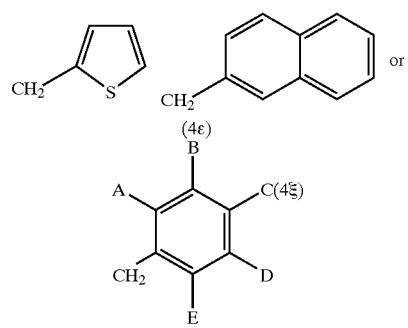

with
for the meta derivatives:
A, C, D and E representing a hydrogen atom, and

B being able to represent
  a halogen, and preferably a fluorine atom,
  a monoalkylamino or dialkylamino group, with alkyl preferably representing a methyl or ethyl group,
  an ether group; more particularly an OR group with R being preferably selected from among the methyl, ethyl, trifluoromethyl and allyl groups,
  a thioether group, preferably represented by an alkylthio group with alkyl preferably representing a methyl group,
  a $C_1$ to $C_3$ alkyl group, or
  a trihalogenomethyl group, preferably trifluoromethyl
for the para derivatives
  A, B, D and E representing a hydrogen atom, and C being able to represent:
    a halogen,
    an $NR_1R_2$ group with $R_1$ and $R_2$ representing, independently of each other, a group selected from among
      hydrogen,
      a straight-chain or branched $C_1$ to $C_4$ alkyl group where, when one of the substituents $R_1$ or $R_2$ represents a methyl group, the other necessarily represents an ethyl group,
      an alkyl-cycloalkylmethyl group with a $C_3$ to $C_4$ cycloalkyl,
      an optionally substituted $C_3$ to $C_4$ cycloalkyl group,
      a straight-chain or branched $C_1$ to $C_4$ alkenyl group where, when one of the substituents $R_1$ or $R_2$ represents an alkenyl group, the other is different from a methyl group or a $C_3$ to $C_6$ cycloalkyl,
    a substituted or unsubstituted N-pyrrolidinyl group,
    an ether group; preferably an OR group with R preferably being selected from among the methyl and ethyl groups, where appropriate substituted by a chlorine atom, or trifluoromethyl and alkenyl groups
    a thioether group, preferably represented by an alkylthio group with alkyl preferably representing a $C_1$ to $C_3$ alkyl group,
    an acyl or alkoxycarbonyl group and, more particularly, a COR group with R preferably representing a $C_1$ to $C_3$ alkyl group or a $C_1$ to $C_3$ alkoxy group,
    a $C_1$ to $C_6$ alkyl group which is straight-chain or branched and which is preferably selected from among the methyl, isopropyl and tert-butyl groups,
    an alkylthiomethyl group and, more preferably, a $CH_2SR$ group with R preferably representing a $C_1$ to $C_3$ alkyl group,
    an aryl group, preferably a phenyl group, or
    a trihalogenomethyl group, preferably trifluoromethyl
for the meta-para disubstituted derivatives:
  A, D and E representing a hydrogen atom, and
  B being able to represent:
    a halogen, preferably a fluorine atom,
    a monoalkylamino or dialkylamino group with alkyl preferably representing a methyl or ethyl group,
    an ether group and preferably an OR group with R preferably selected from among the methyl, ethyl and trifluoromethyl groups,
    a thioether group and preferably alkylthio with alkyl preferably representing an ethyl group, or
    a $C_1$ to $C_3$ alkyl group, and
  C being able to represent:
    a halogen, preferably a fluorine atom,
    an amino, monoalkylamino or dialkylamino group with alkyl preferably representing a methyl group with the proviso that B is different from a bromine or chlorine atom, or a substituted or unsubstituted allyl group,
    an ether group and preferably an OR group with R preferably selected from among the methyl, ethyl and trifluoromethyl groups,
    a thioether group and preferably an alkylthio group with alkyl preferably representing a methyl group,
    a $C_1$ to $C_6$ alkyl group, or
    a trihalogenomethyl group, preferably trifluoromethyl, and
for the ortho-para disubstituted derivatives:
  B, E and D representing a hydrogen atom and A and C a methyl group.

The following may be more particularly mentioned as preferred compounds:

4ζ-methylthio-de(4ζ-dimethylamino)pristinamycin $I_A$,
4ζ-methylthio-de(4ζ-dimethylamino)pristinamycin $I_H$,
5γ-hydroxy-4ζ-methylthio-de(4ζ-dimethylamino)pristinamycin $I_H$,
4ζ-methyl-de(4ζ-dimethylamino)pristinamycin $I_A$,
4ζ-methyl-de(4ζ-dimethylamino)pristinamycin $I_H$,
4ζ-methoxy-de(4ζ-dimethylamino)pristinamycin $I_A$,
4ζ-methoxycarbonyl-de(4ζ-dimethylamino)pristinamycin $I_A$,
4ζ-chloro-de(4ζ-dimethylamino)pristinamycin $I_A$,
4ζ-bromo-de(4ζ-dimethylamino)pristinamycin $I_A$,
4ζ-bromo-de(4ζ-dimethylamino)pristinamycin $I_H$,
4ζ-iodo-de(4ζ-dimethylamino)pristinamycin $I_A$,
4ζ-iodo-de(4ζ-dimethylamino)pristinamycin $I_H$,
4ζ-trifluoromethyl-de(4ζ-dimethylamino)pristinamycin $I_A$,
4ζ-trifluoromethyl-de(4ζ-dimethylamino)pristinamycin $I_H$,
4ζ-tert-butyl-de(4ζ-dimethylamino)pristinamycin $I_A$,
4ζ-isopropyl-de(4ζ-dimethylamino)pristinamycin $I_A$,
4ζ-isopropyl-de(4ζ-dimethylamino)pristinamycin $I_E$,
4ε-methylamino-de(4ζ-dimethylamino)pristinamycin $I_A$,
4ε-methoxy-de(4ζ-dimethylamino)pristinamycin $I_A$,
4ε-methoxy-de(4ζ-dimethylamino)pristinamycin $I_H$,
4ε-fluoro-4ζ-methyl-de(4ζ-dimethylamino)pristinamycin $I_A$,
4ζ-amino-de(4ζ-dimethylamino)pristinamycin $I_A$,
4ζ-ethylamino-de(4ζ-dimethylamino)pristinamycin $I_A$,
4ζ-diethylamino-de(4ζ-dimethylamino)pristinamycin $I_A$,
4ζ-allylamino-de(4ζ-dimethylamino)pristinamycin $I_A$,
4ζ-diallylamino-de(4ζ-dimethylamino)pristinamycin $I_A$,
4ζ-allylethylamino-de(4ζ-dimethylamino)pristinamycin $I_A$,
4ζ-ethylpropylamino-de(4ζ-dimethylamino)pristinamycin $I_A$,
4ζ-ethylisopropylamino-de(4ζ-dimethylamino)pristinamycin $I_A$,
4ζ-ethylmethylcyclopropylamino-de(4ζ-dimethylamino)pristinamycin $I_A$,
4ζ-(1-pyrrolidinyl)-de(4ζ-dimethylamino)pristinamycin $I_A$,
4ζ-trifluoromethoxy-de(4ζ-dimethylamino)pristinamycin $I_A$,
4ζ-allyloxy-de(4ζ-dimethylamino)pristinamycin $I_A$,
4ζ-ethoxy-de(4ζ-dimethylamino)pristinamycin $I_A$,
4ζ-ethylthio-de(4ζ-dimethylamino)pristinamycin $I_A$,
4ζ-methylthiomethyl-de(4ζ-dimethylamino)pristinamycin $I_A$,
4ζ-(2-chloroethoxy)-de(4ζ-dimethylamino)pristinamycin $I_A$,
4ζ-acetyl-de(4ζ-dimethylamino)pristinamycin $I_A$,
4ζ-ethyl-de(4ζ-dimethylamino)pristinamycin $I_A$,
4ζ-ethyl-de(4ζ-dimethylamino)pristinamycin $I_H$,
4ε-dimethylamino-de(4ζ-dimethylamino)pristinamycin $I_A$,
4ε-methylthio-de(4ζ-dimethylamino)pristinamycin $I_A$,
4ε-ethoxy-de(4ζ-dimethylamino)pristinamycin $I_A$.

The present invention is also directed towards a process which is particularly useful for preparing the compounds of the general formula I.

More precisely, it relates to a process for preparing streptogramins, characterized in that it employs a streptogramin-producing microorganism strain which possesses at least one genetic modification which affects the biosynthesis of a precursor of the group B streptogramins, and in that the said mutant strain is cultured in a culture medium which is appropriate and which is supplemented with at least one novel precursor which is different from that whose biosynthesis is altered, and in that the said streptogramins are recovered.

The strains which are employed within the scope of the present invention are therefore strains which produce streptogramins and which are mutated. The genetic modification(s) can be located either within one of the genes which is involved in the biosynthesis of the said precursors or outside the coding region, for example in the regions responsible for the expression and/or the transcriptional or post-transcriptional regulation of the said genes, or in a region belonging to the transcript containing the said genes.

According to one particular embodiment of the invention, the mutant strains possess one or more genetic modifications within at least one of their genes which is/are involved in the biosynthesis of the group B streptogramin precursors.

This or these genetic modification(s) alter(s) the expression of the said gene, that is render(s) this gene, and, as the case may be, another of the genes involved in the biosynthesis of the precursors, partially or totally incapable of encoding the natural enzyme which is involved in the biosynthesis of at least one precursor. The inability of the said genes to encode the natural proteins may be manifested either by the production of a protein which is inactive due to structural or conformational modifications, or by the absence of production, or by the production of a protein having an altered enzymatic activity, or else by the production of the natural protein at an attenuated level or in accordance with a desired mode of regulation. The totality of these possible manifestations is expressed by an alteration of, or perhaps a blockage in, the synthesis of at least one of the group B streptogramin precursors.

The genes which are capable of being mutated within the scope of the present invention are preferably the genes which are involved in the biosynthesis of the following precursors: L-2-aminobutyric acid, 4-dimethylamino-L-phenylalanine (DMPAPA), L-pipecolic acid, L-phenylglycine and/or 3-hydroxypicolinic acid (3-HPA).

These genes are more preferably the papA (SEQ ID NO: 14), papM (SEQ ID NO: 16), papB (SEQ ID NO: 4), papC (SEQ ID No. 2), hpaA (SEQ ID NO: 12), snbF (SEQ ID NO: 9), and pipA (SEQ ID NO: 7) genes described below.

The papA and papM genes have already been described in Patent Application PCT/FR93/0923. They are present on the cosmid pIBV2. The papA pap gene appears to correspond to a gene for biosynthesizing 4-amino-L-phenylalanine from chorismate. The 4-amino-L-phenylalanine is then dimethylated by the product of the papM gene, an N-methyltransferase, in order to form 4-dimethylamino-L-phenylalanine, DMPAPA, which is then incorporated into pristinamycin $I_A$. These two genes are more particularly involved, therefore, in the synthesis of the precursor termed DMPAPA.

Figure 7:
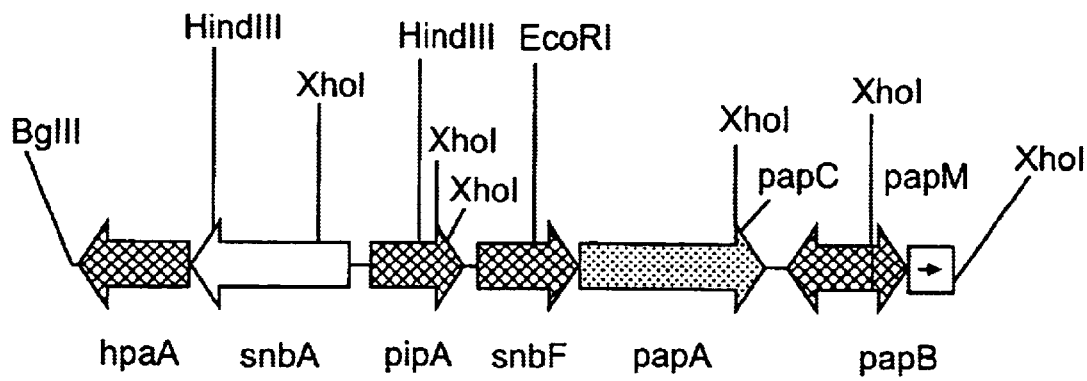

The other genes, papB, papC, pipA, snbF and hpaA, have been identified and characterized within the scope of the present invention. They are grouped together with the snbA, papA and papM genes on a chromosomal region of approximately 10 kb (FIG. 7).

The sequence homologies demonstrated for the PapB (SEQ ID NO: 5) and PapC (SEQ ID NO: 3) proteins show that these proteins are also involved, jointly with the PapA (SEQ ID NO: 15) and PapM (SEQ ID NO: 17) proteins, in the biosynthesis of the DMPAPA precursor. The two corresponding novel genes, papB and papC, were isolated and identified by subcloning which was carried out using cosmid pIBV2, described in Patent Application PCT/FR93/0923, and a plasmid, pVRC900, which is derived from pIBV2 by means of a HindIII deletion and is also described in Patent Application PCT/FR93/0923.

The comparison of the protein encoded by the papC gene with the protein sequences contained in the Genpro library shows a 27% homology with the region which is involved in the prephenate dehydrogenase activity of the bifunctional TyrA proteins of *E. coli* (Hudson and Davidson, 1984) and *Erwinia herbicola* (EMBL data library, 1991). This region of TyrA catalyses aromatization of the prephenate to form 4-hydroxyphenylpyruvate in the biosynthesis of tyrosine. A similar aromatization, which proceeds from 4-deoxy-4-aminoprephenate and leads to 4-aminophenyl-pyruvate is very probably involved in the synthesis of DMPAPA. It would be catalysed by the PapC protein (SEQ ID No. 2).

PapB possesses a 24 to 30% homology with the region which is involved in the chorismate mutase activity of the TyrA and PheA bifunctional proteins of *E. coli*, (Hudson and Davidson, 1984) and of the TyrA protein of *Erwinia herbicola*. This region catalyses isomerization of the chorismate to form prephenate in the biosynthesis of tyrosine and of phenylalanine. The PapB protein (SEQ ID No. 3) is probably involved in a similar isomerization which proceeds from 4-deoxy-4-aminochorismate and leads to 4-deoxy-4-aminoprephenate in the synthesis of DMPAPA.

The pipA, snbF and hpaA genes have been located in the regions which are contained between the snbA gene, which encodes 3-hydroxypicolinic acid AMP ligase and is described in Patent Application PCT/FR93/0923, and the papA or snbR genes. They were located accurately by means of subcloning, which was carried out using the plasmid pVRC900 and the cosmid pIBV2, which are described in Patent Application PCT/FR93/0923.

On comparing the protein encoded by the hpaA gene and the protein sequences contained in the Genpro library, a homology of from 30 to 40% was detected with a group of proteins which are probably involved (Thorson et al., 1993) in the transamination of intermediates in the biosynthesis of various antibiotics (DnrJ, EryCl, TylB, StrS and PrgL). Synthesis of the 3-HPA precursor, which appears to derive from lysine by another route than that of cyclodeamination (see examples 1-2 and 2-1), probably requires a transamination step which can be catalyzed by the product of this gene termed hpaA (SEQ ID NO: 12). Furthermore, the results of mutating this gene demonstrate unequivocally that it is involved in the synthesis of the 3-HPA precursor.

Comparison of the product encoded by the gene termed pipA with the protein sequences contained in the Genpro library shows a 30% homology with the ornithine cyclodeaminase of *Agrobacterium tumefaciens* (Schindler et al., 1989). This enzyme is involved in the final step of the catabolism of octopine; it converts L-ornithine into L-proline by means of cyclodeamination. Authors have demonstrated, by means of incorporating labelled lysine, that 4-oxopipecolic acid and 3-hydroxypicolinic acid, which are found both in $PI_A$ and in virginiamycin S1, derived from lysine (Molinero et al., 1989, Reed et al., 1989). Cyclodeamination of lysine, in a similar manner to that described for ornithine, would lead to the formation of pipecolic acid. Taking this hypothesis into account, this product was termed PipA (SEQ ID NO: 7). The results of mutating the pipA gene, presented in the examples below, demonstrate that it is involved solely in the synthesis of pipecolic acid. It is noted, in particular, that this mutation has no effect on the biosynthesis of 3-hydroxypicolinic acid, which is also derived from lysine and of which pipecolic acid could have been a precursor.

Finally, on comparing the product of the gene termed snbF with the protein sequences contained in the Genpro library, a 30 to 40% homology was noted with several hydroxylases of the cytochrome P450 type, which are involved in the biosynthesis of secondary metabolites (Omer et al., 1990; Trower et al., 1992). Several hydroxylations can be envisaged in the biosynthesis of the precursors of pristinamycin I, in particular in the biosynthesis of 3-HPA (hydroxylation of picolinic acid at the 3 position) and of 4-oxopipecolic acid (hydroxylation of pipecolic acid at the 4 position). The corresponding protein was termed SnbF (SEQ ID NO: 9).

The results of mutating the pipA gene, with polar effects on the expression of the snbF gene, demonstrate the involvement of the snbF gene in the hydroxylation of the pipecolic acid residue of group B streptogramins. The expression of the snbF gene is thus altered by the expedient of effecting a genetic modification of the pipA gene.

Preferentially, the genetic modification(s) render(s) the said gene partially or totally incapable of encoding the natural protein.

Genetic modification should be understood to mean, more particularly, any suppression, substitution, deletion, or addition of one or more bases in the gene(s) under consideration. Such modifications may be obtained in vitro (on the isolated DNA) or in situ, for example, by means of genetic engineering techniques, or else by exposing the said microorganisms to a treatment using mutagenic agents. Examples of mutagenic agents which may be cited are physical agents such as high energy rays (X, γ, ultraviolet, etc. rays), or chemical agents which are able to react with different functional groups of the DNA bases, and, for example, akylating agents [ethyl methanesulphonate (EMS), N-methyl-N'-nitro-N-nitrosoguanidine, and N-nitroquinoline-1-oxide (NQO)], bialkylating agents, intercalating agents, etc. Deletion is understood to mean any suppression of a part or all of the gene under consideration. This deletion can, in particular, be of a part of the region encoding the said proteins, and/or of all or part of the promoter region for transcription or translation, or else of the transcript.

The genetic modifications may also be obtained by means of gene disruption, for example using the protocol initially described by Rothstein [Meth. Enzymol. 101 (1983) 202] or, advantageously, by means of double homologous recombination. In this case, the integrity of the coding sequence will preferentially be disrupted in order to permit, if need be, replacement, by means of homologous recombination, of the wild-type genomic sequence with a non-functional or mutant sequence.

According to another option of the invention, the genetic modifications can consist of placing the gene(s) encoding the said proteins under the control of a regulated promoter.

The mutant microorganism strains according to the present invention may be obtained from any microorganism which produces streptogramins (cf. Table V). According to one particular embodiment of the invention, the mutant strain is a strain which is derived from S. pristinaespiralis and, more particularly, from S. pristinaespiralis SP92.

Mutant strains which are preferred within the scope of the present invention and which may more particularly be mentioned are the strain SP92::pVRC508, which is mutated in the biosynthesis of the DMPAPA precursor by disrupting the papA gene by means of simple crossing over, or else, more preferably, the strain SP212, which is mutated in the biosynthesis of the DMPAPA cursor by disrupting the papA gene by means of double homologous recombination. These strains no longer produce PI unless they are supplemented with the DMPAPA precursor. Unexpectedly, when a novel precursor, which is different from DMPAPA and which is capable, after, in this case, metabolization, of being incorporated by PI synthetase III (SnbD protein which is responsible for incorporating L-proline and DMPAPA residues) is added to the production medium, these two strains then become able to produce novel I pristinamycins or virginiamycins, or else mainly to produce a component which is normally a minor component of PI, in particular $PI_B$ (FIG. 2).

Two other mutant strains have been prepared within the scope of the present invention. These are, respectively, the strain SP92pipA::$\Omega am^R$, in which the pipA gene is disrupted by homologous recombination, and the strain SP92hpaA::$\Omega am^R$, in which the hpaA gene is disrupted. While strain SP92pipA::$\Omega am^R$ no longer produces PI under standard fermentation conditions it strongly produces, in the presence of L-pipecolic acid, a component, which was initially a minor component among the B streptogramin components, in which 4-oxopipecolic acid is replaced by L-pipecolic acid. While strain S. pristinaespiralis SP92hpaA::$\Omega am^R$ no longer produces PI under standard fermentation conditions, it is able to produce novel group B streptogramins in the presence of novel precursors.

By supplementing the medium for culturing mutant strains according to the invention with at least one novel precursor, it turns out that it is possible to orient biosynthesis either towards novel streptogramins, or towards a minor form of the streptogramins, or else to favour formation of one of the streptogramins.

The precursors which are employed within the scope of the present invention can be derivatives or analogues of amino acids and, more particularly of phenylalanine, as well as organic acids and, in particular, alpha-cetocarboxylic acids and, more particularly, derivatives of phenylpyruvic acid.

Naturally, the novel precursor is such that it complements the alteration or blockage, which is induced in accordance with the invention, within the biosynthesis of one of the natural precursors of the group B streptogramins and leads to the synthesis of streptogramins. According to one particular embodiment of the invention, this novel precursor is selected such that it is related to the precursor whose biosynthesis is altered. Thus, in the specific case of the mutant which is blocked in the biosynthesis of DMPAPA, the novel precursor is preferably a derivative of phenylalanine.

The following may, in particular, be cited as precursors which are suitable for the invention:

Phenylalanine, 4-dimethylaminophenylalanine, 4-methylaminophenylalanine, 4-aminophenylalanine, 4-diethylaminophenylalanine, 4-ethylaminophenylalanine, 4-methylthiophenylalanine, 4-methylphenylalanine, 4-methoxyphenylalanine, 4-trifluoromethoxyphenylalanine, 4-methoxycarbonylphenylalanine, 4-chlorophenylalanine, 4-bromophenylalanine, 4-iodophenylalanine, 4-trifluoromethylphenylalanine, 4-tert-butylphenylalanine, 4-isopropylphenylalanine, 3-methylaminophenylalanine, 3-methoxyphenylalanine, 3-methylthiophenylalanine, 3-fluoro-4-methylphenylalanine, L-pipecolic acid, 4-tert-butylphenylpyruvic acid, 4-methylaminophenylpyruvic acid, 2-naphthylphenylalanine, 4-fluorophenylalanine, 3-trifluorophenylalanine, 3-ethoxyphenylalanine, 2,4-dimethylphenylalanine, 3,4-dimethylphenylalanine, 3-methylphenylalanine, 4-phenylphenylalanine, 4-butylphenylalanine, 2-thienyl-3-alanine, 3-trifluoromethylphenylalanine, 3-hydroxyphenylalanine, 3-ethylaminophenylalanine, 4-allylaminophenylalanine, 4-diallylaminophenylalanine, 4-allylethylaminophenylalanine, 4-ethylpropylaminophenylalanine, 4-ethylisopropylaminophenylalanine, 4-ethylmethylcyclopropylaminophenylalanine, 4-(1-pyrrolidinyl)phenylalanine, 4-O-allyltyrosine, 4-O-ethyltyrosine, 4-ethylthiophenylalanine, 4-ethylthiomethylphenylalanine, 4-O-(2-chloroethyl)tyrosine, 4-acetylphenylalanine, 4-ethylphenylalanine, 3-dimethylaminophenylalanine, 3-ethoxyphenylalanine, 3-fluoro-4-methylphenylalanine and 4-aminomethylphenylalanine.

Among these precursors, 4-trifluoromethoxyphenylalanine, 3-methylaminophenylalanine, 3-methylthiophenylalanine, 3-fluoro-4-methylphenylalanine, 4-methylaminophenylpyruvic acid, 3-ethoxyphenylalanine, 4-allylaminophenylalanine, 4-diallylaminophenylalanine, 4-allylethylaminophenylalanine, 4-ethylpropylaminophenylalanine, 4-ethylisopropylaminophenylalanine, 4-ethylmethylcyclopropylaminophenylalanine, 4-(1-pyrrolidinyl)phenylalanine, 4-ethylthiomethylphenylalanine, 4-O-(2-chloroethyl)tyrosine, 3-dimethylaminophenylalanine and 3-ethylaminophenylalanine are novel and were prepared and characterized within the scope of the present invention. They are found to be particularly useful for preparing streptogramins according to the invention.

The claimed process turns out to be particularly adventageous for preparing novel group B streptogramins or else for favoring formation of particular streptogramins. As such, it is particularly useful for preparing $PI_B$.

The present invention also relates to a nucleotide sequence which is selected from among:

(a) all or part of the genes papC (SEQ ID No. 2), papB (SEQ ID NO: 4), pipA (SEQ ID NO: 7), snbF (SEQ ID NO: 9) and hpaA (SEQ ID NO: 12), (b) sequences which hybridize with all or part of the (a) genes, and (c) sequences which are derived from (a) and (b) sequences on account of the degeneracy of the genetic code.

In the particular case of the hybridizing sequences according to (b), these sequences preferably encode a polypeptide which is involved in the biosynthesis of the streptogramins.

Still more preferably, the invention relates to the nucleotide sequences which are represented by the genes papC (SEQ ID No. 2), papB (SEQ ID NO: 4), pipA (SEQ ID NO: 7), snbF (SEQ ID NO: 9), and hpaA (SEQ ID NO: 12).

The invention furthermore relates to any recombinant DNA which encompasses a papC (SEQ ID No. 2), papB (SEQ ID NO: 4), pipA (SEQ ID NO: 7), snbF (SEQ ID NO: 9) or hpaA (SEQ ID NO: 12) gene.

Naturally, the nucleotide sequences defined above can be part of a vector of the expression vector type, which can be an autonomously replicating vector, an integrated vector or a suicide vector. The present invention is also directed to these vectors as well as to any use of a sequence according to the invention or of a corresponding vector for, in particular, preparing metabolites of interest. It furthermore relates to any polypeptide which results from the expression of a claimed sequence.

The present invention also relates to any mutated *S. pristinaespiralis* strain which possesses at least one genetic modification within one of the papC (SEQ ID No. 2), papB (SEQ ID NO: 4), pipA (SEQ ID NO: 7), snbF (SEQ ID NO: 9) and hpaA (SEQ ID NO: 12) genes, and, more preferably, to strains SP92pipA::$\Omega am^R$ and SP92hpaA::$\Omega am^R$, as well as any *S. pristinaespiralis* strain, such as SP212, which possesses a genetic modification which consists of a disruption of the papA gene by means of double homologous recombination.

Combinations of a component of the group A streptogramins and of a compound of the general formula I, according to the invention, constitute compositions which are particularly advantageous in the therapeutic sphere. They are employed, in particular, for treating ailments which are due to Gram-positive bacteria (of the genera *Staphylococci, Streptococci, Pneumococci* and *Enterococci*) and Gram-negative bacteria (of the genera *Haemophilus, Gonococci, Meningococci*). Thus, the compounds according to the invention have a synergistic effect on the antibacterial action of pristinamycin IIB on *Staphylococcus aureus* IP8203 in mice in vivo, at oral doses which are principally between 30 mg/kg and 100 mg/kg, when they are combined in PI/PII proportions of the order of 30/70.

The present invention extends to any pharmaceutical composition which contains at least one compound of the general formula I which is or is not combined with a group A streptogramin.

The examples appearing below are presented by way of illustrating the present invention and do not limit it.

LIST OF FIGURES

FIG. 1: Structure of pristinamycin $I_A$.

FIG. 2: Structure of the minor components of pristinamycin I.

FIG. 3: Other examples of structures of B components of streptogramins.

Figure 4:
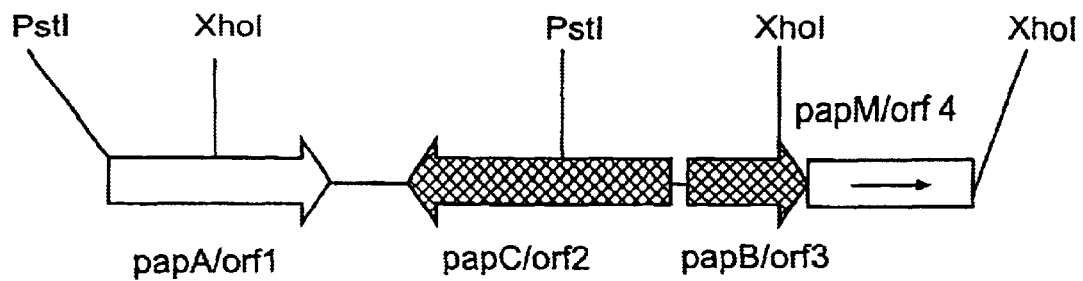

FIG. 4: Depiction of the PstI-XhoI region of 2.9 kb.

Figure 5:
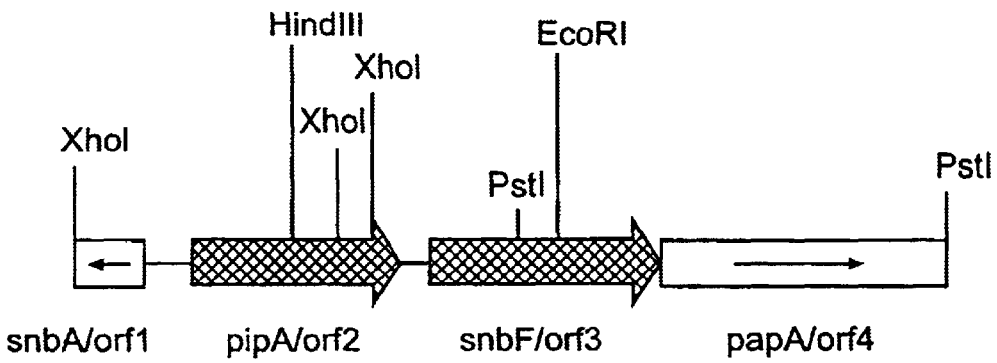

FIG. 5: Depiction of the XhoI-PstI region of 4.5 kb.

Figure 6:
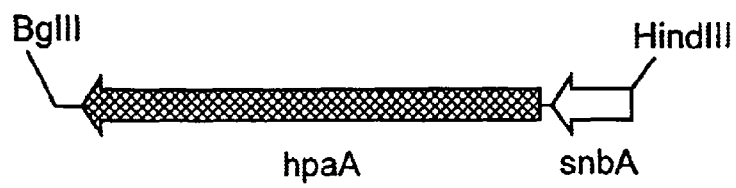

FIG. 6: Depiction of the HindIII-BglII region of 1.6 kb.

FIG. 7: Depiction of the BglII-XhoI region of approximately 10 kb.

Figure 8:
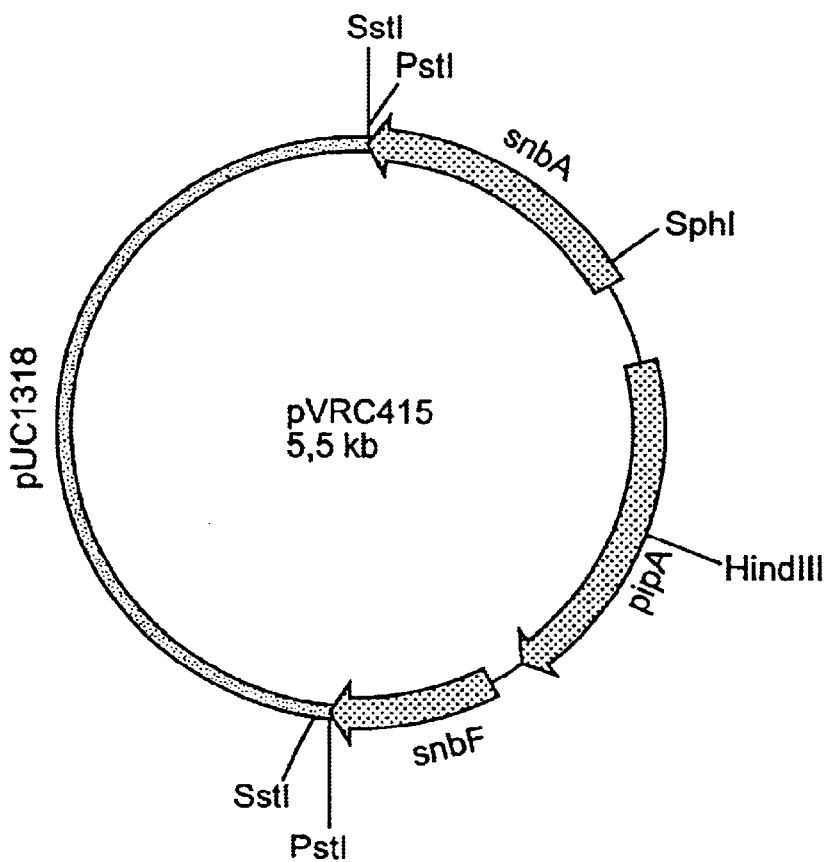

FIG. 8: Depiction of plasmid pVRC415.

Figure 9:
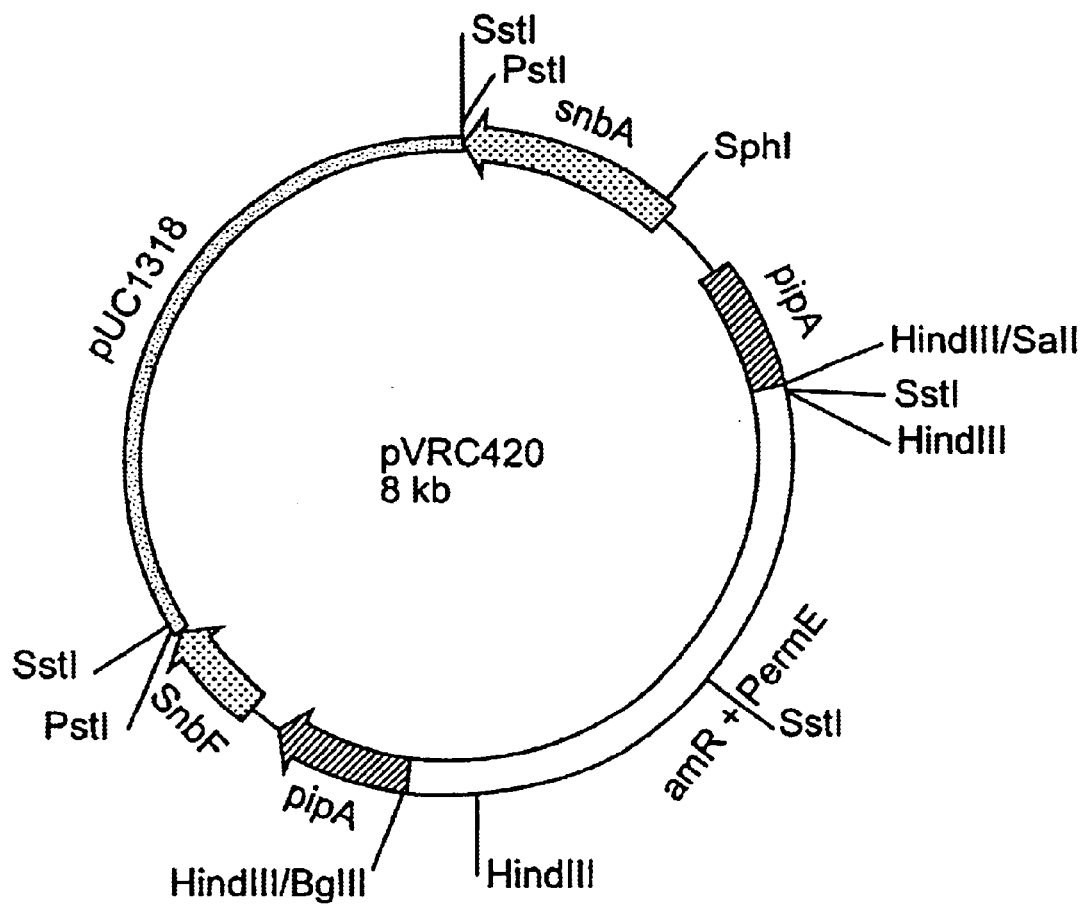

FIG. 9: Depiction of plasmid pVRC420.

Figure 10:
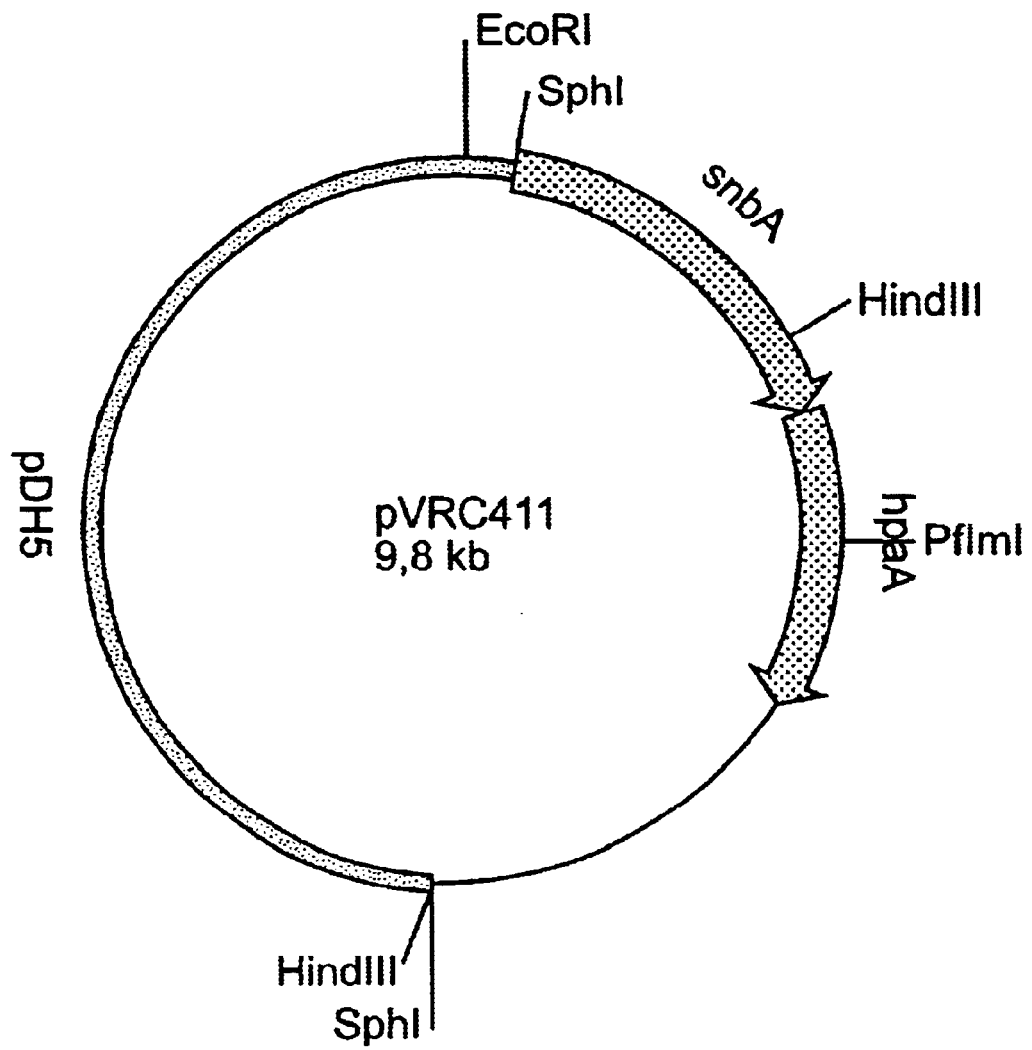

FIG. 10: Depiction of plasmid pVRC411.

Figure 11:
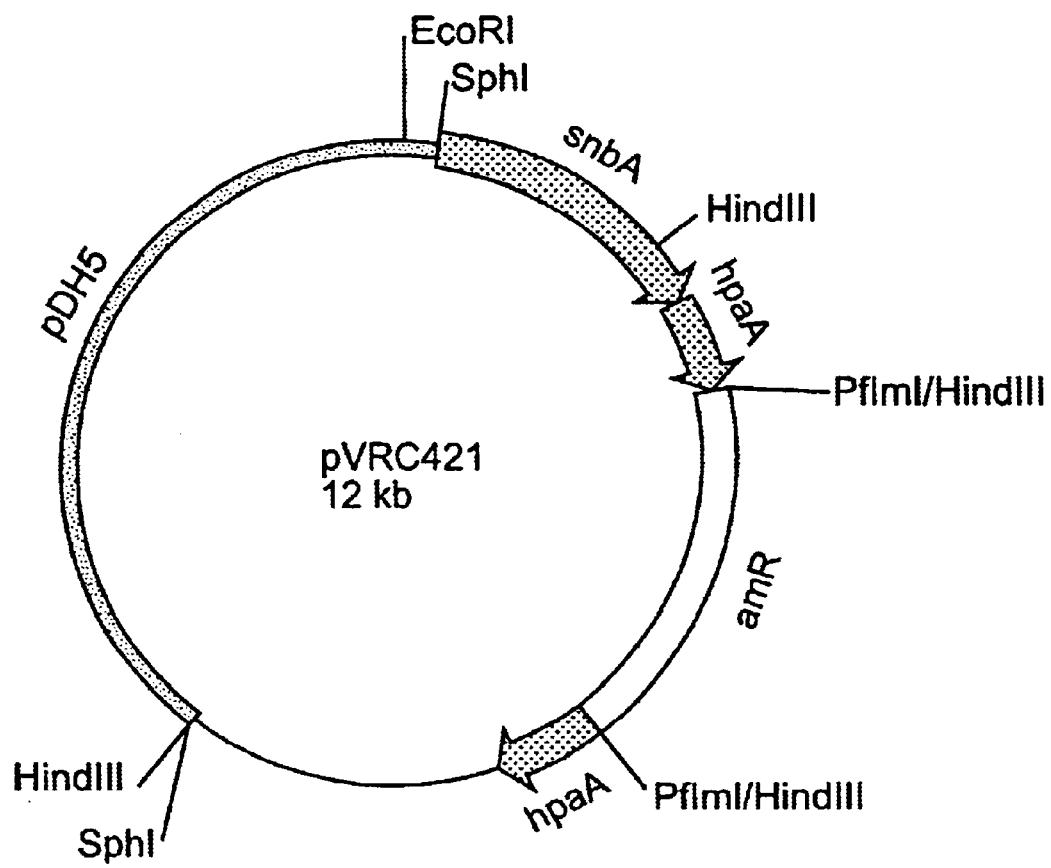

FIG. 11: Depiction of plasmid pVRC421.

Figure 12:
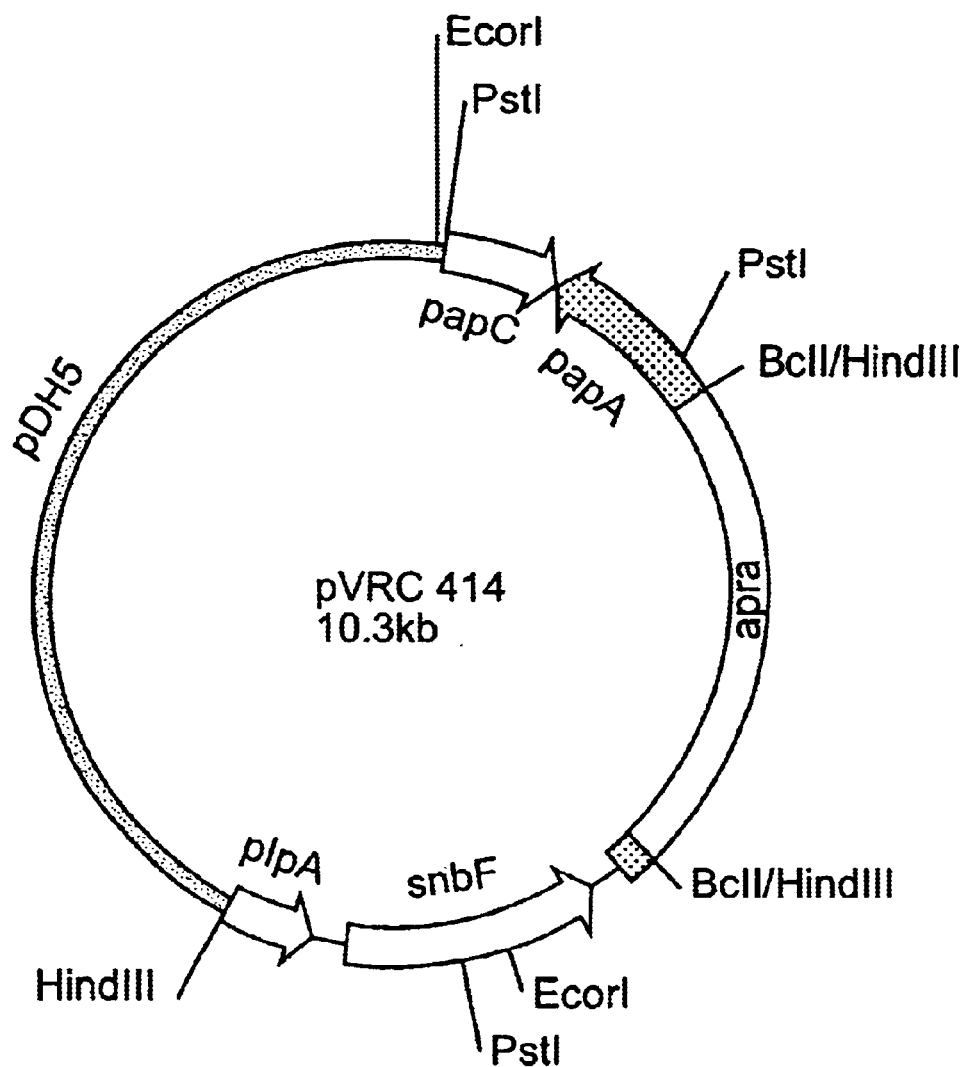

FIG. 12: Depiction of plasmid pVRC414.

FIG. 13: Strategy for constructing SP212.

EXAMPLE 1

Sequencing and Identification of Genes Involved in the Biosynthesis of Pristinamycin I and Its Precursors Identification, by means of sequencing, of the genes situated downstream and upstream of the gene which encodes the enzyme PapA and which is described in Patent PCT/FR93/0923, as well as of a gene which is situated downstream of the gene which encodes the enzyme SnbA and which is also described in Patent PCT/FR93/0923.

This example describes how, using cosmid pIBV2, which is described in Patent PCT/FR93/0923 and which contains the structural genes for the enzymes PapA and PapM, which are involved in the synthesis of the 4-dimethylamino-L-phenylalanine (DMPAPA) precursor of pristinamycin I, and the structural gene for the enzyme SnbA, which is responsible for activating the aromatic precursor, 3-hydroxypicolinic acid (3-HPA), of pristinamycin I, it proved possible to identify, by sequencing around these genes and studying the corresponding mutants, other genes which are involved in the biosynthesis of the DMPAPA precursor or in the biosynthesis of other precursors of pristinamycin I.

With this aim in mind, subclonings were carried out using cosmid pIBV2 and plasmid pVRC900, which is derived from pIBV2 by means of a HindIII deletion and which is also described in Patent PCT/FR93/0923.

This example illustrates how the nucleotide sequences of fragments situated downstream and upstream of the papA and snbA genes of S. pristinaespiralis can be obtained.

The techniques for cloning DNA fragments of interest in the M13mp18 and 19 vectors (Messing et al. 1981) are standard techniques for cloning in Escherichia coli and are described in Maniatis et al. (1989).

1-1 Sequencing and Analysis of the Region Downstream of the papA Gene

In order to sequence this region, which is contained between the papA and papM genes, the PstI-PstI fragment of 1.5 kb, the PstI-XhoI fragment of 0.7 kb, and the XboI-XhoI fragment of 0.7 kb were subcloned into the M13mp18 and M13mp19 vectors proceeding from plasmid pVRC900. The cloning sites were sequenced through by sequencing on double-stranded DNA using plasmids pVRC900 and pVRC409, which are described in Patent PCT/FR93/0923.

The clonings were carried out as follows. Approximately 2 µg of plasmid pVRC900 were cut with restriction enzymes PstI and/or XhoI (New England Biolabs) under the conditions recommended by the supplier. The restriction fragments thus obtained were separated on a 0.8% agarose gel, and the 1.5 kb PstI-PstI, 0.7 kb PstI-XhoI and 0.7 kb XhoI-XhoI fragments of interest were isolated and purified using Geneclean (Bio101, La Jolla, Calif.). For each cloning, approximately 10 ng of M13mp19 and/or M13mp18, cut with PstI and/or XhoI, were ligated to 100 ng of the fragment to be cloned under the conditions described by Maniatis et al. 1989. After transforming the strain TG1 (K12, Δ(lac-pro) supE thi hsd ΔS F' traD36 proA$^+$B$^+$ lacI$^q$ lacZ Δ M15; Gibson, 1984) and selecting lysis plaques on an LB+X-gal+IPTG medium in accordance with the technique described by Maniatis et al. (1989), the phage carrying the desired fragments were isolated. The different inserts were sequenced by the chain termination reaction using, as the synthesis primer, the universal primer or synthetic oligonucleotides which were complementary to a 20 nucleotide sequence of the insert to be sequenced. The reactions were carried out using fluorescent dideoxynucleotides (PRISM Ready Reaction DyeDeoxy Terminator Cycle Sequencing Kit-Applied Biosystem) and analysed on a model 373 A Applied Biosystems DNA sequencer. The overlap between these different inserts was such that it was possible to establish the entire nucleotide sequence between the papA and papM genes (SEQ ID No. 1).

With the aid of this nucleotide sequence, it is possible to determine the open reading frames and thereby identify genes which are involved, in S. pristinaespiralis, in the biosynthesis of PI or its precursors, as well as the polypeptides encoded by these genes.

We looked for the presence of open reading frames within the 2.9 kb PstI-XhoI fragment, which contains the nucleotide sequence between the papA and papM genes, making use of the fact that Streptomyces DNA displays a high percentage of G and C bases as well as a strong bias in the use of codons which make up the coding frames (Bibb et al. 1984). The method of Staden and McLachlan (1982) makes it possible to calculate the probability of coding frames in terms of the codon usage of Streptomyces genes which have already been sequenced and which are assembled in a data file which contains 19673 codons and which was obtained using the BISANCE (Dessen et al. 1990) computer server.

Using this method, it was possible to characterize four highly probable open reading frames within the 2.9 kb PstI-XhoI fragment, which reading frames are depicted in the table below (TABLE I). They are designated frames 1 to 4 according to their position starting from the PstI site. The length of each reading frame in bases, has been indicated, as has its position within the fragment (the PstI site being situated at position 1); the number of amino acids in the encoded polypeptide has also been indicated for open reading frames 2 and 3. Frames 1, 3 and 4 are encoded by the same strand, while frame 2 is encoded by the complementary strand (FIG. 4). Frames 1 and 4 correspond, respectively, to the C-terminal region of the PapA protein and to the N-terminal region of the PapM protein, which proteins were previously identified and described in Patent PCT/FR93/00923.

TABLE I

| Frame number and/or gene name | Position | Number of nucleotides | Number of amino acids |
| --- | --- | --- | --- |
| 1 (PapA) | 1–684 | 684 | — |
| 2 (PapC) (inv) | 949–1836 | 888 | 296 |
| 3 (PapB) | 1873–2259 | 387 | 129 |
| 4 (PapM) | 2259–2887 | 629 | — |

Comparison of the product of frame 2 (TABLE I) with the protein sequences contained in the Genpro library shows a 27% homology with the region involved in the prephenate dehydrogenase activity of the bifunctional TyrA proteins of E. coli (Hudson and Davidson, 1984) and of Erwinia herbicola (EMBL data library, 1991). This region of TyrA catalyses aromatization of prephenate to form 4-hydroxyphenylpyruvate in the biosynthesis of tyrosine. A similar aromatization, proceeding from 4-deoxy-4-aminoprephenate and leading to 4-aminophenylpyruvate is very probably involved in the synthesis of DMPAPA. This reaction will be catalyzed by the product of frame 2, termed PapC (SEQ ID NO: 3).

Comparison of the product of frame 3 (TABLE I) with the protein sequences contained in the Genpro library shows a 24 to 30% homology with the region involved in the chorismate mutase activity of the bifunctional TyrA and PheA proteins of E. coli (Hudson and Davidson, 1984) and of the TyrA protein of Erwinia herbicola. This region catalyzes isomerization of chorismate to form prephenate in the biosynthesis of tyrosine and phenylalanine. A similar isomerization, proceeding from 4-deoxy-4-amino chorismate and leading to 4-deoxy-4-aminoprephenate, is very probably involved in the synthesis of DMPAPA. This reaction would be catalyzed by the product of frame 3, termed PapB (SEQ ID NO: 5).

In the case of TyrA and PheA, the chorismate mutase and prephenate dehydratase, or prephenate dehydrogenase, activities are catalysed by the same protein. In S. pristinaespiralis, the chorismate mutase and prephenate dehydrogenase enzyme activities are catalysed by two separate proteins, i.e. PapB and PapC, respectively.

The sequence homologies demonstrated for the PapB and PapC proteins demonstrate that these two proteins are involved, jointly with the PapA and PapM proteins, in the biosynthesis of the aromatic derivative DMPAPA. In the same way as for papA, disruption of the papB and papC genes should lead to the construction of S. pristinaespiralis strains which are incapable of producing PI but which are able, in the presence of novel precursors, to produce new PIs which are modified at the level of the DMPAPA residue.

1-2. Sequencing and Analysis of the Region Upstream of the papA Gene

This region is contained between the snbA gene, which encodes 3-hydroxypicolinic acid AMP ligase and which is described in Patent PCT/FR93/00923, and the papA gene.

The clonings were carried out as described in Example 1-1, proceeding from plasmid pVRC900 and cosmid pIBV2, which are described in Patent PCT/FR93/00923. The 1.3 kb XhoI-XboI, 0.2 kb XboI-XhoI, 3.3 kb XhoI-XhoI, 1.1 kb HindIII-PstI and 2.2 kb PstI-PstI fragments were subcloned into the M13mp18 and M13mp19 vectors. These different clonings made it possible to pass through all the cloning sites. The different inserts were sequenced as described in 1-1 using, as synthesis primer, the universal primer or synthetic oligonucleotides which were complementary to a 20 nucleotide sequence in the insert to be sequenced.

The overlap between these different inserts enabled the entire nucleotide sequence which is present between the snbA and papA genes (SEQ ID NO: 6) to be established.

On the basis of this nucleotide sequence, it is possible to determine the open reading frames and to identify genes which are involved, in S. pristinaespiralis, in the biosynthesis of precursors of PI, as well as the polypeptides encoded by these genes.

We have looked for the presence of open reading frames within the 4.5 kb XhoI-PstI fragment, which contains the nucleotide sequence between the snbA and papA genes, as described in Example 1.1. Using this method, it was possible to characterize four highly probable open reading frames within the 4.5 kb XhoI-PstI fragment, which frames are depicted in the table below (TABLE II). They are designated frames 1 to 4 in accordance with their position starting from the XhoI site. Their length in bases, and their position within the fragment (the XhoI site being situated at position I) has been indicated for each fragment; the number of amino acids within the encoded polypeptide has also been indicated for open reading frames 2 and 3. Frames 2, 3 and 4 are encoded by the same strand, and frame 1 is encoded by the complementary strand (FIG. 5). Frames 1 and 4 correspond, respectively, to the N-terminal regions of the SnbA and PapA proteins, which were previously identified and described in patent PCT/FR93/00923.

TABLE II

| Frame number and/or gene name | Position | Number of nucleotides | Number of amino acids |
| --- | --- | --- | --- |
| 1 (SmbA) (inv) | 1–329 | 329 | — |
| 2 (PipA) | 607–1671 | 1065 | 355 |
| 3 (SnbF) | 1800–2993 | 1194 | 398 |
| 4 (PapA) | 3018–4496 | 1479 | — |

Comparison of the product of frame 2 (TABLE II) with the protein sequences contained in the Genpro library shows a 30% homology with ornithine cyclodeaminase of Agrobacterium tumefaciens (Schindler et al., 1989). This enzyme is involved in the final step in the catabolism of octopine; it converts L-ornithine into L-proline by means of cyclodeamination. Authors have demonstrated, by means of the incorporation of labelled lysine, that 4-oxopipecolic acid and 3-hydroxypicolinic acid, which are found both in $PI_A$ and in virginiamycin S1, derived from lysine (Molinero et al., 1989; Reed et al., 1989). A reaction in which lysine was cyclodeaminated, similar to that described for ornithine, would lead to the formation of pipecolic acid. Taking this hypothesis into account, the product of frame 2 was termed PipA (SEQ ID NO: 8). The results of mutating the pipA gene, presented in 2-1, demonstrate that the pipA gene is involved solely in the synthesis of pipecolic acid, since this mutation has no effect on the biosynthesis of 3-hydroxypicolinic acid, which is also derived from lysine and of which pipecolic acid could have been a precursor.

Comparison of the product of frame 3 (TABLE II) with the protein sequences contained in the Genpro library shows a 30 to 40% homology with several hydroxylases of the cytochrome P450 type, which hydroxylases are involved in the biosynthesis of secondary metabolites (Omer et al., 1990, Trower et al., 1992). Several hydroxylations can be envisaged in the biosynthesis of precursors of pristinamycin I, in particular in the biosynthesis of 3-HPA (hydroxylation of picolinic acid at the 3 position) and of 4-oxopipecolic acid (hydroxylation of pipecolic acid at the 4 position). The results of mutating the pipA gene, presented in 2-1-3, demonstrate that the product of frame 3 is involved in hydroxylation of the pipecolic acid residue of $PI_E$. The corresponding gene has therefore been termed snbF, and the corresponding protein SnbF (SEQ ID NO: 9 and SEQ ID NO: 10, respectively).

1-3. Sequencing the Region Downstream of the snbA Gene

This region is included between the snbA gene, which encodes 3-hydroxypicolinic acid adenylate ligase, and the snbR gene, which encodes a membrane protein which is probably responsible for transport and for resistance to PI, with both genes having been described in Patent PCT/FR93/00923. Sequencing of this region was carried out using a fragment which was isolated from cosmid pIBV2, as described in Example 1-1.

The 1.6 kb HindIII-BglII fragment was subcloned into the M13mp18 and M13mp19 vectors, proceeding from cosmid pIBV2. The insert was sequenced as described in 1-1, using, as synthesis primer, the universal primer or synthetic oligonucleotides which were complementary to a 20 nucleotide sequence of the insert to be sequenced. On the basis of the nucleotide sequence thus obtained (SEQ ID NO: 11), it is possible to determine the open reading frames and to identify, in S. pristinaespiralis, genes which are involved in the biosynthesis of the precursors of PI, as well as the polypeptides encoded by these genes. We looked for the presence of open reading frames within the 1.6 kb HindIII-BglII fragment, which corresponds to the end of the snbA gene and its downstream region, as described in Example 1-1. A complete open coding frame, encoded by the same strand as the snbA gene (FIG. 6), was detected. Relative to position 1, corresponding to the HindIII site, this frame starts at nucleotide 249, i.e. 30 nucleotides after the end of the snbA gene, and terminates at nucleotide 1481. It is 1233 nucleotides in size, corresponding to a protein of 411 amino acids.

Comparison of the product of this open frame with the protein sequences contained in the Genpro library shows a 30 to 40% homology with a group of proteins which are probably involved (Thorson et al., 1993) in the transamination of intermediates in the biosynthesis of various antibiotics (DnrJ, EryCl, TylB, StrS and PrgL). Synthesis of the 3-HPA precursor, which appears to derive from lysine by a route other than cyclodeamination (see Examples 1-2 and 2-1), could necessitate a transamination step which can be catalyzed by the product of this frame 3, termed HpaA (SEQ ID NO: 13). The results of mutating this gene, presented in 2-2, demonstrate unequivocally that this gene is involved in synthesis of the 3-HPA precursor and confirm our hypothesis.

The genes papB, papC, pipA, snbF and hpaA, which are described in the present invention, are grouped together with the snbA, papA and papM genes on a chromosomal region of approximately 10 kb (FIG. 7). This confirms the presence of a cluster of genes which are involved in the biosynthesis of PI and its precursors. Studying regions upstream and downstream of this cluster should enable the other genes involved in the biosynthesis of PI precursors, in particular L-phenylglycine and L-2-aminobutyric acid, to be identified.

EXAMPLE 2

Construction of Recombinant Strains by Means of Disrupting Identified Genes

This example illustrates how it is possible to demonstrate involvement of the genes described in Example 1 in the biosynthesis of pristinamycin precursors, and also to construct S. pristinaespiralis strains which are able to produce novel pristinamycins. These strains are obtained by disrupting the genes which are involved in the biosynthesis of the residue which it is desired to replace, and the novel pristinamycins are produced by supplementing these mutants with novel precursors.

Strain SP92::pVRCC508, which is employed in the present invention to produce novel derivatives of PI by replacing the precursor DMPAPA with other molecules, is described in Patent PCT/FR93/0923. It is obtained by disrupting, by means of simple crossing over, the papA gene, which is involved in the biosynthesis of the precursor of DMPAPA and is thought to participate in an early step relating to the transamination of chorismate. This disruption has a polar character since, in this mutant, expression of the papM gene (PCT/FR93/0923), which is situated 1.5 kb downstream of the papA gene and is involved in the double methylation of 4-amino-L-phenylalanine to form DMPAPA, is very reduced. Thus, assaying the activity of the SAM-dependant methylation enzyme for converting 4-amino-L-phenylalanine (PAPA) into DMPAPA indicates that mutant SP92::pVRC508 has an activity which is less than 5% of the activity of the wild-type strain.

In the present invention, this strain, SP92::pVRC508, can be used, under appropriate fermentation conditions and supplementation conditions, to produce novel pristinamycins which are modified at the level of the DMPAPA residue, as will be explained in Example 3. Mutants having the same phenotype can be obtained by disrupting the papB or papC genes described in the present invention.

Another type of S. pristinaespiralis strain, whose papA gene is disrupted and which possesses the same phenotype as strain SP92::pVRC508, was obtained in a similar manner by disrupting the papA gene by means of double crossing over. This construction was carried out starting with a 4.6 kb SphI-HindIII fragment, which fragment was isolated from cosmid pIBV2 and contains the 3' region of the pipA gene, the entire snbF and papA genes and the 3' part of the papC gene. This fragment was cloned into the suicide vector pDH5, which vector is only able to replicate in E. coli but carries a resistance marker which is expressed in Streptomyces (the gene for resistance to thiostrepton or to nohiheptide, tsr). This vector, pDH5, was developed by Wohlebben et al (1991 Nucleic Acid Res. 19, 727–731). A BclI-BclI deletion of 1.1 kb was then made in the papA gene, and a 2.2 kb HindIII-HindIII fragment, carrying the amR gene (resistance to geneticin and to apramycin), was introduced after the cohesive ends had been filled in. The recombinant vector was termed pVRC414 and is depicted in FIG. 12. After transforming the pristinamycin-producing strain with plasmid pVRC414, transformants which were resistant to geneticin and sensitive to thiostrepton were isolated and analysed. These clones are the result of a double homologous recombination between the S. pristinaespiralis DNA regions of plasmid pVRC414 and the corresponding chromosomal region of S. pristinaespiralis, as described in FIG. 13. One of these clones was termed SP212. Its phenotype is identical to that of strain SP92::pVRC508 as regards the absence of any production of PI and the ability of the strain to produce new antibiotics in the presence of novel precursors. Advantageously, this type of strain, which is obtained by double crossing over, is more stable than the strains which are obtained by simple crossing over.

2-1. Construction of a mutant of S. pristinaespiralis SP92 whose pipA gene is disrupted.

This example illustrates how it is possible, by means of disrupting the pipA gene, to construct a strain of S. pristinaespiralis SP92 which no longer produces PI under standard fermentation conditions and which is able to produce new pristinamycins, which are modified at the level of the 4-oxopipecolic acid residue of PIA, when novel precursors are added to the fermentation.

It was constructed using a suicide vector, the vector pUC1318, which only replicates in E. coli. This vector does not carry any resistance marker which is expressed in Streptomyces. Its presence in the genome of Streptomyces can only be detected by colony hybridization.

2-1-1. Construction of Plasmid pVRC420

This example illustrates how it is possible to construct a plasmid which does not replicate in S. pristinaespiralis SP92 and which can be employed to disrupt the pipA gene by means of double homologous recombination.

Plasmid pVRC420 was constructed in order to produce the chromosomal mutant of SP92 in which the pipA gene is disrupted, proceeding from cosmid pIBV2, which is described in Patent PCT/FR93/0923. Cosmid pIBV2 was cut with the restriction enzyme PstI and, after the fragments, thus generated, had been separated by electrophoresis on a 0.8% agarose gel, a 2.8 kb PstI-PstI fragment, containing the start of the snbA and snbF genes and the whole of the pipA gene, was isolated and purified using Geneclean (Bio101, La Jolla, Calif.). 50 ng of vector pUC1318, which had been linearized by digesting with PstI, were ligated to 200 ng of the 2.8 kb fragment, as described in Example 1. A clone carrying the desired fragment was isolated following transformation of the strain TG1 and selection on LB+150 µg/ml ampicillin+X-gal+IPTG medium. The recombinant plasmid was termed pVRC415 (FIG. 8). A cassette containing the $am^R$ gene, encoding resistance to apramycin or to geneticin (Kuhstoss et al., 1991), was then introduced into the unique HindIII site of plasmid pVRC415, this site being situated 530 bp downstream of the start of the pipA gene. This construction was effected as follows. A 2.5 kb DNA fragment, containing the $am^R$ gene, the PermE promoter (Bibb et al., 1985) and the first 158 amino acids of the gene for resistance to erythromycin, ermE, was isolated by means of a SalI-BglII double digestion of a plasmid which was derived from plasmids pIJ4026 (plasmid carrying the ermE gene under the control of the PermE promoter) and pHP45Ωam$^R$. After filling in the SalI and BglII protruding 5' cohesive ends using Klenow enzyme in accordance with the protocol described by Maniatis et al., 1989, the fragment containing the am$^R$ gene was cloned into the HindIII site of plasmid pVRC415, whose protruding 5' cohesive ends had also been filled in with Klenow enzyme as previously described. The recombinant plasmid thus obtained was designated pVRC420. Its restriction map is depicted in FIG. 9.

2-1-2. Isolation of Mutant SP92pipA::Ωam$^R$, whose pipA Gene is Disrupted by Homologous Recombination This example illustrates how the mutant of *S. pristinaespiralis* SP92 whose pipA gene is disrupted was constructed.

This mutant was isolated by transforming strain SP92 with the suicide plasmid pVRC420.

The preparation of protoplasts, their transformation and extraction of the total DNA from the recombinant strains were all effected as described by Hopwood et al. (1985).

The strain SP92 was cultured, at 30° C. for 40 hours, in YEME medium (Hopwood et al., 1985), 34% sucrose, 5 mM MgCl$_2$ and 0.25% glycine. The mycelium was protoplasted in the presence of lysozyme, and 5×1 μg of pVRC420 were used to transform (by the method employing PEG) the protoplasts. After one night in which the protoplasts were regenerated on R2YE medium (D. Hopwood et al. 1985), the recombinants were selected by spreading on 3 ml of SNA medium (D. Hopwood et al. 1985) containing 1,500 μg/ml geneticin.

100 clones which were resistant to geneticin were isolated from the 5 transformations that were carried out. These recombinants arise from integration, by means of simple or double homologous recombination between the pipA gene which is carried by the chromosome of strain SP92 and the parts of the pipA gene which are contained in the 5.3 kb fragment carried by the suicide plasmid pVRC420. In order to select the recombinants which were obtained by double crossing over (that is which did not contain the pUC1318 part of plasmid pVRC420 in their genome), colony hybridizations were carried out on 90 clones using pUC19 labelled with [α-$^{32}$P]dCTP as the probe, as described in Maniatis et al (1989). 10 clones were selected which were resistant to geneticin but which did not hybridize the vector pUC 19. The spores of the recombinants were isolated by streaking and growing on HT7 medium containing 10 μg/ml geneticin, and restreaked on the same medium in order to obtain isolated colonies. In order to verify the position at which plasmid pVRC420 was integrated, various Southerns of the total DNA from several recombinant clones, purified as described by Hopwood et al. 1985, were carried out, with hybridization to the 2.8 kb PstI-PstI fragment, which was used as a probe after having been labelled with [α-$^{32}$P]dCTP. The results confirm that these recombinants were obtained by double crossing over between vector pVRC420 and the chromosome of strain SP92, resulting in replacement of the 2.8 kb PstI-PstI fragment, containing the pipA gene, by a 5.3 kb PstI-PstI fragment containing the pipA gene which is disrupted by introduction of the am$^R$ gene. One of these mutants was designated SP92pipA::Ωam$^R$.

2-1-3. Production of Pristinamycins Using Mutant SP92pipA::Ωam$^R$

This example illustrates how it is established that the mutant of *S. pristinaespiralis* SP92 whose pipA gene is disrupted by integration of plasmid pVR420 on the one hand no longer produces PI under standard fermentation conditions and on the other hand exhibits a high level of production of a minor form of the B components of streptogramins in which 4-oxopipecolic acid is replaced by pipecolic acid.

Mutant SP$_{92}$pipA::Ωam$^R$, as well as strain SP92 in the role of a control strain, were cultrured in liquid production medium. The fermentation was carried out as follows: 0.5 ml of a suspension of spores from the abovementioned strain are added, under sterile conditions, to 40 ml of inoculum medium in a 300 ml baffled Erlenmeyer flask. The inoculum medium is made up of g/l corn steep, 15 g/l sucrose, 10 g/l (NH$_4$)$_2$SO$_4$, 1 g/l K$_2$HPO$_4$, 3 g/l NaCl, 0.2 g/l MgSO$_4$-7H$_2$O and 1.25 g/l CaCO$_3$. The pH is adjusted to 6.9 using sodium hydroxide solution before introducing the calcium carbonate. The Erlenmeyer flasks are shaken at 27° C. for 44 h on a rotating shaker at a speed of 325 rpm. 2.5 ml of the previous culture, which is 44 hr old, are added under sterile conditions to 30 ml of production medium in a 300 ml Erlenmeyer flask. The production medium is made up of 25 g/l soya flour, 7.5 g/l starch, 22.5 g/l glucose, 3.5 g/l fodder yeast, 0.5 g/l zinc sulphate and 6 g/l calcium carbonate. The pH is adjusted to 6.0 with hydrochloric acid before introducing the calcium carbonate. The Erlenmeyer flasks are shaken for 24, 28 and 32 hours at 27° C. At each time point, 10 g of must are weighed into a smooth Erlenmeyer flask to which 20 ml of mobile phase, consisting of 34% of acetonitrile and 66% of a solution of 0.1 M KH$_2$PO$_4$ (adjusted to pH 2.9 with concentrated H$_3$PO$_4$) are added for extracting the pristinamycins. After shaking, the whole is centrifuged and the pristinamycins contained in the supernatant are assayed by HPLC by means of injecting 150 μl of the centrifugation supernatant onto a Nucleosil 5-C8 column of 4.6×150 mm, which is eluted with a mixture of 40% acetonitrile and 60% 0.1 M phosphate buffer, pH 2.9. The I pristinamycins are detected by means of their UV absorbance at 206 mn.

The results demonstrated that, under the fermentation conditions employed, mutant SP92pipA::Ωam$^R$ did not produce PI at 24, 28 or 32 hrs of fermentation, while control strain SP92 produced a quantity of PI which was standard for the 3 times which were tested. The quantity of PII which was produced remained the same for the two strains. Mutant SP92pipA::Ωam$^R$ is definitely blocked at a step in the biosynthesis of PI. Fermentation complementation tests were carried out by adding different precursors of PI, separately or together, to the culture in production medium after 16 hours. The results of these complementations demonstrated that when 100 mg/l pipecolic acid and 100 mg/l DMPAPA are added simultaneously to the fermentation medium, the mutant produces what is normally a minor derivative of PI, i.e. PI$_E$ (which is produced by SP92 in a quantity which is less than 5%) at a level which is equivalent to the production of PI$_A$ by the control strain. This production does not take place if the pipecolic acid and the DMPAPA are added separately. PI$_E$ differs from PI$_A$ (major component of PI) in the absence of the keto function in the 4 position on the pipecolic acid. The fact that mutant SP92pipA::Ωam$^R$ can only be complemented by adding pipecolic acid and DMPAPA simultaneously indicates that the papA and probably the papB and papM genes were disrupted by a polar effect of the construct. Thus, all these genes are situated downstream of pipA and are probably cotranscripts together with pipA. Disruption of the latter therefore leads to disruption of the pap genes and, consequently, absence of DMPAPA synthesis. The fact that complementation of mutant SP92pipA::Ωam$^R$ with pipecolic acid results in the production of $PI_E$ and not $PI_A$ leads to two conclusions: the first is that construction of the PI cycle is achieved by incorporating pipecolic acid and not 4-oxopipecolic acid and that a hydroxylation generating the keto function in the 4 position then takes place subsequently. The second is that this hydroxylation is probably carried out by the enzyme SnbF whose structural gene is situated directly downstream of the pipA gene. Thus, the obvious polarity of the disruption of the pipA gene on the pap genes probably involves a polar effect on the snbF gene, which is situated between pipA and the pap genes, which is manifested in inhibition of the function of hydroxylation of the pipecolic acid residue of $PI_E$ to form 4-hydroxypipecolic acid, which is found in $PI_F$ and $PI_G$ (FIG. 2) and then oxidized to 4-oxopipecolic acid in $PI_A$.

Preparing a mutant of this nature made it possible to construct a strain of S. pristinaespiralis which is unable to produce PI except in the presence of the PI precursors DMPAPA and pipecolic acid, using which it is able to produce, in a quantity equivalent to that of the starting strain, what is normally a minor derivative of PI within the pristinamycin mixture. Similarly, in the presence of novel precursors, or of a mixture of novel precursors and of precursors which are normally present in PI, this strain will be able to produce new pristinamycins which are modified in either DMPAPA or 4-oxopipecolic acid or in both these residues.

2-2. Construction of a mutant of S. pristinaespiralis SP92 whose hpaA gene is disrupted.

This example illustrates how it is possible, by means of disrupting the hpaA gene, to construct a strain of S. pristinaespiralis SP92 which no longer produces PI under standard fermentation conditions and which is able to produce new pristinamycins, which are modified at the level of the 3-HPA precursor, when novel precursors are added to the fermentation.

This mutant was constructed using a plasmid which does not replicate in S. pristinaespiralis SP92 and which can be used for disrupting the hpaA gene by means of double homologous recombination.

2-2-1. Construction of the Suicide Plasmid pVRC421

Plasmid pVRC421 was constructed using a suicide vector which, while only being able to replicate in E. coli, carries a resistance marker which is expressed in Streptomyces, i.e. the gene for resistance to thiostrepton or to nosiheptide, tsr. This vector, pDH5, was developed by Hillemann et al. (1991).

Plasmid pVRC421 was constructed in order to produce the chromosomal mutant of SP92 whose hpaA gene is disrupted, making use of cosmid pIBV2, which is described in Patent PCT/FR93/0923. pIBV2 was digested with the restriction enzyme SphI and, after having separated the fragments, thus generated, by means of electrophoresis on a 0.6% agarose gel, a 4.8 kb SphI-SphI fragment, containing the whole of the hpaA gene and virtually the whole of the snbA gene, was isolated and purified using Geneclean as described above. 50 ng of the vector pDH5, linearized by digesting with SphI, were ligated to 200 ng of the 4.8 kb fragment, as subsequently described. A clone harbouring the desired fragment was isolated after transforming the strain TG1 and selecting on LB+150 $\mu$g/ml ampicillin+IPTG+X-gal medium. The recombinant plasmid was designated pVRC411 (FIG. 10). A cassette containing the gene $am^R$, encoding resistance to apramycin or to geneticin, was then introduced at the unique PflmI site of plasmid pVRC411, this site being situated 610 bp downstream of the start of the hpaA gene. This construct was produced as follows. A 2.2 kb DNA fragment, containing the $am^R$ gene, was isolated following digestion of the plasmid pHP45$\Omega am^R$, containing the $am^R$ gene, with HindIII. After filling in the HindIII protruding 5' cohesive ends using Klenow enzyme according to the protocol described by Maniatis et al. 1989, the fragment containing the $am^R$ gene was cloned into the PflmI site of plasmid pVRC411, whose protruding 3' cohesive ends had been rendered blunt using the enzyme T4 polymerase as described in Maniatis et al. 1989. The recombinant plasmid thus obtained was termed pVRC421. Its restriction map is depicted in FIG. 11.

2-2-2. Isolation of mutant $SP_{92}hpaA::\Omega am^R$, whose hpaA gene is disrupted by means of homologous recombination.

This example illustrates how the mutant of S. pristinaespiralis SP92 whose hpaA gene is disrupted was constructed.

This mutant was isolated by transforming strain SP92 with the suicide plasmid pVRC421.

The protoplasts were prepared and transformed as described previously.

Strain SP92 was cultured, at 30° C. for 40 hours, in YEME medium, 34% sucrose, 5 mM $MgCl_2$, 0.25% glycine. The mycelium was protoplasted in the presence of lysozyme, and 5×1 $\mu$g of pVRC421 were employed for transforming (by the method using PEG) the protoplasts. After one night for regenerating the protoplasts on R2YE medium, the recombinants were selected by spreading on 3 ml of SNA medium containing 1,500 $\mu$g/ml geneticin.

600 clones which were resistant to geneticin were isolated from the 5 transformations which were carried out. These recombinants result from integration by means of simple or double homologous recombination between the hpaA gene carried by the chromosome of strain SP92 and the 6 kb fragment of the suicide plasmid pVRC421. In order to select the recombinants obtained by double crossing over (that is, the clones which no longer contain, in their genome, the pDH5 moiety of plasmid pVRC421), the clones were subcultured on HT7 medium containing 400 $\mu$g/ml thiostrepton. 6 clones which were resistant to geneticin but sensitive to thiostrepton were selected. The spores of the recombinants were selected by streaking and growth on HT7 medium containing 10 $\mu$g/ml geneticin, and restreaked on the same medium in order to obtain isolated colonies. In order to verify the position of integration of plasmid pVRC421, various Southerns of the total DNA from the 6 recombinant clones, purified as described by Hopwood et al. 1985, were carried out with hybridization to the 4.8 kb SphI-SphI fragment, which was used as the probe after having been labelled with [$\alpha$-$^{32}$P]dCTP. The results confirm that these recombinants were obtained by double crossing over between the vector pVRC421 and the chromosome of the SP92 strain, resulting in replacement of the 4.8 kb SphI-SphI fragment, containing the hpaA gene, by a 6 kb SphI-SphI fragment which contains the hpaA gene disrupted by the $am^R$ gene. One of these mutants was designated SP92hpaA::$\Omega am^R$.

2-2-3. Production of Pristinamycins by Mutant $SP^{92}hpaA::\Omega am^R$

This example illustrates how it is established that the mutant of S. pristinaespiralis SP92 whose hpaA gene is disrupted by integration of plasmid pVR421 no longer produces PI under the standard fermentation conditions.

Mutant SP92hpaA::$\Omega am^R$, and also strain SP92 in the role of control strain, were cultured in liquid production medium. The fermentation was carried out as described in Example 2-1-3, and the pristinamycins were then extracted and assayed as previously described. The results demonstrated that, under the fermentation conditions employed, mutant SP92hpaA::Ωam$^R$ did not produce PI, either at 24, 28 or 32 hrs of fermentation, whereas the control strain produced a quantity of PI which was standard for the 3 time points tested. The quantity of PII produced remained the same for the two strains. Mutant SP92hpaA::Ωam$^R$ is definitely blocked at a step in the biosynthesis of PI. Complementary fermentation tests were carried out by adding different precursors of PI, separately or together, to the culture in production medium after 16 hours. When 100 mg/l 3-hydroxypicolinic acid are added to the fermentation medium, the mutant then produces PI$_A$ at a level which is equivalent to the production of PI by the control strain. The fact that mutant SP92hpaA::Ωam$^R$ can only be complemented by adding 3-hydroxypicolinic acid demonstrates that the hpaA gene is involved in the synthesis of this precursor.

Construction of this mutant made it possible to produce a strain of S. pristinaespiralis which is mutated as regards its production of PI but which, in the presence of the precursor 3-HPA, is capable of producing PI in a quantity equivalent to that produced by the starting strain. In the same way as in the preceding examples, it can be envisaged that it should be possible, using a mutant of this nature in the presence of novel precursors, to produce new pristinamycins which are modified at the level of the 3-hydroxypicolinic acid residue.

EXAMPLE 3

Production of Compounds of the General Formula I by the Mutant SP92::pVRC508

This example illustrates how the mutant of S. pristinaespiralis SP92 whose papA gene is disrupted by integration of plasmid pVRC508 is able to synthesize new streptogramins in the presence of precursors which are added to the production medium. These precursors can be derivatives of amino acids and, more particularly, of phenylalanine, but also of α-ketocarboxylic acids and, more particularly, of phenylpyruvic acid.

The mutant SP92::pVRC508 was cultured in liquid production medium. The fermentation was carried out as follows: 0.5 ml of a suspension of spores from the previously mentioned strain is added, under sterile conditions, to 40 ml of inoculum medium in a 300 ml baffled Erlenmeyer flask. The inoculum medium is made up of 10 g/l corn steep, 15 g/l sucrose, 10 g/l (NH$_4$)$_2$SO$_4$, 1 g/l K$_2$HPO$_4$, 3 g/l NaCl, 0.2 g/l MgSO$_4$-7H$_2$O and 1.25 g/l CaCO$_3$. The pH is adjusted to 6.9 with sodium hydroxide solution before introducing the calcium carbonate. The Erlenmeyer flasks are shaken at 27° C. for 44 h on a rotating shaker at a speed of 325 rpm. 2.5 ml of the previous culture, which is 44 h old, are added, under sterile conditions, to 30 ml of production medium in a 300 ml Erlenmeyer flask. The production medium consists of 25 g/l soya flour, 7.5 g/l starch, 22.5 g/l glucose, 3.5 g/l fodder yeast, 0.5 g/l zinc sulphate and 6 g/l calcium carbonate. The pH is adjusted to 6.0 with hydrochloric acid before introducing the calcium carbonate. The Erlenmeyer flasks are shaken at 27° C. on a rotating shaker at a speed of 325 rpm. After 16 h, 1 ml of a solution of one of the precursors listed in Table 3 (generally 5 or 10 g/l) is added to the culture. The latter is terminated 8 or 24 h later. The volume of the must is measured immediately, and 2 volumes of mobile phase, consisting of 34% acetonitrile and 66% of a solution of 0.1 M KH$_2$PO$_4$ (adjusted to pH 2.9 with concentrated H$_3$PO$_4$) are added to it for extracting the pristinamycins. After shaking, the whole is centrifuged and the pristinamycins contained in the supernatant are extracted and purified as described in Example 4. They are also assayed by HPLC by means of injecting 150 μl of the centrifugation supernatant onto a Nucleosil 5-C8 4.6×150 mm column, which is eluted with a mixture of 40% acetonitrile and 60% 0.1 M phosphate buffer, pH 2.9. The new I pristinamycins are detected by means of their UV absorbance at 206 nm and, where appropriate, by means of their fluorescence emission (370 nm filter, excitation at 306 nm).

TABLE III

| PRECURSOR | ORIGIN |
|---|---|
| phenylalanine | Janssen |
| 4-dimethylaminophenylalanine | Example 33 |
| 4-methylaminophenylalanine | Example 34-1 |
| 4-aminophenylalanine | Janssen 22.794.96 |
| 4-diethylaminophenylalanine | Example 33 |
| 4-ethylaminophenylalanine | Example 33 |
| 4-methylthiophenylalanine | Example 33 |
| 4-methylphenylalanine | J.P.S 101-312-4/ Example 33 |
| 4-methoxyphenylalanine | Janssen 16.975.97 |
| 4-trifluoromethoxyphenylalanine | Example 34-8 |
| 4-methoxycarbonylphenylalanine | Example 33 |
| 4-chlorophenylalanine | Janssen 15.728.14 |
| 4-bromophenylalanine | Janssen 22.779.81 |
| 4-iodophenylalanine | Bachem F 1675 |
| 4-trifluoromethylphenylalanine | P.C.R. Inc. 12 445-3 |
| 4-tert-butylphenylalanine | Example 35-1 |
| 4-isopropylphenylalanine | Example 36-1 |
| 3-methylaminophenylalanine | Example 35-3 |
| 3-methoxyphenylalanine | J.P.S. 101-313-2 |
| 3-methylthiophenylalanine | Example 34-11 |
| 3-fluoro-4-methylphenylalanine | Example 34-5 |
| 4-tert-butylphenylpyruvic acid | Example 33 |
| 4-methylaminophenylpyruvic acid | Example 34-4 |
| 2-napthylphenylalanine | Bachem F 1865 |
| 4-fluorophenylalanine | Bachem F 1535 |
| 3-fluorophenylalanine | Bachem F 2135 |
| 3-ethoxyphenylalanine | Example 37-1 |
| 2,4-dimethylphenylalanine | Example 33 |
| 3,4-dimethylphenylalanine | Example 33 |
| 3-methylphenylalanine | Example 33 |
| 4-phenylphenylalanine | Example 33 |
| 4-butylphenylalanine | Example 36-3 |
| 2-thienyl-3-alanine | Aldrich 28.728.8 |
| 3-trifluoromethylphenylalanine | Example 33 |
| 3-hydroxyphenylalanine | Aldrich T 9.039.5 |
| 3-ethylaminophenylalanine | Example 35-6 |
| 4-aminomethylphenylalanine | Example 33 |
| 4-allylaminophenylalanine | Example 38-2 |
| 4-diallylaminophenylalanine | Example 38-1 |
| 4-allylethylaminophenylalanine | Example 39-4 |
| 4-ethylpropylaminophenylalanine | Example 39-6 |
| 4-ethylisopropylaminophenylalanine | Example 39-1 |
| 4-ethylmethylcyclopropylamino-phenylalanine | Example 39-8 |
| 4-(1-pyrrolidinyl) phenylalanine | Example 40-1 |
| 4-O-allyltyrosine | Example 33 |
| 4-O-ethyltyrosine | Example 33 |
| 4-ethylthiophenylalanine | Example 33 |
| 4-ethylthiomethylphenylalanine | Example 41-1 |
| 4-O-(2-chloroethyl) tyrosine | Example 42-1 |
| 4-acetylphenylalanine | Example 33 |
| 4-ethylphenylalanine | Example 33 |
| 3-dimethylaminophenylalanine | Example 35-10 |

The following table (TABLE IV) indicates the relative retention times of the new PI's which are produced, taking PI$_A$ as the reference. The absolute retention times were determined at 25° C. in the HPLC system described above; they vary slightly from one injection to another and also in accordance with temperature.

TABLE IV

| Precursor | $t_R$ (relative retention time) of the new PI (Neo PI) | | |
|---|---|---|---|
| | Neo PI$_A$ | Neo PI$_H$ | Other neo PI |
| 4-methylaminophenylalanine | 0.85 | | |
| 4-aminophenylalanine | 0.64 | | |
| 4-methylthiophenylalanine | 1.93 | 2.73 | 1.63 |
| 4-methylphenylalanine | 1.77 | 2.65 | |
| 4-methoxyphenylalanine | 1.46 | | |
| 4-methoxycarbonylphenyl-alanine | 1.49 | | |
| 4-chlorophenylalanine | 2.04 | | |
| 4-bromophenylalanine | 2.16 | | |
| 4-iodophenylalanine | 2.42 | | |
| 4-trifluoromethylphenyl-alanine | 2.56 | 3.74 | |
| 4-tert-butylphenylalanine | 3.34 | | |
| 4-isopropylphenylalanine | 2.80 | | 4.35 |
| 3-methylaminophenylalanine | 1.15 | | |
| 3-methoxyphenylalanine | 1.49 | 2.04 | |
| 3-fluoro-4-methylphenylalanine | 2.93 | | |
| 4-tert-butylphenylpyruvic acid | 3.34 | | |
| 4-methylaminophenylpyruvic acid | 0.85 | | |
| 4-ethylaminophenylalanine | 0.94 | | |
| 4-diethylaminophenylalanine | 0.61 | | |
| 4-allylaminophenylalanine | 1.83 | | |
| 4-diallylaminophenylalanine | 2.64 | | |
| 4-allylethylaminophenyl-alanine | 2.4 | | |
| 4-ethylpropylaminophenyl-alanine | 1.06 | | |
| 4-ethylisopropylamino-phenylalanine | 0.89 | | |
| 4-ethylmethylcyclopropyl-aminophenylalanine | 1.1 | | |
| 4-(1-pyrrolidinyl) phenyl-alanine | 2.0 | | |
| 4-O-trifluoromethyltyrosine | 2.42 | | |
| 4-O-allyltyrosine | 2.62 | | |
| 4-O-ethyltyrosine | 2.2 | | |
| 4-ethylthiophenylalanine | 1.96 | | |
| 4-methylthiomethylphenyl-alanine | 1.98 | | |
| 4-O-(2-chloroethyl) tyrosine | 2.45 | | |
| 4-acetylphenylalanine | 1.61 | | |
| 4-ethylphenylalanine | 1.86 | 2.40 | |
| 3-dimethylaminophenyl-alanine | 1.49 | | |
| 3-methylthiophenylalanine | 1.93 | | |
| 3-O-ethyltyrosine | 1.78 | | |

The new PI, with a $t_R$ of 4.35, for 4-isopropylphenylalanine corresponds to a neo PI$_E$ which is described in Example 14.

The new PI, with a $t_R$ of 1.63, for 4-methylthiophenylalanine corresponds to a 5γ-hydroxy neo PI$_H$, which is described in Example 5.

The mutant SP92::pVRC508 was otherwise fermented in the presence of 4-dimethylaminophenylalanine. Under these conditions of complementation, mutant SP92::pVRC508 produces a quantity of I$_A$ pristinamycins which is equivalent to that produced by strain SP92.

EXAMPLE 4

Preparation of pristinamycin I$_B$ [4ε-methylamino-de(4ζ-dimethylamino)pristinamycin I$_A$] and of 4ζ-amino-de(4ζ-dimethylamino)pristinamycin I$_A$ 4.1: Preparation of pristinamycin I$_B$ [4ε-methylamino-de(4ζ-dimethylamino)pristinamycin I$_A$]

The strain SP92::pVRC508 is cultured in production medium, using 60 Erlenmeyer flasks as described in Example 3, with 1 ml of a 10 g/l aqueous solution of (R,S)-4-methylaminophenylalanine, synthesized as in Example 34-1, being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichlormethane and is successively eluted with plateaus of from 0 to 10% methanol in dichloromethane. The fractions containing pristinamycin I$_B$ are combined and evaporated. The dry residue is taken up in 6 ml of a mixture of 65% water and 35% acetonitrile and injected onto a semi-preparative Nucleosil 7μ C8 10×250 mm column (Macherey Nagel), which is eluted with a mixture of 65% 100 mM phosphate buffer, pH 2.9, and 35% acetonitrile. The fractions containing pristinamycin I$_B$ are combined and extracted with one volume of dichloromethane. The organic phase is washed with water, dried on sodium sulphate and then evaporated. 52 mg of pristinamycin I$_B$ are obtained.

NMR spectrum. $^1$H (400 MHz, CDCl$_3$, δ in ppm, ref. TMS): 0.71 (dd, J=16 and 6 Hz, 1H, 5 β$_2$), 0.92 (t, J=7.5 Hz, 3H: CH$_3$ 2 γ), from 1.10 to 1.40 (mt, 2H: 3 β$_2$ and 3 γ$_2$), 1.34 (d, J=7.5 Hz, 3H: CH$_3$ 1 γ), from 1.50 to 1.85 (mt, 3H: 3 γ$_1$ and CH$_2$ 2 β), 2.03 (mt, 1H, 3 β$_1$), 2.22 (mt, 1H, 5 δ$_2$), 2.33 (broad d, J=16 Hz, 1H: 5 δ$_1$), 2.40 (d, J=16 Hz, 1H: 5 β$_1$), 2.82 (mt, 1H: 5 ε$_2$), 2.81 (s, 3H: 4 NCH$_3$ in the para position of the phenyl), 2.90 (dd, J=12 and 4 Hz, 1H: 4 μ$_2$), 3.29 (s, 3H: 4 NCH$_3$) from 3.20 to 3.45 and 3.60 (2 mts, 1H each: CH$_2$ 3 δ), 3.40 (t, J=12 Hz, 1H: 4 β$_1$), 4.57 (dd, J=7 and 8 Hz, 1H, 3α), 4.75 (broad dd, J=13 and 7 Hz, 1H: 5 ε$_1$), 4.83 (mt, 1H: 2α), 4.89 (broad d, J=10 Hz, 1H: 1α), 5.24 (dd, J=12 and 4 Hz, 1H: 4 α), 5.32 (broad d, J=6 Hz, 1H: 5 α), 5.89 (d, J=9 Hz, 1H: 6 α), 5.90 (broad q, J=7.5 Hz, 1H: 1 β), 6.53 (d, J=9 Hz, 1H: NH 2), 6.53 (d, J=8 Hz, 2H: 4 ε), 7.03 (d, J=8 Hz, 2H: 4 δ), from 7.10 to 7.35 (mt, 5H: aromatic H 6), 7.46 (mt, 2H: 1'H$_5$ and 1'H$_4$), 7.85 (dd, J=5.5 and 2 Hz, 1H: 1'H$_6$), 8.44 (d, J=10 Hz, 1H: NH 1), 8.76 (d, J=9 Hz, 1H: NH 6), 11.63 (s, 1H: OH).

4.2: Preparation of 4ζ-amino-de(4ζ-dimethylamino)pristinamycin I$_A$

Strain SP92::pVRC508 is cultured in production medium, using 60 Erlenmeyer flasks as described in Example 3, with 1 ml of a 5 g/l aqueous solution of (S)-4-aminophenylalanine being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9 and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin I$_A$ are combined and evaporated. The dry residue is taken up in 6 ml of a mixture consisting of 65% water and 35% acetonitrile and injected onto a semi-preparative Nucleosil 7μ C8 10×250 mm column (Macherey Nagel), which is eluted with a mixture consisting of 65% 100 mM phosphate buffer, pH 2.9, and 35% acetonitrile. The fractions containing the new pristinamycin are combined and extracted with one volume of dichloromethane. The organic phase is washed with water, dried over sodium sulphate and then evaporated. 5 mg of 4ζ-amino-de(4ζ-dimethylamino)pristinamycin $I_A$ are obtained.

NMR spectrum: 1H (400 MHz, CDCl$_3$, δ in ppm, ref. TMS): 0.72 (dd, J=16 and 5.5 Hz, 1H, 5 β$_2$), 0.90 (t, J=7.5 Hz, 3H: CH$_3$ 2 γ), from 1.10 to 1.40 (mt, 2H: 3 β$_2$ and 3 γ$_2$), 1.33 (d, J=7.5 Hz, 3H: CH$_3$ 1 γ), from 1.50 to 1.85 (mt, 3H: 3 γ$_1$ and CH$_2$ 2 β), 2.02 (mt, 1H, 3 β$_1$), 2.19 (mt, 1H, 5 $\mu_2$), 2.33 (broad d, J=16 Hz, 1H: 5 δ$_1$), 2.42 (d, J=16 Hz, 1H: 5 β$_1$), 2.82 (dt, J=13 and 4 Hz, 1H: 5 ε$_2$), 2.90 (dd, J=12 and 4 Hz, 1H: 4 β$_2$), 3.24 (s, 3H: NCH$_3$ 4), from 3.20 to 3.40 and 3.54 (2 mts, 1H each: CH$_2$ 3 δ), 3.30 (t, J=12 Hz, 1H: 4 β$_1$), 3.72 (unres.comp., 2H: ArNH$_2$), 4.54 (dd, J=7.5 and 7 Hz, 1H, 3 α), 4.73 (broad dd, J=13 and 8 Hz, 1H: 5 ε$_1$), 4.82 (mt, 1H: 2α), 4.89 (broad d, J=10 Hz, 1H: 1α), 5.22 (dd, J=12 and 4 Hz, 1H: 4 α), 5.32 (broad d, J=5.5 Hz, 1H: 5 α), 5.89 (mt, 2H: 6 α and 1 β), 6.51 (d, J=9.5 Hz, 1H: NH 2) 6.61 (d J=8 Hz, 2H: 4 ε), 6.98 (d, J=8 Hz, 2H: 4δ), from 7.15 to 7.35 (mt, 5H: aromatic H 6), 7.45 (dd, J=8.5 and 1.5 Hz, 1H: 1'H$_4$), 7.48 (dd, J=8.5 and 4 Hz, 1H: 1'H$_5$), 7.82 (dd, J=4 and 1.5 Hz, 1H: 1'H$_6$), 8.43 (d, J=10 Hz, 1H: NH 1), 8.76 (d, J=9.5 Hz, 1H: NH 6), 11.63 (s, 1H: OH).

EXAMPLE 5

Preparation of 4ζ-methylthio-de(4ζ-dimethylamino) pristinamycin $I_A$, of 4ζ-methylthio-de(4ζ-dimethylamino)pristinamycin $I_H$, and of 5-γ-hydroxy-4ζ-methylthio-de(4ζ-dimethylamino) pristinamycin $I_H$ Strain SP92::pVRC508 is cultured in production medium using 60 Erlenmeyer flasks, as described in Example 3, with 1 ml of a 10 g/l solution of (R,S)-4-methylthiophenylalanine, synthesized as in Example 33, in 0.1N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin $I_A$ are combined and evaporated. 65 mg of dry residue are obtained. This is taken up in 6 ml of a mixture consisting of 60% water and 40% acetonitrile and injected in two batches onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 45 mg of 4ζ-methylthio-de(4ζ-dimethylamino)pristinamycin $I_A$ are obtained.

NMR spectrum: 1H (400 MHz, CDCl$_3$, δ in ppm, ref. TMS): 0.68 (dd, J=16 and 5.5 Hz, 1H 5 β$_2$), 0.93 (t, J=7.5 Hz, 3H: CH$_3$, 2 γ), 1.13 (mt, 1H: 3 β$_2$), from 1.25 to 1.40 (mt, 1H: 3 γ$_2$), 1.33 (d, J=7.5 Hz, 3H: CH$_3$ 1 γ), from 1.55 to 1.85 (mt, 3H: 3 γ$_1$, and CH$_2$ 2 β), 2.02 (mt, 1H, 3 β$_1$), 2.18 (mt, 1H, 5 δ$_2$), 2.38 (broad d, J=16.5 Hz, 1H: 5 δ$_1$), 2.46 (s, 3H: SCH$_3$), 2.48 (d, J=16 Hz, 1H, 5 β$_1$), 2.85 (dt, J=13.5 and 4 Hz, 1H: 5 ε$_2$), 3.00 (dd, J=12 and 5 Hz, 1H: 4 β$_2$), 3.23 (s, 3H: NCH$_3$, 4), 3.37 (t, J=12 Hz, 1H: 4 β$_1$), 3.37 and 3.58 (2 mts, 1H each: CH$_2$ 3 δ), 4.55 (t, J=7.5 Hz, 1H, 3 α), 4.77 (broad dd, J=13.5 and 8 Hz, 1H: 5 ε$_1$), 4.86 (mt, 1H: 2α), 4.89 (dd, J=10 and 1.5 Hz, 1H: 1 α), 5.30 (broad d, J=5.5 Hz, 1H: 5 α), 5.32 (dd, J=12 and 5 Hz, 1H: 4 α), 5.90 (d, J=9.5 Hz, 1H: 6 α), 5.92 (dq, J=7.5 and 1.5 Hz, 1H: 1 β), 6.55 (d, J=9.5 Hz, 1H: NH 2), 7.13 (d, J=8 Hz, 2H: 4 δ), from 7.15 to 7.35 (mt, 5H: aromatic H 6), 7.19 (d, J=8 Hz, 2H: 4 ε), 7.45 (mt, 2H: 1'H$_4$ and H$_5$), 7.76 (t, J=5 Hz, 1'H$_6$), 8.42 (d, J=10 Hz, 1H: NH 1), 8.76 (d, J=9.5 Hz, 1H: NH 6), 11.65 (s, 1H: OH).

Using the fractions derived from the silica column described above which contain the novel derivative of pristinamycin $I_H$, 10 mg of 4ζ-methylthio-de(4ζ-dimethylamino)pristinamycin $I_H$ are isolated by means of semi-preparative column chromatography as described above but bringing the proportion of acetonitrile in the eluent phase to 50%.

NMR spectrum: $^1$H (400 MHz, CDCl$_3$, δ in ppm, ref. TMS): 0.32 (mt, 1H, 5 β$_2$), 0.93 (t, J=7.5 Hz, 3H: CH$_3$ 2 γ), from 1.20 to 1.35 (mt, 2H: 3 β$_2$ and 3 γ$_2$), 1.30(d, J=7.5 Hz, 3H: CH$_3$ 1 γ), from 1.35 to 2.05 (mt, 9H: 3 γ$_1$-3 β$_1$-CH$_2$ 2 β-CH$_2$ 5 δ-CH$_2$ 5γ and 5 β$_1$), 2.44 (dt, J=13.5 and 1.5 Hz, 1H: 5 ε$_2$), 2.49 (s,3H: SCH$_3$), 2.99 (dd, J=12 and 5 Hz, 1H: 4 β$_2$), 3.09 (dd, J=12.5 and 12 Hz, 1H: 4 β$_1$), 3.54 and 3.64 (2 mts, 1H each: CH$_2$ 3 δ), 4.17 (dd, J=7 and 6 Hz, 1H: 3 α), 4.49 (broad d, J=13.5 Hz: 1H: 5 ε$_1$), from 4.70 to 4.80 (mt, 3H: 2 α-5 α and 4 α), 4.84 (dd, J=10 and 1.5 Hz, 1H: 1 α), 5.51 (d, J=7 Hz, 1H: 6 α), 5.73 (mt, 1H: 1 β), 6.65 (d, J=9.5 Hz, 1H: NH 2), 7.10 (d, J=8 Hz, 2H: 4 δ), 7.22 (d, J=8 Hz, 2H: 4 ε), from 7.20 to 7.40 (mt, 7H: aromatic H 6=1'H$_4$ and 1'H$_5$), 7.87 (d, J=4 Hz, 1H: 1'H$_6$), 8.55 (unres.comp., 1H: NH 6), 8.55 (d, J=10 Hz, 1H: NH 1), 11.70 (s, 1H: OH).

Using the fractions derived from the silica column described above which contain the novel derivative of pristinamycin I, 3 mg of 5γ-hydroxy-4ζ-methylthio-de(4ζ-dimethylamino)pristinamycin $I_H$ are isolated by carrying out semi-preparative column chromatography as described above and maintaining the proportion of acetonitrile in the eluent phase at 45%.

NMR spectrum: $^1$H (400 MHz, CDCl$_3$, δ in ppm, ref. TMS): a markedly preponderant isomer is observed: the —OH in the 5 γ position in an axial position. 0.37 (d mt, J=16 Hz, 1H, 5 β$_2$), 0.93 (t, J=7.5 Hz, 3H: CH$_3$ 2 γ), from 1.20 to 1.45 (mt, 2H: 3 β$_2$ and 3 γ$_2$) 1.31 (d, J=7.5 Hz, 3H: CH$_3$ 1 γ), from 1.40 to 1.85 (mt, 5H: 3 γ$_1$-CH$_2$ 2 β and CH$_2$ 5 δ), 1.98 (mt, 1H, 3 β$_1$), 2.17 (d, J=16 Hz, 1H: 5 β$_1$), 2.50 (s, 3H: SCH$_3$), 2.77 (dt, J=13.5 and 2 Hz, 1H: 5 ε$_2$), 2.99 (dd, J=12 and 4 Hz, 1H: 4 β$_2$), 3.11 (t, J=12 Hz, 1H: 4 β$_1$), from 3.45 to 3.70 (mt, 2H: CH$_2$ 3 δ), 3.73 (mt, 1H: 5 γ in an equatorial position), 4.13 (t, J=7 Hz, 1H, 3 α), 4.37 (broad d, J=13.5 Hz, 1H: 5 ε$_1$), from 4.75 to 4.95 (mt, 3H: 2α, 4 α and 5 α), 4.89 (dd, J=10 and 1 Hz, 1H: 1 α), 5.70 (d, J=8 Hz, 1H: 6 α), 5.80 (dq, J=7.5 and 1 Hz, 1H: 1 β), 6.37 (d, J=5 Hz, 1H: NH 4), 6.71 (d, J=10 Hz, 1H: NH 2), 7.10 (d, J=8 Hz, 2H: 4 δ), 7.22 (d, J=8 Hz, 2H: 4 ε), from 7.20 to 7.40 (mt, 5H: aromatic H 6), 7.43 (dd, J=8.5 and 1.5 Hz, 1H: 1'H$_4$), 7.46 (dd, J=8.5 and 4 Hz, 1H: 1'H$_5$), 7.89 (dd, J=4 and 1.5 Hz, 1H: 1'H$_6$), 8.55 (d, J=10 Hz, 1H: NH 1), 9.15 (d, J=8 Hz, 1H: NH 6), 11.70 (s, 1H: OH).

EXAMPLE 6

Preparation of 4ζ-methyl-de(4ζ-dimethylamino) pristinamycin $I_A$ and of 4ζ-methyl-de(4ζ-dimethylamino)pristinamycin $I_H$ Strain SP92::pVRC508 is cultured in production medium, using 60 Erlenmeyer flasks, as described in Example 3, with 1 ml of a 5 g/l solution of (R,S)-4-methylphenylalanine in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin $I_A$ are combined and evaporated. 49 mg of dry residue are obtained. This residue is taken up in 6 ml of a mixture consisting of 60% water and 40% acetonitrile and injected, in two batches, onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 44 mg of 4ζ-methyl-de(4ζ-dimethylamino)pristinamycin $I_A$ are obtained.

NMR spectrum: $^1$H (400 MHz, CDCl$_3$ δ in ppm, ref. TMS): 0.52 (dd, J=16 and 6 Hz, 1H, 5 $β_2$), 0.93 (t, J=7.5 Hz, 3H: CH$_3$ 2 γ), 1.15 (mt, 1H: 3 $β_2$), from 1.20 to 1.40 (mt, 1H: 3 $γ_2$), 1.35 (d, J=7.5 Hz, 3H: CH$_3$ 1 γ), from 1.50 to 1.85 (mt, 3H: 3 $γ_1$ and CH$_2$ 2 β), 2.04 (mt, 1H, 3 $β_1$), 2.18 (mt, 1H, 5 $δ_2$), from 2.25 to 2.45 (mt, 2H: 5 $δ_1$ and 5 $β_1$), 2.36 (s, 3H: ArCH$_3$), 2.83 (dt, J=13 and 4 Hz, 1H: 5 $ε_2$), 2.99 (dd, J=13 and 4 Hz, 1H: 4 $β_2$), 3.28 (s, 3H: NCH$_3$4), 3.31 and 3.59 (2 mts, 1H each: CH$_2$ 3 δ), 3.40 (t, J=13 Hz, 1H: 4 $β_1$), 4.59 (t, J=7.5 Hz, 1H, 3 α), 4.74 (broad dd, J=13 and 7 Hz, 1H: 5 $ε_1$), 4.85 (mt, 1H: 2α), 4.89 (broad d, J=10 Hz, 1H: 1α), from 5.25 to 5.35 (mt, 2H: 5 α and 4 α), from 5.85 to 5.95 (mt, 2H: 6 α and 1β), 6.52 (d, J=9.5 Hz, 1H: NH 2), 7.14 (AB limit, J=9 Hz, 4H: 4δ and 4ε), from 7.15 to 7.35 (mt, 5H: aromatic H 6), 7.50 (mt, 2H: 1'H$_4$ and 1'H$_5$), 7.81 (dd, J=4 and 2 Hz, 1H: 1'H$_6$), 8.41 (d, J=10 Hz, 1H: NH 1), 8.74 (d, J=9 Hz, 1H: NH 6), 11.63 (s, 1H:OH).

Using the fractions derived from the silica column described above which contain the new derivative of pristinamycin $I_H$, 21 mg of 4ζ-methyl-de(4ζ-dimethylamino) pristinamycin $I_H$ (mass spectrometry: M+H$^+$=810) are isolated by carrying out semi-preparative column chromatography as described above.

EXAMPLE 7

Preparation of 4ζ-methoxy-de(4ζ-dimethylamino) pristinamycin $I_A$

Strain SP92::pVRC508 is cultured in production medium using 12 Erlenmeyer flasks, as described in Example 3, with 1 ml of a 5 g/l solution of (RS)-4-methoxyphenylalanine in 0.1 N sodium hydroxide solution being added at 16 h. At the end of 40 h of culture, the 0.35 liters of must recovered from the 12 Erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin $I_A$ are combined and evaporated. 14 mg of dry residue are obtained. This residue is taken up in 3 ml of a mixture consisting of 60% water and 40% acetonitrile and injected onto a semi-preparative Nucleosil 7μ C8 10×250 mm column (Machery Nagel), which is eluted with a mixture consisting of 60% 100 mM phosphate buffer, pH 2.9, and 40% acetonitrile. The fractions containing the new pristinamycin are combined and extracted with one volume of dichloromethane. The organic phase is washed with water, dried over sodium sulphate and then evaporated. 12 mg of 4ζ-methoxy-de(4ζ-dimethylamino)pristinamycin $I_A$ are obtained.

NMR spectrum: $^1$H (400 MHz, CDCl$_3$, d in ppm, ref. TMS): 0.63 (dd, J=16 and 5.5 Hz, 1H, 5 $β_2$), 0.96 (t, J=7.5 Hz, 3H: CH$_3$ 2 γ), 1.17 (mt, 1H: 3 $β_2$), from 1.30 to 1.45 (mt, 1H: 3 $γ_2$), 1.38 (d, J=7.5 Hz, 3H: CH$_3$ 1 γ) from 1.55 to 1.85 (mt, 3H: 3 $γ_1$ and CH$_2$ 2 β), 2.05 (mt, 1H, 3 $β_1$), 2.20 (mt, 1H, 5 $δ_2$), 2.40 (broad d, J=16 Hz, 1H: 5 $δ_1$), 2.47 (d, J=16 Hz, 1H: 5 $β_1$), 2.88 (dt, J=13 and 4 Hz, 1H: 5 $ε_2$), 2.99 (dd, J=12.5 and 5 Hz, 1H: 4 $β_2$), 3.30 (s, 3H: NCH$_3$ 4), 3.32 and 3.60 (2 mts, 1H each: CH$_2$ 3 δ), 3.40 (t, J=12.5 Hz, 1H: 4 $δ_1$), 3.80 (s, 3H: OCH$_3$), 4.60 (t, J=7.5 Hz, 1H, 3 α), 4.80 (broad dd, J=13 and 8.5 Hz, 1H: 5 $ε_1$), 4.88 (mt, 1H: 2α), 4.92 (broad d, J=10 Hz, 1H: 1α), 5.31 (dd, J=12.5 and 5 Hz, 1H: 4 α), 5.34 (broad d, J=5.5 Hz, 1H: 5 α), 5.90 (d, J=9 Hz, 1H: 6 α), 5.93 (broad q, J=7.5 Hz, 1H: 1β), 6.54 (d, J=9 Hz, 1H: NH 2), 6.87 (d, J=8 Hz, 2H: 4ε), 7.16 (d, J=8 Hz, 2H: 4δ), from 7.15 to 7.40 (mt, 5H: aromatic H 6), 7.50 (mt, 2H: 1'H$_5$ and 1'H$_4$), 7.80 (dd, J=4 and 2.5 Ez, 1H: 1'H$_6$), 8.43 (d, J=10 Hz, 1H: NH 1), 8.78 (d, J=9 Hz, 1H: NH 6), 11.65 (s, 1H:OH).

EXAMPLE 8

Preparation of 4ζ-methoxycarbonyl-de(4ζ-dimethylamino)pristinamycin $I_A$

Strain SP92::pVRC508 is cultured in production medium using 60 Erlenmeyer flasks, as described in Example 3, with 1 ml of a 10 g/l solution of (R,S)-4-methoxycarbonylphenylalanine, synthesized as in Example 33, being added at 16 h. At the end of 24 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin $I_A$ are combined and evaporated. 14 mg of dry residue are obtained. This residue is taken up in 3 ml of a mixture consisting of 60% water and 40% acetonitrile and injected onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 9 mg of 4ζ-methoxycarbonyl-de(4ζ-dimethylamino)pristinamycin $I_A$ are obtained.

NMR spectrum: $^1$H (400 MHz, CDCl$_3$, δ in ppm, ref. TMS): 0.70 (dd, J=16 and 6 Hz, 1H, 5 β$_2$), 0.93 (t, J=7.5 Hz, 3H: CH$_3$ 2 γ), 1.08 (mt, 1H: 3 β$_2$), from 1.30 to 1.40 (mt, 1HH: 3 γ$_2$), 1.33 (d, J=7.5 Hz, 3H: CH$_3$ 1 γ) from 1.55 to 1.85 (mt, 3H: 3 γ$_1$, and CH$_2$ 2 β), 2.02 (mt, 1H, 3 β$_1$), 2.13 (mt, 1H, 5 δ$_2$), 2.40 (broad d, J=16.5 Hz, 1H: 5 δ1), 2.48 (d, J=16 Hz, 1H, 5 β$_1$), 2.89 (dt, J=14.5 and 4.5 Hz, 1H: 5 ε$_2$), 3.10 (dd, J=13.5 and 6 Hz, 1H: 4 β$_2$), 3.24 (s, 3H: NCH$_3$ 4), 3.38 and 3.61 (2 mts, 1H each: CH$_2$ 3 δ), 3.47 (t, J=13.5 Hz, 1H: 4 β$_1$), 3.96 (s, 3H: COOCH$_3$), 4.55 (t, J=7.5 Hz, 1H, 3 α), 4.78 (broad dd, J=14.5 and 8 Hz, 1H: 5 ε$_1$), 4.86 (mt, 1H: 2α), 4.89 (broad d, J=10 Hz, 1H: 1α), 5.33 (broad d, J=6 Hz, 1H: 5 α), 5.42 (dd, J=13.5 and 6 Hz, 1H: 4 α), 5.92 (d, (J=9.5 Hz) and mt, 1H each: 6 α and 1β respectively), 6.52 (d, J=10 Hz, 1H: NH 2), from 7.15 to 7.35 (mt, 5H: aromatic H 6), 7.28 (d, J=8 Hz, 2H: 4δ), 7.43 (dd, J=9 and 1.5 Hz, 1H: 1'H$_4$), 7.47 (dd, J=9 and 5 Hz, 1H: 1'H$_5$, 7.66 (d, J=5 and 1.5 Hz, 1H: 1'H$_6$), 7.98 (d, J=8 Hz, 2H: 4ε), 8.38 (d, J=10 Hz, 1H: NH 1), 8.76 (d, J=9.5 Hz, 1H: NH 6), 11.70 (s, 1H: OH).

EXAMPLE 9

Preparation of 4ζ-chloro-de(4ζ-(dimethylamino) pristinamycin I$_A$

Strain SP92::pVRC508 is cultured in production medium using 60 Erlenmeyer flasks, as described in Example 3, with 1 ml of a 10 g/l solution of (R,S)-4-chlorophenylalanine in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin I$_A$ are combined and evaporated. The dry residue is taken up in 3 ml of a mixture consisting of 60% water and 40% acetonitrile and injected onto a semi-preparative Nucleosil 7μ C8 10×250 mm column (Macherey Nagel), which is eluted with a mixture consisting of 60% 100 mM phosphate buffer, pH 2.9, and 40% acetonitrile. The fractions containing the new pristinamycin are combined and extracted with one volume of dichloromethane. The organic phase is washed with water, dried over sodium sulphate and then evaporated. 1 mg of 4ζ-chloro-de(4ζ-dimethylamino) pristinamycin I$_A$ is obtained.

NMR spectrum: $^1$H (400 MHz, CDCl$_3$, δ in ppm, ref. TMS): 0.93 (t, J=7.5 Hz, 3H: CH$_3$ 2 γ), 0.95 (dd, J=16 and 5 Hz, 1H, 5 β$_2$), 1.09 (mt, 1H: 3 β$_2$), from 1.20 to 1.40 (mt, 1H: 3 γ$_2$), 1.35 (d, J=7.5 Hz, 3H: CH$_3$ 1 γ) from 1.50 to 1.85 (mt, 3H: 3 γ$_1$ and CH$_2$ 2 β), 2.02 (mt, 1H, 3 β$_1$), 2.17 (mt, 1H, 5 δ$_2$), 2.43 (broad d, J=16 Hz, 1H: 5 δ$_1$), 2.59 (d, J=16 Hz, 1H: 5 β$_1$), 2.90 (dt, J=13.5 and 4 Hz, 1H: 5 ε$_2$), 3.04 (dd, J=13 and 6 Hz, 1H: 4 β$_2$), 3.21 (s, 3H: 4 NCH$_3$), 3.36 (t, J=13 Hz, 1H: 4 β$_1$), 3.39 and 3.59 (2 mts, 1H each: CH$_2$ 3 δ), 4.53 (t, J=7.5 Hz, 3 α), 4.76 (broad dd, J=13.5 and 8 Hz, 1H: 5 ε$_1$), 4.86 (mt, 1H: 2α), 4.87 (broad d, J=10 Hz, 1H: 1α), 5.38 (mt, 2H: 5 α and 4 α), 5.93 (mt, 2H: 6 α and 1β), 6.52 (d, J=10 Hz, 1H: NH 2), 7.12 (d, J=8 Hz, 2H: 4δ) from 7.15 to 7.35 (mt, 7H: aromatic H 6 and 4ε), 7.38 (dd, J=9 and 4.5 Hz, 1H:1'H$_5$), 7.43 (broad d, J=9 Hz, 1H: 1'H$_4$), 7.68 (dd, J=4.5 and 1 Hz, 1H: 1'H$_6$), 8.36 (d, J=10 Hz, 1H: NH 1), 8.75 (d, J=9 Hz, 1H: NH 6), 11.65 (s, 1H:OH).

EXAMPLE 10

Preparation of 4ζ-bromo-de(4ζ-dimethylamino) pristinamycin I$_A$ and of 4ζ-bromo-de(4ζ-dimethylamino)pristinamycin I$_H$ Strain SP92::pVRC508 is cultured in production medium using 60 Erlenmeyer flasks, as described in Example 3, with 1 ml of a 10 g/l solution of (R,S)-4-bromophenylalanine in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin I$_A$ are combined and evaporated. The dry residue is taken up in 6 ml of a mixture consisting of 60% water and 40% acetonitrile and injected in two batches onto a semi-preparative Nucleosil 7μ C8 10×250 mm column (Macherey Nagel), which is eluted with a mixture consisting of 60% 100 mM phosphate buffer, pH 2.9, and 40% acetonitrile. The fractions containing the new pristinamycin are combined and extracted with one volume of dichloromethane. The organic phase is washed with water, dried over sodium sulphate and then evaporated. 6 mg of 4ζ-bromo-de(4ζ-dimethylamino)pristinamycin I$_A$ are obtained.

NMR spectrum: $^1$H (400 MHz, CDCl$_3$, δ in ppm, ref. TMS): 0.93 (J=7.5 Hz, 3H: CH$_3$ 2 γ), 0.95 (dd, J=16 and 5 Hz, 1H, 5 β$_2$), 1.10 (mt, 1H: 3 β$_2$), 1.35 (d, J=7.5 Hz, 3H: CH$_3$ 1 γ) 1.36 (mt, 1H: 3 γ$_2$), from 1.50 to 1.85 (mt, 3H, 3 γ$_1$ and CH$_2$ 2 β), 2.02 (mt, 1H, 3 β$_1$), 2.18 (mt, 1H: 5 δ$_2$), 2.43 (broad d, J=16 Hz, 1H: 5 δ$_1$), 2.59 (d, J=16 Hz, 1H: 5 β$_1$), 2.90 (dt, J=13 and 4 Hz, 1H: 5 ε$_2$), 3.02 (dd, J=13 and 5.5 Hz, 1H: 4 β$_2$), 3.21 (s, 3H: 4 NCH$_3$), 3.33 (dd, J=13-11 Hz, 1H: 4 β$_1$), 3.39 and 3.59 (2 mts, 1H each: CH$_2$ 3 δ), 4.53 (t, J=7.5 Hz, 1H, 3 α), 4.76 (broad dd, J=13 and 7 Hz, 1H: 5 ε$_1$), 4.86 (mt, 1H, 2α), 4.89 (d broad, J=10 Hz, 1H: 1α), 5.37 (broad d, J=5 Hz, 1H: 5 α), (dd, J=11 and 5.5 Hz, 1H: 4 α), 5.92 (mt, 2H: 6 α and 1β), 6.56 (d, J=9.5 Hz, 1H: NH 2), 7.08 (d, J=8 Hz, 2H: 4δ), from 7.15 to 7.35 (mt, 5H: aromatic H 6), 7.40 (mt, 4H: 1'H$_4$-1'H$_5$ and 4ε, 7.70 (broad d, J=5 Hz, 1H: 1'H$_6$), 8.40 (d, J=10 Hz, 1H: NH 1), 8.77 (d, J=9 Hz, 1H: NH 6), 11.68 (s, 1H: OH).

Using the fractions derived from the silica column described above which contain the new derivative of pristinamycin I$_H$, 3 mg of 4ζ-bromo-de(4ζ-dimethylamino) pristinamycin I$_H$ (mass spectrometry: M+H$^+$=874) are isolated by carrying out semi-preparative column chromatography as described above.

EXAMPLE 11

Preparation of 4ζ-iodo-de(4ζ-dimethylamino) pristinamycin I$_A$ and of 4ζ-iodo-de(4ζ-dimethylamino)pristinamycin I$_H$ Strain SP92::pVRC508 is cultured in production medium using 60 Erlenmeyer flasks, as described in Example 3, with 1 ml of a 10 g/l solution of (RS)-4-iodophenylalanine in sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried on sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin $I_A$ are combined and evaporated. The dry residue is taken up in 6 ml of a mixture consisting of 60% water and 40% acetonitrile and injected in two batches onto a semi-preparative Nucleosil 7μ C8 10×250 mm column (Macherey Nagel), which is eluted with a mixture consisting of 60% 100 mM phosphate buffer, pH 2.9, and 40% acetonitrile. The fractions containing the new pristinamycin are combined and extracted with one volume of dichloromethane. The organic phase is washed with water, dried over sodium sulphate and then evaporated. 12 mg of 4ζ-iodo-de(4ζ-dimethylamino)pristinamycin $I_A$ are obtained.

NMR spectrum: $^1$H (400 MHz, CDCl$_3$, δ in ppm, ref. TMS): 0.93 (J=7.5 Hz, 3H: CH$_3$ 2 γ), 0.95 (dd, J=16 and 5.5 Hz, 1H: 5 β$_2$), 1.10 (mt, 1H: 3 β$_2$), 1.35 (d, J=7.5 Hz, 3H: CH$_3$ 1 γ), 1.38 (mt, 1H: 3 γ$_2$), from 1.55 to 1.85 (mt, 3H, 3 γ$_1$ and CH$_2$ 2 β), 2.02 (mt, 1H, 3 β$_1$), 2.17 (mt, 1H: 5 δ$_2$), 2.43 (broad d, J=16.5 Hz, 1H: 5 δ$_1$), 2.60 (d, J=16 Hz, 1H: 5 β$_1$), 2.89 (dt, J=14 and 4.5 Hz, 1H: 5 ε$_2$), 3.02 (dd, J=13 and 5.5 Hz, 1H: 4 β$_2$), 3.21 (s, 3H: NCH$_3$ 4), 3.31 (dd, J=13 and 11 Hz, 1H: 4 β$_1$), 3.39 and 3.59 (2 mts, 1H each: CH$_2$ 3 δ), 4.53 (t, J=7.5 Hz, 1H, 3 α), 4.75 (broad dd, J=14 and 8 Hz, 1H: 5 ε$_1$), 4.83 (mt, 1H: 2α), 4.88 (broad d, J=10 Hz, 1H: 1α), 5.37 (broad d, J=5.5 Hz, 1H: 5 α), 5.39 (dd, J=11 and 5.5 Hz, 1H: 4 α), 5.92 (mt, 2H: 6 α and 1β), 6.54 (d, J=9.5 Hz, 1H: NH 2), 6.94 (d, J=7.5 Hz, 2H: 4δ), from 7.15 to 7.50 (mt, 5H: aromatic H 6), 7.36 (dd, J=9 and 4 Hz, 1H: 1'H$_5$), 7.43 (broad d, J=9 Hz, 1H: 1'H$_4$), 7.62 (d, J=7.5 Hz, 2H: 4ε), 7.68 (d, J=4 Hz, 1H: 1'H$_6$), 8.38 (d, J=10 Hz, 1H: NH 1), 8.76 (d, J=9 Hz, 1H: NH 6), 11.60 (s, 1H: OH).

Using the fractions derived from the silica column described above which contain the new derivative of pristinamycin $I_H$, 6 mg of 4ζ-iodo-de(4ζ-dimethylamino)pristinamycin $I_H$ (mass spectrometry: M+H$^+$=922) are isolated by carrying out semi-preparative column chromatography as described above.

EXAMPLE 12

Preparation of 4ζ-trifluoromethyl-de(4ζ-dimethylamino)pristinamycin $I_A$ and of 4ζ-trifluoromethyl-de(4ζ-dimethylamino)pristinamycin $I_H$ Strain SP92::pVRC508 is cultured in production medium using 60 Erlenmeyer flasks, as described in Example 3, with 1 ml of a 5 g/l solution of (S)-4-trifluoromethylphenylalanine in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried on sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin $I_A$ are combined and evaporated. The dry residue is taken up in 3 ml of a mixture consisting of 60% water and 40% acetonitrile and injected onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 5 mg of 4ζ-trifluoromethyl-de(4ζ-dimethylamino)pristinamycin $I_A$ are obtained.

NMR spectrum: $^1$H (400 MHz, CDCl$_3$, δ in ppm, ref TMS): 0.86 (dd, J=16 and 5.5 Hz, 1H, 5 β$_2$), 0.91 (t, J=7.5 Hz, 3H: CH$_3$ 2γ), 1.13 (mt, 1H: 3 β$_2$), 1.31 (d, J=7.5 Hz, 3H: CH$_3$ 1 γ) 1.42 (mt, 1H: 3 γ$_2$), from 1.55 to 1.80 (mt, 3H: 3 γ$_1$ and CH$_2$ 2 β), 2.02 (mt, 1H, 3 β$_1$), 2.15 (mt, 1H, 5 δ$_2$), 2.40 (broad d, J=16.5 Hz, 1H: 5 δ$_1$), 2.55 (d, J=16 Hz, 1H: 5 β$_1$), 2.88 (dt, J=14 and 4 Hz, 1H: 5 ε$_2$), 3.18 (s, 3H: NCH$_3$ 4), 3.20 and 3.31 (2 dd, respectively J=13 and 6 Hz and J=13 and 10 Hz, 1H each: 4 β$_2$ and 4 β$_1$), 3.42 and 3.60 (2 mts, 1H each: CH$_2$ 3 δ), 4.50 (t, J=7.5 Hz, 1H, 3 α), 4.73 (broad dd, J=14 and 7.5 Hz, 1H: 5 ε$_1$), 4.83 (mt, 1H: 2α), 4.91 (broad d, J=10 Hz, 1H: 1α), 5.40 (broad d, J=5.5 Hz, 1H: 5 α), 5.55 (dd, J=10 and 6 Hz, 1H: 4 α), 5.87 (d, J=9.5 Hz, 1H: 6 α), 5.90 (broad q, J=7.5 Hz, 1H: 1β), 6.68 (d, J=9.5 Hz, 1H: NH 2), from 7.15 to 7.40 (mt, 9H: 4δ-aromatic H 6-1'H$_5$ and 1'H$_4$), 7.52 (d, J=8 Hz, 2H: 4ε), 7.68 (d, J=4 and 1.5 Hz, 1H: 1'H$_6$), 8.43 (d, J=10 Hz, 1H: NH 1), 8.76 (d, J=9.5 Hz, 1H: NH 6), 11.70 (s, 1H: OH).

Using the fractions derived from the silica column described above which contain the new derivative of pristinamycin $I_H$, 4 mg of ζ-trifluoromethyl-de(4ζ-dimethylamino)pristinamycin $I_H$ (mass spectrometry: M+H$^+$=864) are isolated by carrying out semi-preparative column chromatography as described above.

EXAMPLE 13

Preparation of 4ζ-tert-butyl-de(4ζ-dimethylamino)pristinamycin $I_A$

Strain SP92::pVRC508 is cultured in production medium using 60 Erlenmeyer flasks, as described in Example 3, with 1 ml of a 5 g/l solution of (R,S)-4-tert-butylphenylalanine, synthesized as in Example 35-1, in 0.1 N sodium hydroxide solution being added at 16 h. At the end of 40 h of culture, the 1.8 liters of must recovered from the 60 Erlenmeyers are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried on sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin $I_A$ are combined and evaporated. The dry residue is taken up in 7 ml of a mixture consisting of 60% water and 40% acetonitrile and injected in 2 batches onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 30 mg of 4ζ-tert-butyl-de(4ζ-dimethylamino)pristinamycin $I_A$ are obtained.

NMR spectrum: $^1H$ (400 MHz, $CDCl_3$, δ in ppm, ref. TMS, ref. TMS): 0.21 (dd, J=16 and 5.5 Hz, 1H, 5 $β_2$), 0.91 (t, J=7.5 Hz, 3H: $CH_3$ 2 γ), 1.17 (mt, 1H: 3 $β_2$), from 1.20 to 1.40 (mt, 1H: 3 $γ_2$), 1.33 (s, 9H: $CH_3$ of tert-butyl), 1.35 (d, J=7.5 Hz, 3H: $CH_3$ 1 γ), from 1.50 to 1.85 (mt, 3H: 3 $γ_1$ and $CH_2$ 2 β), 2.04 (mt, 1H, 3 $β_1$), 2.13 (mt, 1H, 5 $δ_2$), 2.30 (mt, 2H: 5 $δ_1$ and 5 $δ_1$), 2.80 (dt, J=13 and 4 Hz, 1H: 5 $ε_2$), 3.00 (dd, J=12 and 4 Hz, 1H: 4 $β_2$), 3.29 (s, 3H: $NCH_3$4), 3.31 and 3.59 (2 mts, 1H each: $CH_2$ 3 δ), 3.40 (t, J=12 Hz, 1H: 4 $β_1$), 4.57 (t, J=7.5 Hz, 1H, 3 α), 4.74 (broad dd, J=13 and 7 Hz, 1H: 5 $ε_1$), 4.85 (mt, 1H: 2α), 4.90 (broad d, J=10 Hz, 1H: 1α), 5.21 (broad d, J=5.5 Hz, 1H: 5 α), 5.25 (dd, J=12 and 4 Hz, 1H: 4 α), 5.87(d, J=9 Hz, 1H: 6 α), 5.92 (broad q, J=7.5 Hz, 1H: 1 [lacuna] 1H: 1'$H_6$), 8.45 (d, J=10 Hz, 1H: NH 1), 8.74 (d, J=9 Hz, 1H: NH 6), 11.65 (s, 1H:OH).

EXAMPLE 14

Preparation of 4ζ-isopropyl-de(4ζ-dimethylamino) pristinamycin $I_A$ and of 4ζ-isopropyl-de(4ζ-dimethylamino)pristinamycin $I_E$ Strain SP92::pVRC508 is cultured in production medium using 60 Erlenmeyer flasks, as described in Example 3, with 1 ml of a 10 g/l solution of (R,S)-4-isopropylphenylalanine, synthesized as in Example 36-1, in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin $I_A$ are combined and evaporated. 61 mg of the dry residue are obtained. This residue is taken up in 9 ml of a mixture consisting of 60% water and 40% acetonitrile and injected in 3 batches onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 51 mg of 4ζ-isopropyl-de(4ζ-dimethylamino)pristinamycin $I_A$ are obtained.

NMR spectrum: $^1H$ (250 MHz, $CDCl_3$, δ in ppm, ref. TMS, ref. TMS): 0.31 (dd, J=16 and 5.5 Hz, 1H, 5 $β_2$), 0.91 (t, J=7.5 Hz, 3H: $CH_3$ 2 γ), from 1.00 to 1.45 (mt, 2H: 3 $β_2$ and 3 $γ_2$), 1.25 (d, J=7.5 Hz, 6H: $CH_3$ of isopropyl), 1.35 (d, J=7.5 Hz, 3H: $CH_3$ 1 γ), from 1.50 to 1.85 (mt, 3H: 3 $γ_1$ and $CH_2$ 2 β), from 1.95 to 2.20 (mt, 2H, 3 $β_1$ and 5 $δ_2$), 2.30 (mt, 2H: 5 $δ_1$ and 5 $β_1$), 2.80 (dt, J=13 and 4 Hz, 1H: 5 $ε_2$), 2.88 (mt, 1H: CH of isopropyl), 2.98 (dd, J=12 and 4 Hz, 1H: 4 $β_2$), 3.30 (s, 3H: $NCH_3$ 4), 3.32 and 3.55 (2 mts, 1H each: $CH_2$ 3 δ), 3.38 (t, J=12 Hz, 1H: 4 $β_1$), 4.55 (t, J=7.5 Hz, 1H, 3 α), 4.72 (broad dd, J=13 and 7 Hz, 1H: 5 $ε_1$), 4.85 (mt, 1H: 2α), 4.88 (broad d, J=10 Hz, 1H: 5α), 5.21 (broad d, J=5.5 Hz, 1H: 5α), 5.25 (dd, J=12 and 4 Hz, 1H: 4 α), 5.87 (d, J=9 Hz, 1H: 6 α), 5.90 (broad q, J=7.5 Hz, 1H: 1 β), 6.50 (d, J=9.5 Hz, 1H: NH 2), from 7.05 to 7.35 (mt, 9H: aromatic H 6-4ε and 4δ), 7.50 (mt, 2H: 1'$H_5$ and 1'$H_4$), 7.86 (dd, J=4 and 1.5 Hz, 1H: 1'$H_6$), 8.40 (d, J=10 Hz, 1H: NH 1), 8.72 (d, J=9 Hz, 1H: NH 6), 11.60 (s, 1H: OH).

Using the same fractions derived from the silica column described above, which fractions also contain the new derivative of pristinamycin $I_E$, 5 mg of ζ-isopropyl-de(4ζ-dimethylamino)pristinamycin $I_E$ are isolated by carrying out semi-preparative column chromatography as described above.

NMR spectrum: $^1H$ (400 MHz, $CDCl_3$, δ in ppm, ref TMS): 0.20 (mt, 1H, 5 $β_2$), 0.92 (t, J=7.5 Hz, 3H: $CH_3$ 2 γ), from 1.15 to 1.40 (mt, 2H: 3 $β_2$ and 3 $γ_2$), 1.24 (d, J=7.5 Hz, 6H: $CH_3$ of isopropyl), 1.34 (d, J=7.5 Hz, 3H: $CH_3$ 1 γ), from 1.35 to 2.05 (mt, 9H: 3 $γ_1$-3 $β_1$-$CH_2$ 2 β-$CH_2$ 5 δ-$CH_2$ 5 γ and 5 $β_1$), 2.45 (dt, J=13 and 1.5 Hz, 1H: 5 $ε_2$), 2.89 (mt, 1H: ArCH), 3.09 (dd, J=14 and 7 Hz, 1H: 4 $β_2$), 3.17 (s, 3H: $NCH_3$ 4), 3.25 (dd, J=14 and 9 Hz, 1H: 4$β_1$), 3.32 and 3.52 (2 mts, 1H each: $CH_2$ 3 δ), 4.55 (mt, 2H: 3 α and 5 $ε_1$), 4.80 (mt, 1H: 2α), 4.89 (dd, J=10 and 1.5 Hz, 1H: 1α), 4.90 (mt, 1H: 5 α), 5.35 (dd, J=9 and 7 Hz, 1H: 4 α), 5.60 (d, J=8 Hz, 1H: 6 α), 5.89 (dq, J=7.5 and 1.5 Hz, 1H: 1β), 6.65 (d, J=9.5 Hz, 1H: NH 2), 7.08 (d, J=8 Hz, 2H: 4δ), 7.14 (d, J=8 Hz, 2H: 4ε), from 7.20 to 7.40 (mt, 7H: aromatic H 6-1'$H_4$ and 1'$H_5$), 7.77 (broad d, J=4 Hz, 1H: 1'$H_6$), 8.46 (d, J=10 Hz, 1H: NH1), 8.48 (d, J=8 Hz, 1H: NH 6), 11.70 (s, 1H: OH).

EXAMPLE 15

Preparation of 4ζ-methylamino-de(4ζ-dimethylamino)pristinamycin $I_A$

Strain SP92::pVRC508 is cultured in production medium using 60 Erlenmeyer flasks, as described in Example 3, with 1 ml of a 10 g/l solution of (R,S)-3-methylaminophenylalanine, synthesized as in Example 35-3, in water being added at 16 h. At the end of 40 h of culture, the 1.8 liters of must recovered from the 60 Erlenmeyer flasks are extracted with 2 volumes of a mixture consisting of 66% of 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and is eluted successively with plateaus of from 0 to 10% methanol in dichloromethane. The fractions containing the new derivative of pristinamycin $I_A$ are combined and evaporated. 19 mg of dry residue are obtained. This residue is taken up in 3 ml of a mixture consisting of 60% water and 40% acetonitrile and injected onto a semi-preparative Nucleosil 7μ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 8 mg of 4ε-methylamino-de (4ζ-dimethylamino)pristinamycin $I_A$ are obtained.

NMR spectrum: $^1H$ (400 MHz, $CDCl_3$, δ in ppm, ref. TMS): 0.93 (t, J=7.5 Hz, 3H: $CH_3$ 2 γ), 1.00 (dd, J=16 and 6 Hz, 1H, $β_2$), 1.17 (mt, 1H: 3 $β_2$), from 1.25 to 1.40 (mt, 2H: 3 $γ_2$), 1.35 (d, J=7.5 Hz, 3H: $CH_3$ 1 γ), from 1.55 to 1.80 (mt, 3H: 3 $γ_1$ and $CH_2$ 2 β), 2.03 (mt, 1H, 3 $β_1$), 2.23 (mt, 1H, 5 $\delta_2$), 2.39 (broad d, J=16 Hz, 1H: 5 $\delta_1$), 2.52 (d, J=16 Hz, 1H: 5 $\beta_1$), 2.78 (s, 3H: ArNCH$_3$ 4), 2.85 (dt, J=13 and 4 Hz, 1H: 5 $\epsilon_2$), 2.99 (dd, J=13 and 4.5 Hz, 1H: 4 $\beta_2$), 3.23 (s, 3H: NCH$_3$ 4), 3.25 (t, J=13 Hz, 1H: 4$\beta_1$), 3.38 and 3.58 (2mts, 1H each: CH$_2$ 3 $\delta$), 4.05 (unres. comp., 1H: ArNH), 4.58 (dd, J=6.5 and 7.5 Hz, 1H, 3 $\alpha$), 4.76 (broad dd, J=13 and 8 Hz, 1H: 5 $\epsilon_1$), 4.85 (mt, 1H: 2$\alpha$), 4.87 (broad d, J=10 Hz, 1H: 1$\alpha$), 5.35 (dd, J=13 and 4.5 Hz, 1H: 4 $\alpha$), 5.38 (broad d, J=6 Hz, 1H: 5 $\alpha$), 5.90 (d, J=9.5 Hz, 1H: 6 $\alpha$), 5.91 (mt, 1H: 1$\beta$), 6.36 (broad s, 1H: H 2 of the aromatic moiety at position 4), from 6.45 to 6.55 (mt, 2H: H4 and H6 of the aromatic moiety in position 4), 6.53 (d, J=10 Hz, 1H: NH 2), 7.12 (t, J=8 Hz, 1H: H 5 of the aromatic moiety in position 4), from 7.15 to 7.45 (mt, 5H: aromatic H 6), 7.35 (mt, 2H: 1'H$_4$ and 1'H$_5$), 7.75 (t, J=3 Hz, 1H: 1'H$_6$), 8.40 (d, J=10 Hz, 1H: NH 1), 8.78 (d, J=9.5 Hz, 1H: NH 6), 11.60 (s, 1H: OH).

EXAMPLE 16

Preparation of 4$\epsilon$-methoxy-de(4$\zeta$-dimethylamino) pristinamycin I$_A$ and of 4$\epsilon$-methoxy-de(4$\zeta$-dimethylamino)pristinamycin I$_H$ Strain SP92::pVRC508 is cultured in production medium using 60 Erlenmeyer flasks, as described in Examle 3, with 1 ml of a 5 g/l solution of (S)-3-methoxyphenylalanine in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin I$_A$ are combined and evaporated. 41 mg of dry residue are obtained. This residue is taken up in 6 ml of a mixture consisting of 60% water and 40% acetonitrile and injected in 2 batches onto a semi-preparative Nucleosil 7$\mu$ C8 10×250 mm column (Macherey Nagel), which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 28 mg of 4$\epsilon$-methoxy-de(4$\zeta$-dimethylamino)pristinamycin I$_A$ are obtained.

NMR spectrum: $^1$H (400 MHz, CDCl$_3$, $\delta$ in ppm, ref. TMS): 0.52 (dd, J=16 and 5.5 Hz, 1H, 5 $\beta_2$), 0.90 (t, J=7.5 Hz, 3H: CH$_3$ 2 $\gamma$), from 1.10 to 1.34 (mt, 2H: 3 $\beta_2$ and 3 $\gamma_2$), 1.34 (d, J=7.5 Hz, 3H: CH$_3$ 1 $\gamma$), from 1.50 to 1.80 (mt, 3H: 3 $\gamma_1$ and CH$_2$ 2 $\beta$), 2.40 (m, 1H, 3 $\beta_1$), 2.20 (mt, 1H, 5 $\delta_2$), 2.35 (broad d, J=16 Hz, 1H: 5 $\delta_1$), 2.38 (d, J=16 Hz, 1H: 5 $\beta_1$), 2.83 (dt, J=13 and 4 Hz, 1H: 5 $\epsilon_2$), 2.97 (dd, J=12 and 4 Hz, 1H: 4 $\beta_2$), 3.28 (s, 3H: NCH$_3$ 4), 3.28 and 3.56 (2 mts, 1H each: CH$_2$ 3 $\delta$), 3.40 (t, J=12 Hz, 1H: 4 $\beta_1$), 3.80(s, 3H: OCH$_3$), 4.58 (t, J=7.5 Hz, 1H, 3 $\alpha$), 4.76 (broad dd, J=13 and 8 Hz, 1H: 5 $\epsilon_1$), 4.85 (mt, 1H: 2$\alpha$), 4.90 (broad d, J=10 Hz, 1H: 1$\alpha$): 5.27 (dd, J=12 and 4 Hz, 1H: 4$\alpha$), 5.30 (broad d, J=5.5 Hz, 1H; 5$\alpha$), 5.89 (d, J=9.5 Hz, 1H: 6 $\alpha$), 5.91 (broad q, J=7.5 Hz, 1H: 1), 6.51 (d, J=10 Hz, 1H: NH 2), from 6.80 to 6.90 (mt, 3H: H 2-H 4 and H 6 of the aromatic moiety in position 4), from 7.15 to 7.40 (mt, 6H: H 5 of the aromatic moiety in position 4 and aromatic H 6), 7.45 (broad d, J=9 Hz, 1H: 1'H$_4$), 7.50 (dd, J=9 and 4 Hz, 1H:1'H$_5$), 7.80 (broad d, J=4 Hz, 1H: 1'H$_6$), 8.40 (d, J=10 Hz, 1H: NH 1), 8.73 (d, J=9.5 Hz, 1H: NH 6), 11.62 (s, 1H: OH).

Using the fractions derived from the silica column described above which contain the new derivative of pristinamycin I$_H$, 7 mg of 4$\epsilon$-methoxy-de(4$\zeta$-dimethylamino) pristinamycin I$_H$ (mass spectrometry: M+H$^+$=826) are isolated by carrying out semi-preparative column chromatography as described above.

EXAMPLE 17

Preparation of 4$\epsilon$-fluoro-4$\zeta$-methyl-de(4$\zeta$-dimethylamino)pristinamycin I$_A$ Strain SP92::pVRC508 is cultured in production medium using 60 Erlenmeyer flasks, as described in Example 3, with 1 ml of a 10 g/l solution of (R,S)-3-fluoro-4-methylphenylalanine, synethesized as in Example 34-5, in 0.1 N sodium hydroxide solution being added at 16 h. At the end of 40 h of culture, the 1.8 liters of must recovered from the 60 Erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the new derivative of pristinamycin I$_A$ are combined and evaporated. 15 mg of dry residue are obtained. This residue is taken up in 3 ml of a mixture consisting of 60% water and 40% acetonitrile and injected onto a semi-preparative Nucleosil 7$\mu$ C8 10×250 mm (Macherey Nagel) column, which is eluted with a mixture consisting of 55% 100 mM phosphate buffer, pH 2.9, and 45% acetonitrile. The fractions containing the new pristinamycin are combined and extracted with one volume of dichloromethane. The organic phase is washed with water, dried over sodium sulphate and then evaporated. 9 mg of 4$\epsilon$-fluoro-4$\zeta$-methyl-de(4$\zeta$-dimethylamino)pristinamycin I$_A$ are obtained.

NMR spectrum: $^1$H (400 MHz, CDCl$_3$, $\delta$ in ppm, ref. TMS): 0.60 (dd, J=16 and 5.5 Hz, 1H, 5 $\beta_2$), 0.91 (t, J=7.5 Hz, 3H: CH$_3$ 2 $\gamma$), 1.12 (mt, 1H: 3 $\beta_2$), from 1.25 to 1.35 (mt, 1H: 3$\gamma_2$), 1.33 (d, J=7.5 Hz, 3H: CH$_3$ 1 $\gamma$), from 1.50 to 1.85 (mt, 3H: 3 $\gamma_1$ and CH$_2$ 2 $\beta$), 2.02 (mt, 1H, 3 $\beta_1$), 2.13 (mt, 1H, 5 $\delta_2$), 2.27 (s, 3H: ArCH$_3$), 2.36 (broad d, J=16 Hz, 1H: 5 $\delta_1$), 2.45 (d, J=16 Hz, 1H: 5 $\beta_1$), 2.85 (dt, J=13 and 4.5 Hz, 1H: 5 $\epsilon_2$), 2.97 (dd, J=12.5 and 4.5 Hz, 1H: 4 $\beta_2$), 3.23 (s, 3H: NCH$_3$ 4), 3.30 and 3.56 (2 mts, 1H each: CH$_2$ 3 $\delta$), 3.37 (t, J=12.5 Hz, 1H: 4 $\beta_1$), 4.55 (t, J=7.5 Hz, 1H, 3 $\alpha$), 4.75 (broad dd, J=13 and 8 Hz, 1H: 5 $\epsilon_1$), 4.83 (mt, 1H: 2$\alpha$), 4.89 (broad d, J=10 Hz, 1H: 1$\alpha$), 5.29 (dd, J=12.5 and 4.5 Hz, 1H: 4 $\alpha$), 5.32 (broad d, J=5.5 Hz, 1H: 5 $\alpha$), 5.89 (d J=9.5 Hz, 1H: 6 $\alpha$), 5.92 (mt, 1H: 1$\beta$), 6.49 (d, J=10 Hz, 1H: NH 2), 6.90 (mt, 2H: H 2 and H 6 of the aromatic moiety in position 4), 7.11 (t, J=8 Hz, 1H: H 5 of the aromatic moiety in position 4), from 7.10 to 7.30 (mt, 5H: aromatic H 6), 7.43 (dd, J=8.5 and 1 Hz, 1H: 1'H$_4$), 7.49 (dd, J=8.5 and 4.5 Hz, 1H: 1'H$_5$), 7.75 (dd, J=4.5 and 1 Hz, 1H: 1'H$_6$), 8.48 (d, J=10 Hz, 1H: NH 1), 8.70 (d, J=9.5 Hz, 1H: NH 6), 11.60 (s, 1H: OH).

EXAMPLE 18

Preparation of 4$\zeta$-ethylamino-de(4$\zeta$-dimethylamino) pristinamycin I$_A$ Strain SP92::pVRC508 is cultured in production medium using 50 erlenmeyer flasks, as described in Example 3, with 1 ml of a 20 g/l solution of (R,S)-4-ethylaminophenylalanine dihydrochloride, synthesized as in Example 33, in 0.1N sodium hydroxide solution being added at 16 h. At the end of 40 h of culture, the 1.5 liters of must recovered from the 50 erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica column (30 g) which is mounted in dichloromethane and eluted successively with plateaus of from 0 to 10% methanol in dichloromethane. The fractions containing 4ζ-ethylamino-de(4ζ-dimethylamino) pristinamycin $I_A$ are combined and evaporated. The dry residue is taken up in 7 ml of a mixture consisting of 65% water and 35% acetonitrile and injected onto a semi-preparative Nucleosil 7μ C8 10×250 mm (Macherey Nagel) column, which is eluted with a mixture consisting of 60% 100 mM phosphate buffer, pH 2.9, and 40% acetonitrile. The fractions containing 4ζ-ethylamino-de(4ζ-dimethylamino) pristinamycin $I_A$ are combined and extracted with one volume of dichloromethane. The organic phase is washed with water, dried over sodium sulphate and then evaporated. 10 mg of 4ζ-ethylamino-de(4ζ-dimethylamino)pristinamycin $I_A$ are obtained.

NMR spectrum. $^1$H (400 MHz, CDCl$_3$, δ in ppm, ref. TMS): 0.72 (dd, J=16 and 6 Hz, 1H: 1H of the CH$_2$ in 5 β); 0.90 (t, J=7.5 Hz, 3H: CH$_3$ in 2γ); 1.15 (mt, 1H: 1H of the CH$_2$ in 3 β); from 1.20 to 1.40 (mt, 1H: 1H of the CH$_2$ in 3 γ); 1.27 (t, J=7.5 Hz, 3H: CH$_3$ of the ethyl); 1.33 (d, J=7 Hz, 3H: CH$_3$ in 1 γ); from 1.50 to 1.65 (mt, 1H: the other H of the CH$_2$ in 3 γ); 1.60 and 1.74 (2 mts, 1H each: CH$_2$ in 2 β); 2.02 (mt, 1H: the other H of CH$_2$ in 3 β); 2.21 and 2.33 (respectively, mt and broad d, J=16.5 Hz, 1H each: CH$_2$ in 5 β); 2.40 (d, J=16 Hz, 1H: the other H of the CH$_2$ in 5 β); 2.82 (dt, J=13 and 4.5 Hz, 1H: 1H of the CH$_2$ in 5ε); 2.89 (dd, J=12 and 4 Hz, 1H: 1H of the CH$_2$ in 4 β); 3.10 (mt, 2H: NCH$_2$ of the ethyl); from 3.20 to 3.35 (mt, 1H: 1H of the CH$_2$ in 3 δ); 3.26 (s, 3H: NCH$_3$); 3.31 (t, J=12 Hz, 1H: the other H of the CH$_2$ in 4 β); 3.54 (mt, 1H: the other H of the CH$_2$ in 3 δ); 3.67 (unres. comp., 1H: NH); 4.56 (dd, J=6.5 and 7 Hz, 1H: 3 α); 4.75 (broad dd, J=13 and 8 Hz, 1H: the other H of the CH$_2$ in 5 ε); 4.84 (mt, 1H: 2 α); 4.90 (broad d, J=10 Hz, 1H: 1 α); 5.24 (dd, J=12 and 4 Hz, 1H: 4 α); 5.32 (broad d, J=6 Hz, 1H: 5 α); 5.88 (d, J=9.5 Hz, 1H: 6 α); 5.90 (mt, 1H: 1β); 6.52 (d, J=8 Hz, 3H: NH in 2 and aromatic H in 4 ε); 7.00 (d, J=8 Hz, 2H: aromatic H in 4 δ); from 7.10 to 7.35 (mt, 5H: aromatic H in 6); 7.46 (limiting AB, 2H: 1'H$_4$ and 1'H$_5$); 7.84 (dd, J=4 and 1 Hz, 1H: 1'H$_6$); 8.45 (d, J=10 Hz, 1H: NH in 1); 8.77 (d, J=9.5 Hz, 1H: NH in 6); 11.65 (s, 1H: OH).

EXAMPLE 19

Preparation of 4ζ-diethylamino-de(4ζ-dimethylamino)pristinamycin $I_A$

Strain SP92::pVRC508 is cultured in production medium using 50 erlenmeyer flasks, as described in Example 3, with 1 ml of a 20 g/l solution of (R,S)-4-ethylaminophenylalanine dihydrochloride, synthesized as in Example 33, in 0.1N sodium hydroxide solution being added at 16 h. At the end of 40 h of culture, the 1.5 liters of must recovered from the 50 erlenmeyer flasks are extracted with 2 volumes of a mixture of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica column (30 g) which is mounted in dichloromethane and eluted successively with plateaus of from 0 to 10% methanol in dichloromethane. The fractions containing 4ζ-diethylamino-de(4ζ-dimethylamino) pristinamycin $I_A$ are combined and evaporated. The dry residue is taken up in 7 ml of a mixture consisting of 60% water and 40% acetonitrile and injected in two portions onto a semi-preparative Nucleosil 7μ C8 10×250 mm (Macherey Nagel) column, which is eluted with a mixture consisting of 68% 100 mM phosphate buffer, pH 2.9, and 32% acetonitrile. The fractions containing 4ζ-diethylamino-de(4ζ-dimethylamino)pristinamycin $I_A$ are combined and extracted with one volume of dichloromethane. The organic phase is washed with water, dried over sodium sulphate and then evaporated. 50 mg of 4ζ-diethylamino-de(4ζ-dimethylamino)pristinamycin $I_A$ are obtained.

NMR spectrum. $^1$H (400 MHz, CDCl$_3$, δ in ppm, ref TMS): 0.65 (dd, J=16 and 6 Hz, 1H: 1H of the CH$_2$ in 5 β); 0.90 (t, J=7.5 Hz, 3H: CH$_3$ in 2 γ); 1.14 (t, J=7 Hz, 6H: CH$_3$ of the ethyl); 1.15 (mt, 1H: 1H of the CH$_2$ in 3 β); 1.26 (mt, 1H: 1H of the CH$_2$ in 3 γ); 1.32 (d, J=6.5 Hz, 3H: CH$_3$ in 1 γ); 1.55 (mt, 1H: the other H of the CH$_2$ in 3 γ); 1.63 and 1.75 (2 mts, 1H each: CH$_2$ in 2 β): 2.02 (mt, 1H: the other H of the CH$_2$ in 3 β); 2.22 and 2.31 (respectively, mt and broad d, J=16.5 Hz, 1H each: CH$_2$ in 5 δ); 2.37(d, J=16 Hz, 1H: the other H of the CH$_2$ in 5 β); 2.80 (dt, J=13 and 4.5 Hz, 1H: 1H of the CH$_2$ in 5 ε); 2.89 (dd, J=12.5 and 4 Hz, 1H: 1H of the CH$_2$ in 4 β); from 3.20 to 3.40 (mt, 6H: NCH$_2$ of the ethyl-1H of the CH$_2$ in 3 δ and other H of the CH$_2$ in 4 β); 3.27 (s, 3H: NCH$_3$); 3.55 (mt, 1H: the other H of the CH$_2$ in 3 δ); 4.58 (dd, J=8 and 6 Hz, 1H: 3 α); 4.76 (broad dd, J=13 and 7.5 Hz, 1H: the other H of the CH$_2$ in 5 ε); 4.84 (mt, 1H: 2 α); 4.89 (dd, J=10 and 1 Hz, 1H: 1 α); 5.21 (dd, J=12.5 and 4 Hz, 1H: 4 α); 5.28 (broad d, J=6 Hz, 1H: 5 α); 5.87 (d, J=9.5 Hz, 1H: 6 α); 5.90 (mt, 1H: 1 β); 6.52 (d, J=9.5 Hz, 1H: NH in 2); 6.60 (d, J=8 Hz, 2H: aromatic H in 4 ε); 7.02 (d, J=8 Hz, 2H: aromatic H in 4 δ); from 7.10 to 7.35 (mt, 5H: aromatic H in 6); 7.46 (limiting AB, 2H: 1'H$_4$ and 1'H$_5$); 7.88 (dd, J=4.5 and 2.5 Hz, 1H: 1'H$_6$); 8.43 (d, J=10 Hz, 1H: NH in 1); 8.76 (d, J=9.5 Hz, 1H: NH in 6); 11.62 (s, 1H: OH).

EXAMPLE 20

Preparation of 4ζ-diallylamino-de(4ζ-dimethylamino)pristinamycin $I_A$

Strain SP92::pVRC508 is cultured in production medium using 94 erlenmeyer flasks, as described in Example 3, with 1 ml of a 20 g/l solution of (R,S)-4-diallylaminophenylalanine dihydrochloride, synthesized as in Example 38-1, in water being added at 16 h. At the end of 40 h of culture, the 2.8 liters of must recovered from the 94 erlenmeyer flasks are extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-diallylamino-de(4ζ-dimethylamino)

pristinamycin I$_A$ are combined and evaporated. The dry residue is taken up in 7 ml of a mixture consisting of 60% water and 40% acetonitrile and injected onto a semi-preparative Nucleosil 7μ C8 10×250 mm (Machery Nagel) column, which is eluted with a mixture consisting of 52% 100 mM phosphate buffer, pH 2.9, and 48% acetonitrile. The fractions containing 4ζ-diallylamino-de(4ζ-dimethylamino) pristinamycin I$_A$ are combined and extracted with one volume of dichloromethane. The organic phase is washed with water, dried over sodium sulphate and then evaporated. 15 mg of 4ζ-diallylamino-de(4ζ-dimethylamino)pristinamycin I$_A$ are obtained.

NMR spectrum. $^1$H (400 MHz, CDCl$_3$, δ in ppm, ref TMS): 0.55 (dd, J=16 and 6 Hz, 1H: 1H of the CH$_2$ in 5 β); 0.93 (t, J=7.5 Hz, 3H: CH$_3$ in 2 γ); 1.18 (mt, 1H: 1H of the CH$_2$ in 3 β); 1.25 (mt, 1H: 1H of the CH$_2$ in 3 γ); 1.34 (d, J=6.5 Hz, 3H: CH$_3$ in 1 γ); 1.59 (mt, 1H: the other H of the CH$_2$ in 3 γ); 1.68 and 1.78 (2 mts, 1H each: CH$_2$ in 2 β); 2.04 (mt, 1H: the other H of CH$_2$ in 3 β); 2.25 and 2.34 (respectively, mt and broad d, J=16.5 Hz, 1H each: CH$_2$ in 5 δ); 2.40 (d, J=16 Hz, 1H: the other H of the CH$_2$ in 5 β); 2.83 (dt, J=13 and 4.5 Hz, 1H: 1H of the CH$_2$ in 5 ε); 2.92 (dd, J=12 and 4 Hz, 1H: 1H of the CH$_2$ in 4 β); from 3.20 to 3.30 (mt, 1H: 1H of the CH$_2$ in 3 δ); 3.29 (s, 3H: NCH$_3$); 3.33 (t, J=12 Hz, 1H: the other H of the CH$_2$ in 4 β); 3.57 (mt, 1H: the other H of the CH$_2$ in 3 δ); 3.93 (limiting AB, 4H: NCH$_2$ of the allyl); 4.60 (dd, J=8 and 6.5 Hz, 1H: 3 α); 4.78 (broad dd, J=13 and 7.5 Hz, 1H: the other H of the CH$_2$ in 5 ε); 4.87 (mt, 1H: 2 α); 4.92 (dd, J=10 and 1 Hz, 1H: 1 α); from 5.10 to 5.25 (mt, 5H: 4 α and =CH$_2$ of the allyl); 5.28 (broad d, J=6 Hz, 1H: 5 α); 5.85 (mt, 2H: CH= of the allyl); 5.92 (d, J=9.5 Hz, 1H: 6 α); 5.94 (mt, 1H: 1 β); 6.54 (d, J=10 Hz, 1H: NH in 2); 6.65 (d, J=8 Hz, 2H: aromatic H in 4 ε); 7.05 (d, J=8 Hz, 2H: aromatic H in 4 δ); from 7.10 to 7.35 (mt, 5H: aromatic H in 6); 7.51 (limiting AB, 2H: 1'H$_4$ and 1'H$_5$); 7.88 (dd, J=4 and 2 Hz, 1H: 1'H$_6$); 8.43 (d, J=10 Hz, 1H: NH in 1); 8.77 (d, J=9.5 Hz, 1H: NH in 6); 11.65 (s, 1H: OH).

EXAMPLE 21

Preparation of 4ζ-allylethylamino-de(4ζ-dimethylamino)pristinamycin I$_A$

Strain SP92::pVRC508 is cultured in production medium using 26 erlenmeyer flasks, as described in Example 3, with 1 ml of a 20 g/l solution of (R,S)-4-allylethylaminophenylalanine dihydrochloride, synthesized as in Example 39-4, in 0.1N sodium hydroxide solution being added at 16 h. At the end of 40 h of culture, the 0.78 liter of must recovered from the 26 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-allylethylamino-de(4ζ-dimethylamino)pristinamycin I$_A$ are combined and evaporated. The dry residue is taken up in 7 ml of a mixture consisting of 60% water and 40% acetonitrile and injected onto a semi-preparative Nucleosil 7μ C8 10×250 mm (Macherey Nagel) column, which is eluted with a mixture consisting of 52% 100 mM phosphate buffer, pH 2.9, and 48% of acetonitrile. The fractions containing 4ζ-allylethylamino-de(4ζ-dimethylamino) pristinamycin I$_A$ are combined and extracted with one volume of dichloromethane. The organic phase is washed with water, dried over sodium sulphate and then evaporated. 20 mg of 4ζ-allylethylamino-de(4ζ-dimethylamino) pristinamycin I$_A$ are obtained.

NMR spectrum. $^1$H (400 MHz, CDCl3, δ in ppm, ref. TMS): 0.58 (dd, J=16 and 6 Hz, 1H: 1H of CH$_2$ in 5 β); 0.91 (t, J=7.5 Hz, 3H: CH$_3$ in 2 γ); 1.16 (t, J=7 Hz, 3H: CH$_3$ of the ethyl); 1.16 (mt, 1H: 1H of the CH$_2$ in 3 β); 1.25 (mt, 1H: 1H of CH$_2$ in 3 γ); 1.32 (d, J=6.5 Hz, 3H: CH$_3$ in 1 γ); 1.54 (mt, 1H: the other H of the CH$_2$ in 3 γ); 1.63 and 1.75 (2 mts, 1H each: CH$_2$ in 2 β); 2.02 (mt, 1H: the other H of the CH$_2$ in 3 β); 2.23 and 2.31 (respectively, mt and broad d, J=16.5 Hz, 1H each: CH$_2$ in 5 δ); 2.37 (d, J=16 Hz, 1H: the other H of the CH$_2$ in 5 β); 2.80 (dt, J=13 and 4.5 Hz, 1H: 1H of CH$_2$ in 5 ε); 2.87 (dd, J=12 and 4 Hz, 1H: 1H of the CH$_2$ in 4 β); from 3.15 to 3.30 (mt, 1H: 1H of the CH$_2$ in 3 δ); 3.26 (s, 3H: NCH$_3$); 3.30 (t, J=12 Hz, 1H: the other H of CH$_2$ in 4 β); 3.36 (mt, 2H: NCH$_2$ of the ethyl); 3.54 (mt, 1H: the other H of the CH$_2$ in 3 δ); 3.90 (limiting AB, 2H: NCH$_2$ of the allyl); 4.57 (dd, J=8 and 6 Hz, 1H, 3 α); 4.76 (broad dd, J=13 and 7.5 Hz, 1H: the other H of the CH$_2$ in 5 ε); 4.84 (mt, 1H: 2 α); 4.89 (dd, J=10 and 1 Hz, 1H: 1 α); from 5.05 to 5.20 (mt, 3H: 4 α and =CH$_2$ of the allyl); 5.27 (broad d, J=6 Hz, 1H: 5 α); 5.83 (mt, 1H: CH= of the allyl); 5.88 (d, J=9.5 Hz, 1H: 6 α); 5.91 (mt, 1H: 1 δ); 6.50 (d, J=10 Hz, 1H: NH in 2); 6.60 (d, J=8 Hz, 2H: aromatic H in 4 ε); 7.02 (d, J=8 Hz, 2H: aromatic H in 4 δ); from 7.10 to 7.35 (mt, 5H: aromatic H in 6); 7.47 (limiting AB, 2H: 1'H$_4$ and 1'H$_5$); 7.88 (dd, J=4 and 2 Hz, 1H: 1'H$_6$); 8.41 (d, J=10 Hz, 1H: NH in 1); 8.75 (d, J=9.5 Hz, 1H: NH in 6); 11.62 (s, 1H: OH).

EXAMPLE 22

Preparation of the 4ζ-ethylpropylamino-de(4ζ-dimethylamino)pristinamycin I$_A$

Strain SP92::pVRC508 is cultured in production medium using 60 erlenmeyer flasks, as described in Example 3, with 1 ml of a 20 g/l solution of (R,S)-4-ethylpropylaminophenylalanine dihydrochloride, synthesized as in Example 39-6, in 0.1N sodium hydroxide solution being added at 16 h. At the end of 40 h of culture, the 1.8 liter of must recovered from the 60 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-ethylpropylamino-de(4ζ-dimethylamino)pristinamycin I$_A$ are combined and evaporated. The dry residue is taken up in 7 ml of a mixture consisting of 60% of water and 40% acetonitrile and injected onto a semi-preparative Nucleosil 7μ C8 10×250 mm (Macherey Nagel) column, which is eluted with a mixture consisting of 63% 100 mM phosphate buffer, pH 2.9, and 37% of acetonitrile. The fractions containing 4ζ-ethylpropylamino-de(4ζ-dimethylamino) pristinamycin I$_A$ are combined and extracted with one volume of dichloromethane. The organic phase is washed with water, dried over sodium sulphate and then evaporated. 16 mg of 4ζ-ethylpropylamino-de(4ζ-dimethylamino) pristinamycin I$_A$ are obtained.

NMR spectrum. $^1$H (400 MHz, CDCl$_3$, δ in ppm, ref. TMS): 0.67 (dd, J=16 and 6 Hz, 1H: 1H of the CH$_2$ in 5 β); 0.91 (t, J=7.5 Hz, 3H: CH$_3$ in 2 γ); 0.95 (t, J=7.5 Hz, 3H: CH$_3$ of propyl); 1.14 (t, J=7 Hz, 3H: CH$_3$ of the ethyl); 1.15 (mt, 1H: 1H of the CH$_2$ in 3 β); 1.25 (mt, 1H: 1H of the CH$_2$ in 3 γ); 1.33 (d, J=7 Hz, 3H: CH$_3$ in 1 γ); from 1.45 to 1.65 (mt, 3H: the other H of the CH$_2$ in 3 γ and CH$_2$ propyl); 1.63 and 1.75 (2 mts, 1H each: CH$_2$ in 2 β); 2.02 (mt, 1H: the other H of the CH$_2$ in 3 β); 2.23 and 2.33 (respectively, mt and broad d, J=16.5 Hz, 1H each: CH$_2$ in 5 δ); 2.37 (d, J=16 Hz, 1H: the other H of the CH$_2$ in 5 β); 2.80 (dt, J=13 and 5 Hz, 1H: 1H of the CH$_2$ in 5 ε); 2.89 (dd, J=12 and 4 Hz, 1H: 1H of the CH$_2$ in 4 β); from 3.10 to 3.25 (mt, 3H: 1H of the CH$_2$ in 3 δ and NCH$_2$ of the propyl); 3.26 (s, 3H: NCH$_3$); from 3.25 to 3.40 (mt, 2H: NCH$_2$ of the ethyl); 3.34 (t, J=12 Hz, 1H: the other H of the CH$_2$ in 4 β); 3.54 (mt, 1H: the other H of the CH$_2$ in 3 δ); 4.57 (dd, J=7.5 and 6 Hz, 1H: 3 α); 4.76 (broad dd, J=13 and 7.5 Hz, 1H: the other H of the CH$_2$ in 5 ε); 4.84 (mt, 1H: 2 α); 4.89 (dd, J=10 and Hz, 1H: 1α); 5.21(dd, J=12 and 4 Hz, 1H: 4α); 5.28 (broad d, J=6 Hz, 1H: 5 α); 5.88 (d, J=9.5 Hz, 1H: 6 α); 5.91 (mt, 1H: 1 β); 6.48 (d, J=10 Hz, 1H: NH in 2); 6.60 (d, J=8 Hz, 2H: aromatic H in 4 ε); 7.03 (d, J=8 Hz, 2H: aromatic H in 4 δ); from 7.10 to 7.35 (mt, 5H: aromatic H in 6); 7.47 (limiting AB, 2H: 1'H$_4$ and 1'H$_5$); 7.89 (mt, 1H: 1'H$_6$); 8.42 (d, J=10 Hz, 1H: NH in 1); 8.76 (d, J=9.5 Hz, 1H: NH in 6); 11.62 (s, 1H: OH).

EXAMPLE 23

Preparation of the 4ζ-trifluoro-methoxy-de(4ζ-dimethylamino)pristinamycin I$_A$

Strain SP92::pVRC508 is cultured in production medium using 60 erlenmeyer flasks, as described in Example 3, with 1 ml of a 20 g/l solution of (R,S)-4-O-trifluoromethyltyrosine hydrochloride, synthesized as in Example 34-8, in water being added at 16 h. At the end of 40 h of culture, the 1.8 liters of must recovered from the 60 erlenmeyer flasks is extracted with 2 volumes of a mixture consisting of 66% 100 mM phosphate buffer, pH 2.9, and 34% acetonitrile, and then centrifuged. The supernatant is extracted with 2 times [lacuna] volumes of dichloromethane. The chloromethylene phases are washed with water and then combined, dried over sodium sulphate and evaporated. The dry extract is taken up in [lacuna] ml of dichloromethane and injected onto a silica (30 g) column which is mounted in dichloromethane and eluted successively with plateaus of from 0 to 10% methanol in dichloromethane. The fractions containing 4ζ-trifluoromethoxy-de(4ζ-dimethylamino) pristinamycin I$_A$ are combined and evaporated. The dry residue is taken up in 7 ml of a mixture consisting of 60% of water and 40% acetonitrile and injected in two portions onto a semi-preparative Nucleosil 7µ C8 10×250 mm (Macherey Nagel) column, which is eluted with a mixture consisting of 60% 100 mM phosphate buffer, pH 2.9, and 40% of acetonitrile. The fractions containing 4ζ-trifluoromethoxy-de(4ζ-dimethylamino)pristinamycin I$_A$ are combined and extracted with one volume of dichloromethane. The organic phase is washed with water, dried over sodium sulphate and then evaporated. 46.5 mg of 4ζ-trifluoromethoxy-de(4ζ-dimethylamino)pristinamycin I$_A$ are obtained.

NMR spectrum. $^1$H (400 MHz, CDCl$_3$, δ in ppm, ref. TMS): 0.77 (dd, J=16 and 5.5 Hz, 1H: 1H of the CH$_2$ in 5 β); 0.92 (t, J=7.5 Hz, 3H: CH$_3$ in 2 γ); 1.08 (mt, 1H: 1H of the CH$_2$ in 3 β); from 1.30 to 1.40 (mt, 1H: 1H of the CH$_2$ in 3 γ); 1.33 (d, J=7 Hz, 3H: CH$_3$ in 1 γ); from 1.55 to 1.70 (mt, 1H: the other H of the CH$_2$ in 3 γ); 1.65 and 1.76 (2 mts, 1H each: CH$_2$ in 2 β); 2.02 (mt, 1H: the other H of the CH$_2$ in 3 β); 2.11 and 2.40 (respectively, mt and broad d, J=16.5 Hz, 1H each: CH$_2$ in 5 δ); 2.54 (d, J=16 Hz, 1H: the other H of the CH$_2$ in 5 β); 2.88 (dt, J=13 and 4 Hz, 1H: 1H of the CH$_2$ in 5 ε); 3.08 (dd, J=12 and 5 Hz, 1H: 1H of the CH$_2$ in 4 β); 3.22 (s, 3H: NCH$_3$); from 3.30 to 3.45 (mt, 1H: 1H of the CH$_2$ in 3 δ); 3.39 (t, J=12 Hz, 1H: the other H of the CH$_2$ in 4 β); 3.59 (mt, 1H: the other H of the CH$_2$ in 3 δ); 4.53 (t, J=7.5 Hz, 1H: 3 α); 4.75 (broad dd, J=13 and 8 Hz, 1H: the other H of the CH$_2$ in 5 ε); 4.85 (mt, 1H: 2 α); 4.89 (dd, J=10 and 1.5 Hz, 1H: 1 α); 5.35 (broad d, J=5.5 Hz, 1H: 5 α); 5.41 (dd, J=12 and 5 Hz, 1H: 4 α); 5.92 (d, J=10 Hz, 1H: 6 α); 5.93 (mt, 1H: 1 β); 6.53 (d, J=9.5 Hz, 1H: NH in 2); from 7.15 to 7.35 (mt, 5H: aromatic H in 6); 7.16 (d, J=8 Hz, 2H: aromatic H in 4 ε); 7.26 (d, J=8 Hz, 2H: aromatic H in 4 δ); 7.37 (dd, J=8.5 and 4 Hz, 1H: 1'H$_5$); 7.42 (dd, J=8.5 and 1.5 Hz, 1H: 1'H$_4$); 7.70 (dd, J=4 and 1.5 Hz, 1H: 1'H$_6$); 8.37 (d, J=10 Hz, 1H: NH in 1); 8.75 (d, J=10 Hz, 1H: NH in 6); 11.66 (s, 1H: OH).

EXAMPLE 24

Preparation of 4ζ-allyloxy-de(4ζ-dimethylamino) pristinamycin I$_A$

Strain SP92::pVRC508 is cultured in production medium using 90 erlenmeyer flasks, as described in Example 3, with 1 ml of a 20 g/l solution of (S)-4-O-allyltyrosine hydrochloride, synthesized as in Example 33, in 0.1N hydrochloric acid being added at 16 h. At the end of 40 h of culture, the 2.7 liters of must recovered from the 90 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-allyloxy-de(4ζ-dimethylamino)pristinamycin I$_A$ are combined and evaporated. The dry residue is taken up in 7 ml of a mixture consisting of 60% of water and 40% acetonitrile and injected onto a semi-preparative Nucleosil 7µ C8 10×250 mm (Macherey Nagel) column, which is eluted with a mixture consisting of 52% 100 mM phosphate buffer, pH 2.9, and 48% of acetonitrile. The fractions containing 4ζ-allyloxy-de(4ζ-dimethylamino)pristinamycin I$_A$ are combined and extracted with one volume of dichloromethane. The organic phase is washed with water, dried over sodium sulphate and then evaporated. 29 mg of 4ζ-allyloxy-de(4ζ-dimethylamino)pristinamycin I$_A$ are obtained.

NMR spectrum. $^1$H (400 MHz, CDCl$_3$, δ in ppm, ref. TMS):0.63 (dd, J=16 and 6 Hz, 1H: 1H of CH$_2$ in 5 β); 0.91 (t, J=7.5 Hz, 3H: CH$_3$ in 2 γ); 1.13 (mt, 1H: 1H of CH$_2$ in 3 β); 1.29 (mt, 1H: 1H of CH$_2$ in 3 γ); 1.33 (d, J=6.5 Hz, 3H: CH$_3$ in 1 γ); 1.57 (mt, 1H: the other H of the CH$_2$ in 3 γ); 1.65 and 1.74 (2 mts, 1H each: CH$_2$ in 2 β); 2.02 (mt, 1H: the other H of the 3 CH$_2$ in 3 β); 2.14 and 2.34 (respectively, mt and broad d, J=16.5 Hz, 1H each: CH$_2$ in 5 δ); 2.43 (d, J=16 Hz, 1H: the other H of the CH$_2$ in 5 β); 2.85 (dt, J=13 and 4 Hz, 1 H: 1H of the CH$_2$ in 5 ε); 2.95 (dd, J=12 and 4 Hz, 1H: 1H of the CH$_2$ in 4 β); 3.25 (s, 3H: NCH$_3$); 3.33 (mt, 1H: 1H of the CH$_2$ in 3 δ): 3.36 (t, J=12 Hz, 1H: the other H of the CH$_2$ in 4 β); 3.56 (mt, 1H: the other H of the CH$_2$ in 3 δ); 4.51 (limiting AB, 2H: OCH$_2$ of the allyl); 4.56 (t, J=7.5 Hz, 1H: 3 α); 4.75 (broad dd, J=13 and 8 Hz, 1H: the other H of the CH$_2$ in 5 ε); 4.84 (mt, 1H: 2 α); 4.88 (dd, J=10 and 1 Hz, 1H: 1 α); 5.27 (dd, J=12 and 4 Hz, 1H: 4 α); 5.32 (broad d, J=6 Hz, 1H: 5 α); 5.30 and 5.40 (respectively, mt and dd, J=17 and 1.5 Hz, 1H each: =CH$_2$ of the allyl); 5.89 (d, J=9.5 Hz, 1H: 6 α); 5.91 (mt, 1H: 1 β); 6.02 (mt, 1H: CH= of the allyl); 6.50 (d, J=10 Hz, 1H: NH in 2); 6.85 (d, J=8 Hz, 2H: aromatic H in 4 ε); 7.12 (d, J=8 Hz, 2H: aromatic H in 4 δ); from 7.10 to 7.35 (mt, 5H: aromatic H in 6); 7.45 (dd, J=8.5 and 1.5 Hz, 1H: 1'H$_4$); 7.57 (dd, J=8.5 and 4 Hz, 1H: 1'H$_5$); 7.77 (dd, J=4 and 1.5 Hz, 1H: 1'H$_6$); 8.41 (d, J=10 Hz, 1H: NH in 1); 8.74 (d, J=9.5 Hz, 1H: NH in 6); 11.63 (s, 1H: OH).

EXAMPLE 25

Preparation of 4ζ-ethoxy-de(4ζ-dimethylamino) pristinamycin I$_A$

Strain SP92::pVRC508 is cultured in production medium using 90 erlenmeyer flasks, as described in Example 3, with 1 ml of a 20 g/l solution of (S)-4-O-ethyltyrosine hydrochloride, synthesized as in Example 33, in 0.1N hydrochloric acid being added at 16 h. At the end of 40 h of culture, the 2.7 liters of must recovered from the 90 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-ethoxy-de(4ζ-dimethylamino)pristinamycin I$_A$ are combined and evaporated. The dry residue is taken up in 7 ml of a mixture consisting of 60% of water and 40% acetonitrile and injected onto a semi-preparative Nucleosil 7μ C8 10×250 mm (Macherey Nagel) column, which is eluted with a mixture consisting of 52% 100 mM phosphate buffer, pH 2.9, and 48% of acetonitrile. The fractions containing 4ζ-ethoxy-de(4ζ-dimethylamino)pristinamycin I$_A$ are combined and extracted with one volume of dichloromethane. The organic phase is washed with water, dried over sodium sulphate and then evaporated. 29 mg of 4ζ-ethoxy-de(4ζ-dimethylamino)pristinamycin I$_A$ are obtained.

NMR spectrum. $^1$H (400 MHz, CDCl$_3$, δ in ppm, ref. TMS): 0.64 (dd, J=16 and 5.5 Hz, 1H: 1H of the CH$_2$ in 5 β); 0.90 (t, J=7.5 Hz, 3H: CH$_3$ in 2 γ); 1.12 (mt, 1H: 1H of the CH$_2$ in 3 β); 1.25 (mt, 1H: 1H of the CH$_2$ in 3 γ); 1.33 (d, J=7 Hz, 3H: CH$_3$ in 1 γ); 1.42 (t, J=7 Hz, 3H: CH$_3$ of the ethyl); 1.57 (mt, 1H: the other H of the CH$_2$ in 3 γ); 1.63 and 1.74 (2 mts, 1H each: CH$_2$ in 2 β); 2.02 (mt, 1H: the other H of the CH$_2$ in 3 β); 2.16 and 2.35 (respectively mt and broad d, J=16.5 Hz, 1H each: CH$_2$ in 5 δ); 2.43 (d, J=16 Hz, 1H: the other H of the CH$_2$ in 5 β); 2.83 (dt, J=13 and 4 Hz, 1H: 1H of the CH$_2$ in 5 ε); 2.93 (dd, J=12 and 4 Hz, 1H: 1H of the CH$_2$ in 4 β); from 3.15 to 3.30 (mt, 1H: 1H of the CH$_2$ in 3 δ); 3.24 (s, 3H: NCH$_3$); 3.35 (t, J=12 Hz, 1H: the other H of the CH$_2$ in 4 β); 3.55 (mt, 1H: the other H of the CH$_2$ in 3 δ); 3.95 (limiting AB, 2H: OCH$_2$ of the ethyl); 4.56 (dd, J=7.5 and 6 Hz, 1H: 3 α); 4.75 (broad dd, J=13 and 8 Hz, 1H: the other H of the CH$_2$ in 5 ε); 4.84 (mt, 1H: 2 α); 4.87 (dd, J=10 and 1 Hz, 1H: 1 α); 5.26 (dd, J=12 and 4 Hz, 1H: 4 α); 5.32 (broad d, J=5.5 Hz, 1H: 5 α); 5.88 (d, J=10 Hz, 1H: 6 α); 5.92 (mt, 1H: 1 β); 6.48 (d, J=10 Hz, 1H: NH in 2); 6.83 (d, J=8 Hz, 2H: aromatic H in 4 ε); 7.10 (d, J=8 Hz, 2H: aromatic H in 4 δ); from 7.10 to 7.35 (mt, 5H: aromatic H in 6); 7.44 (dd, J=8.5 and 1.5 Hz, 1H: 1'H$_4$); 7.57 (dd, J=8.5 and 4.5 Hz, 1H: 1'H$_5$); 7.77 (dd, J=4.5 and 1.5 Hz, 1H: 1'H$_6$); 8.38 (d, J=10 Hz, 1H: NH in 1); 8.75 (d, J=10 Hz, 1H: NH in 6); 11.60 (s, 1H: OH).

EXAMPLE 26

Preparation of 4ζ-(2-chloro-ethoxy)-de(4ζ-dimethylamino)pristinamycin I$_A$

Strain SP92::pVRC508 is cultured in production medium using 60 erlenmeyer flasks, as described in Example 3, with 1 ml of a 20 g/l solution of (S)-4-O-(2-chloroethyl)tyrosine hydrochloride, synthesized as in Example 42-1, in water being added at 16 h. At the end of 40 h of culture, the 1.8 liters of must recovered from the 60 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-(2-chloroethoxy)-de(4ζ-dimethylamino)pristinamycin I$_A$ are combined and evaporated. The dry residue is taken up in 7 ml of a mixture consisting of 60% of water and 40% acetonitrile and injected onto a semi-preparative Nucleosil 7μ C8 10×250 mm (Macherey Nagel) column, which is eluted with a mixture consisting of 60% 100 mM phosphate buffer, pH 2.9, and 40% of acetonitrile. The fractions containing 4ζ-(2-chloroethoxy)-de(4ζ-dimethylamino) pristinamycin I$_A$ are combined and extracted with one volume of dichloromethane. The organic phase is washed with water, dried over sodium sulphate and then evaporated. 3.2 mg of 4ζ-(2-chloroethoxy)-de(4ζ-dimethylamino) pristinamycin I$_A$ are obtained.

NMR spectrum. $^1$H (400 MHz, CDCl$_3$, δ in ppm, ref. TMS): 0.66 (dd, J=16 and 5.5 Hz, 1H: 1H of the CH$_2$ in 5); 0.91 (t, J=7.5 Hz, 3H: CH$_3$ in 2 γ); 1.13 (mt, 1H: 1H of the CH$_2$ in 3 β); 1.28 (mt, 1H: 1H of the CH$_2$ in 3 γ); 1.33 (d, J=7 Hz, 3H: CH$_3$ in 1 γ); 1.57 (mt, 1H: the other H of the CH$_2$ in 3 γ); 1.66 and 1.76 (2 mts, 1H each: CH$_2$ in 2 β); 2.02 (mt, 1H: the other H of the CH$_2$ in 3 β); 2.16 and 2.37 (respectively, mt and broad d, J=16.5 Hz, 1H each: CH$_2$ in 5 δ); 2.47 (d, J=16 Hz, 1H: the other H of the CH$_2$ in 5 β); 2.86 (dt, J=13 and 4 Hz, 1H: 1H of the CH$_2$ in 5 ε); 2.95 (dd, J=12 and 4 Hz, 1H: 1H of the CH$_2$ in 4 β); 3.23 (s, 3H: NCH$_3$); 3.32 (mt, 1H: 1H of the CH$_2$ in 3 δ); 3.37 (t, J=12 Hz, 1H: the other H of the CH$_2$ in 4 β); 3.57 (mt, 1H: the other H of the CH$_2$ in 3 δ); 3.82 (t, J=6 Hz, 2H: CH$_2$Cl); 4.19 (limiting AB, 2H: OCH$_2$ of the ethyl); 4.55 (dd, J=7.5 and 7 Hz, 1H: 3 α); 4.75 (broad dd, J=13 and 8 Hz, 1H: the other H of the CH$_2$ in 5 ε); 4.84 (mt, 1H: 2 α); 4.87 (broad d, J=10 Hz, 1H: 1 α); 5.28 (dd, J=12 and 4 Hz, 1H: 4 α); 5.32 (broad d, J=5.5 Hz, 1H: 5 α); 5.88 (d, J=10 Hz, 1H: 6α); 5.90 (mt, 1H: 1 β); 6.50 (d, J 10 Hz, 1H: NH in 2); 6.86 (d, J=8 Hz, 2H: aromatic H in 4 ε); 7.13 (d, J=8 Hz, 2H: aromatic H in 4 δ); from 7.10 to 7.35 (mt, 5H: aromatic H in 6); 7.45 (limiting AB, 2H: 1'H$_4$ and 1'H$_5$); 7.75 (dd, J=4 and 2 Hz, 1H: 1'H$_6$); 8.38 (d, J=10 Hz, 1H: NH in 1); 8.74 (d, J=10 Hz, 1H: NH in 6); 11.62 (s, 1H: OH).

EXAMPLE 27

Preparation of 4ζ-acetyl-de 4ζ-dimethylamino) pristinamycin I$_A$

Strain SP92::pVRC508 is cultured in production medium using 60 erlenmeyer flasks, as described in Example 3, with 1 ml of a 20 g/l solution of (S)-4-acetylphenylalanine, synthesized as in Example 33, in 0.1N sodium hydroxide solution being added at 16 h. At the end of 40 h of culture, the 1.8 liters of must recovered from the 60 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-acetyl)-de(4ζ-dimethylamino)pristinamycin $I_A$ are combined and evaporated. The dry residue is taken up in 7 ml of a mixture consisting of 60% of water and 40% acetonitrile and injected onto a semi-preparative Nucleosil 7μ C8 10×250 mm (Macherey Nagel) column, which is eluted with a mixture consisting of 60% 100 mM phosphate buffer, pH 2.9, and 40% of acetonitrile. The fractions containing 4ζ-acetyl-de(4ζ-dimethylamino)pristinamycin $I_A$ are combined and extracted with one volume of dichloromethane. The organic phase is washed with water, dried over sodium sulphate and then evaporated. 4.2 mg of 4ζ-acetyl-de(4ζ-dimethylamino)pristinamycin $I_A$ are obtained.

NMR spectrum. $^1$H (400 MHz, CDCl$_3$, δ in ppm, ref. TMS): 0.73 (dd, J=16 and 6 Hz, 1H: 1H of the CH$_2$ in 5 β); 0.93 (t, J=7.5 Hz, 3H: CH$_3$ in 2 γ); 1.12 (mt, 1H: 1H of the CH$_2$ in 3 β); from 1.25 to 1.45 (mt, 1H: 1H of the CH$_2$ in 3 γ); 1.33 (d, J=7 Hz, 3H: CH$_3$ in 1 γ); 1.62 (mt, 1H: the other H of the CH$_2$ in 3 γ); from 1.60 to 1.85 (mt, 2H: CH$_2$ in 2 β); 2.02 (mt, 1H: the other H of the CH$_2$ in 3 β); 2.20 and 2.42 (respectively, mt and broad d, J=16.5 Hz, 1H each: CH$_2$ in 5 δ); 2.52 (d, J=16 Hz, 1H: the other H of the CH$_2$ in 5 β); 2.60 (s, 3H: ArCOCH$_3$); 2.88 (dt, J=13 and 4.5 Hz, 1H: 1H of CH$_2$ in 5 ε); 3.13 (dd, J=13.5 and 5.5 Hz, 1H: 1H of the CH$_2$ in 4 β); 3.21 (s, 3H: NCH$_3$); from 3.30 to 3.50 (mt, 1H: the other H of the CH$_2$ in 4 β); from 3.30 to 3.50 and 3.63 (2 mts, 1H each: CH$_2$ in 3 δ); 4.53 (t, J=7.5 Hz, 1H: 3 α); 4.75 (broad dd, J=13 and 8 Hz, 1H: the other H of the CH$_2$ in 5 ε); 4.84 (mt, 1H: 2 α); 4.88 (dd, J=10 and 1 Hz, 1H: 1 α); 5.35 (broad d, J=6 Hz, 1H: 5 α); 5.43 (dd, J=10.5 and 4 Hz, 1H: 4 α); 5.90 (d, J 9.5 Hz , 1H: 6 α); 5.92 (mt, 1H: 1 β); 6.56 (d, J=9.5 Hz, 1H: NH in 2); from 7.10 to 7.35 (mt, 5H: aromatic H in 6); 7.28 (d, J=8 Hz, 2H: aromatic H in 4 β); 7.38 (dd, J=8.5 and 2 Hz, 1H: 1'H$_4$); 7.42 (dd, J=8.5 and 4.5 Hz, 1H: 1'H$_5$); 7.66 (dd, J=4.5 and 2 Hz, 1H: 1'H$_6$); 7.88 (d, J=8 Hz, 2H: aromatic H in 4 ε); 8.38 (d, J=10 Hz, 1H: NH in 1); 8.74 (d, J=9.59 Hz, 1H: NH in 6); 11.65 (s, 1H: OH).

EXAMPLE 28

Preparation of 4ε-dimethylamino-de(4ζ-dimethylamino)pristinamycin $I_A$

Strain SP92::pVRC508 is cultured in production medium using 60 erlenmeyer flasks, as described in Example 3, with 1 ml of a 20 g/l solution of (R,S)-3-dimethylaminophenylalanine dihydrochloride, synthesized as in Example 35-10, in 0.1N sodium hydroxide solution being added at 16 h. At the end of 40 h of culture, the 1.8 liters of must recovered from the 60 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ε-dimethylamino-de(4ζ-dimethylamino)pristinamycin $I_A$ are combined and evaporated. The dry residue is taken up in 3 ml of a mixture consisting of 60% of water and 40% acetonitrile and injected onto a semi-preparative Nucleosil 7μ C8 10×250 mm (Macherey Nagel) column, which is eluted with a mixture consisting of 57% 100 mM phosphate buffer, pH 2.9, and 43% of acetonitrile. The fractions containing 4ε-dimethylamino-de(4ζ-dimethylamino) pristinamycin $I_A$ are combined and extracted with one volume of dichloromethane. The organic phase is washed with water, dried over sodium sulphate and then evaporated. 1.1 mg of 4ε-dimethylamino-de(4ζ-dimethylamino) pristinamycin $I_A$ are obtained.

NMR spectrum. $^1$H (400 MHz, CDCl$_3$, δ in ppm, ref TMS): 0.63 (dd, J=16 and 5 Hz, 1H: 1H of the CH$_2$ in 5 β); 0.91 (t, J=7.5 Hz, 3H: CH$_3$ in 2 γ); 1.13 (mt, 1H: 1H of the CH$_2$ in 3 β); from 1.20 to 1.35 (mt, 1H: 1H of the CH$_2$ in 3 γ); 1.32 (d, J=6.5 Hz, 3H: CH$_3$ in 1 γ); 1.57 (mt, 1H: the other H of the CH$_2$ in 3 γ); 1.63 and 1.76 (2 mts, 1H each: CH$_2$ in 2 β); 2.02 (mt, 1H: the other H of the CH$_2$ in 3 β); 2.08 and 2.31 (respectively, mt and broad d, J=16.5 Hz, 1H each: CH$_2$ in 5 δ): 2.35 (d, J=16 Hz, 1H: the other H of the CH$_2$ in 5 β); 2.81 (dt, J=13 and 4 Hz, 1H: 1H of the CH$_2$ in 5 ε); 2.90 (s, 6H: N(CH$_3$)2); 2.97 (dd, J=12 and 4 Hz, 1H: 1H of the CH$_2$ in 4 β); from 3.20 to 3.30 (mt, 1H: 1H of the CH$_2$ in 3 δ); 3.28 (s, 3H: NCH$_3$); 3.37 (t, J=12 Hz, 1H: the other H of the CH$_2$ in 4 β); 3.57 (mt, 1H: the other H of the CH$_2$ in 3 δ); 4.58 (t, J=7.5 Hz, 1H: 3 α); 4.74 (broad dd, J=13 and 8 Hz, 1H: the other H of the CH$_2$ in 5 ε); 4.86 (mt, 1H: 2 α); 4.89 (broad d, J=10 Hz, 1H: 1 α); 5.27 (dd, J=12 and 4 Hz, 1H: 4 α); 5.29 (broad d, J=5 Hz, 1H: 5 α); 5.89 (d, J=9.5 Hz, 1H: 6 α); 5.90 (mt, 1H: 1 β); 6.50 (d, J=10 Hz, 1H: NH in 2); from 6.50 to 6.70 (mt, 3H: aromatic Hs in the ortho and in the para positions with respect to the dimethylamino); from 7.15 to 7.35 (mt, 5H: aromatic Hs in 6); 7.20 (t, J=8 Hz, 1H: aromatic H in the meta position with respect to the dimethylamino); 7.43 (limiting AB, 2H: 1'H$_4$ and 1'H$_5$); 7.82 (mt, 1H: 1'H$_6$); 8.38 (d, J=10 Hz, 1H: NH in 1); 8.73 (d, J=9.5 Hz, 1H: NH in 6); 11.61 (s, 1H: OH).

EXAMPLE 29

Preparation of 4ε-methylthio-de(4ζ-dimethylamino) pristinamycin $I_A$

Strain SP92::pVRC508 is cultured in production medium using 56 erlenmeyer flasks, as described in Example 3, with 1 ml of a 20 g/l solution of (R,S)-3-methylthiophenylalanine hydrochloride, synthesized as in Example 34-11, in 0.1N sodium hydroxide solution being added at 16 h. At the end of 40 h of culture, the 1.68 liters of must recovered from the 56 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the novel derivative of pristinamycin $I_A$ are combined and evaporated. The dry residue is taken up in 7 ml of a mixture consisting of 54% of water and 46% acetonitrile and injected onto a semi-preparative Nucleosil 7μ C8 10×250 mm (Macherey Nagel) column, which is eluted with a mixture consisting of 55% 100 mM phosphate buffer, pH 2.9, and 45% of acetonitrile. The fractions containing the novel pristinamycin are combined and extracted with one volume of dichloromethane. The organic phase is washed with water, dried over sodium sulphate and then evaporated. 20 mg of 4ε-methylthio-de(4ζ-dimethylamino)pristinamycin $I_A$ are obtained.

NMR spectrum. $^1$H (400 MHz, CDCl3, δ in ppm, ref. TMS): 0.56 (dd, J=16 and 5.5 Hz, 1H: 1H of the CH$_2$ in 5 β); 0.90 (t, J=7.5 Hz, 3H: CH$_3$ in 2 γ); 1.13 (mt, 1H: 1H of the CH$_2$ in 3 β); 1.28 (mt, 1H: 1H of the CH$_2$ in 3 γ); 1.32 (d, J=6.5 Hz, 3H: CH$_3$ in 1 γ); 1.58 (mt, 1H: the other H of the CH$_2$ in 3 γ); 1.62 and 1.74 (2 mts, 1H each: CH$_2$ in 2 β); 2.02 (mt, 1H: the other H of the CH$_2$ in 3 β); 2.25 and 2.35 (respectively, mt and broad d, J=16.5 Hz, 1H each: CH$_2$ in 5 δ); 2.39 (d, J=16 Hz, 1H: the other H of the CH$_2$ in 5 β); 2.43 (s, 3H: SCH$_3$); 2.82 (dt, J=13 and 4 Hz, 1H: 1H of the CH$_2$ in 5 ε); 2.98 (dd, J=12 and 4.5 Hz, 1H: 1H of the CH$_2$ in 4 β) 3.26 (s, 3H: NCH$_3$); 3.30 (t, J=12 Hz 1H: 1H of CH$_2$ in 3 δ); 3.38 (mt, 1H: the other H of the CH$_2$ in 4 β); 3.57 (mt, 1H: the other H of the CH$_2$ in 3 δ); 4.56 (t, J=7.5 Hz, 1H: 3 α); 4.74 (broad dd, J=13 and 8 Hz, 1H: the other H of the CH$_2$ in 5 ε); 4.84 (mt, 1H: 2 α); 4.89 (dd, J=10 and 1 Hz, 1H: 1 α); 5.29 (dd, J=12 and 4.5 Hz, 1H: 4 α); 5.32 (broad d, J=5.5 Hz, 1H: 5 α); 5.88 (d, J=9.5 Hz, 1H: 6 α); 5.90 (mt, 1H: 1 β); 6.51 (d, J=10 Hz, 1H: NH in 2); 6.99 (broad d, J=8 Hz, 1H: aromatic H in the para position with respect to the methylthio); 7.10 and 7.15 (respectively, broad s and broad d, J=8 Hz, 1H each: aromatic Hs in the ortho position with respect to the methylthio); from 7.15 to 7.35 (mt, 6H: aromatic Hs in 6 and aromatic Hs in the meta position with respect to the methylthio); 7.43 (broad d, J=8 Hz, 1H: 1'H$_4$); 7.52 (dd, J=8 and 4 Hz, 1H: 1'H$_5$); 7.79 (broad d, J=4 Hz, 1H: 1'H$_6$); 8.38 (d, J=10 Hz, 1H: NH in 1); 8.73 (d, J=9.5 Hz, 1H: NH in 6); 11.62 (s, 1H: OH).

EXAMPLE 30

Preparation of 4ε-ethoxy-de(4ζ-dimethylamino)pristinamycin $I_A$

Strain SP92::pVRC508 is cultured in production medium using 60 erlenmeyer flasks, as described in Example 3, with 1 ml of a 20 g/l solution of (S)3-O-ethyltyrosine hydrochloride, synthesized as in Example 37-1, in 0.2N sodium hydroxide solution being added at 16 h. At the end of 40 h of culture, the 1.8 liters of must recovered from the 60 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing the novel derivative of pristinamycin $I_A$ are combined and evaporated. 19 mg of dry residue are obtained. The latter is taken up in 3 ml of a mixture consisting of 60% of water and 40% acetonitrile and injected onto a semi-preparative Nucleosil 7μ C8 10×250 mm (Macherey Nagel) column, which is eluted with a mixture consisting of 60% 100 mM phosphate buffer, pH 2.9, and 40% of acetonitrile. The fractions containing the novel pristinamycin are combined and extracted with one volume of dichloromethane. The organic phase is washed with water, dried over sodium sulphate and then evaporated. 15.8 mg of 4ε-O-ethoxy-de(4ζ-dimethylamino)pristinamycin $I_A$ are obtained.

NMR spectrum. $^1$H (400 MHz, CDCl$_3$, δ in ppm, ref TMS): 0.55 (dd, J=16 and 5.5 Hz, 1H: 1H of the CH$_2$ in 5 β); 0.90 (t, J=7.5 Hz, 3H: CH$_3$ in 2 γ); 1.12 (mt, 1H: 1H of the CH$_2$ in 3 β); 1.20 (mt, 1H: 1H of the CH$_2$ in 3 γ); 1.31 (d, J=6.5 Hz, 3H: CH$_3$ in 1 γ); 1.49 (t, J=7 Hz, 3H: CH$_3$ of the ethyl); 1.54 (mt, 1H: the other H of the CH$_2$ in 3 β); 1.63 and 1.73 (2 mts, 1H each: CH$_2$ in 2 β); 2.02 (mt, 1H: the other H of the CH$_2$ in 3 β); 2.22 and 2.33 (respectively, mt and broad d, J=16.5 Hz, 1H each: CH$_2$ in 5 δ); 2.46 (d, J=16 Hz, 1H: the other H of the CH$_2$ in 5 β); 2.83 (dt, J=13 and 4 Hz, 1H: 1H of the CH$_2$ in 5 ε); 2.95 (dd, J=12 and 4 Hz, 1H: 1H of the CH$_2$ in 4 β); 3.22 (mt, 1H: 1H of the CH$_2$ in 3 δ); 3.27 (s, 3H: NCH$_3$); 3.39 (t, J=12 Hz, 1H: the other H of the CH$_2$ in 4 β); 3.53 (mt, 1H: the other H of the CH$_2$ in 3 δ); 3.93 and 4.03 (2 mts, 1H each: OCH$_2$ of the ethyl); 4.56 (dd, J=7 and 5.5 Hz, 1H: 3 α); 4.75 (broad dd, J=13 and 8 Hz, 1H: the other H of the CH$_2$ in 5 ε); 4.82 (mt, 1H: 2 α); 4.88 (dd, J=10 and 1 Hz, 1H: 1 α); 5.23 (dd, J=12 and 4 Hz, 1H: 4 α); 5.23 (broad d, J=5.5 Hz, 1H: 5 α); 5.87 (d, J=9.5 Hz, 1H: 6 α); 5.92 (mt, 1H: 1 β); 6.47 (d, J=10 Hz, 1H: NH in 2); 6.80 (mt, 3H: aromatic H in the ortho and in the para positions with respect to the ethoxy); from 7.10 to 7.35 (mt, 6H: (aromatic Hs in 6 and aromatic Hs in the meta position with respect to the ethoxy); 7.43 (dd, J=8 and 1 Hz, 1H: 1'H$_4$); 7.50 (dd, J=8 and 4 Hz, 1H: 1'H$_5$); 7.77 (dd, J=4 and 1 Hz, 1H: 1'H$_6$); 8.38 (d, J=10 Hz, 1H: NH in 1); 8.70 (d, J=9.5 Hz, 1H: NH in 6); 11.60 (s, 1H: OH).

EXAMPLE 31

Preparation of 4ζ-ethylthio-de (4ζ-dimethylamino)pristinamycin $I_A$

Strain SP92::pVRC508 is cultured in production medium using 2 erlenmeyer flasks, as described in Example 3, with 1 ml of a 20 g/l solution of (S)-4-ethylthiophenylalanine hydrochloride, synthesized as in Example 33, in 0.1N sodium hydroxide solution being added at 16 h. At the end of 40 h of culture, the 60 ml of must recovered from the 2 erlenmeyer flasks is extracted with 2 volumes of a mixture consisting of 66% 100 mM phosphate buffer, pH 2.9, and 34% acetonitrile, and then centrifuged. The supernatant is extracted with 2 times 0.5 volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-ethylthio-de(4ζ-dimethylamino)pristinamycin $I_A$ are combined and evaporated. The dry residue is taken up in 7 ml of a mixture consisting of 60% of water and 40% acetonitrile and injected onto a semi-preparative Nucleosil 7μ C8 10×250 mm (Macherey Nagel) column, which is eluted with a mixture consisting of 52% 100 mM phosphate buffer, pH 2.9, and 48% of acetonitrile. The fractions containing 4ζ-ethylthio-de(4ζ-dimethylamino)pristinamycin $I_A$ are combined and extracted with one volume of dichloromethane. The organic phase is washed with water, dried over sodium sulphate and then evaporated. ? mg of 4ζ-ethylthio-de(4ζ-dimethylamino)pristinamycin $I_A$ are obtained.

NMR spectrum. $^1$H (400 MHz, CDCl$_3$, δ in ppm): 0.68 (dd, J=16 and 6 Hz, 1H: 1H of the CH$_2$ in 5 β); 0.92 (t, J=7.5 Hz, 3H: CH$_3$ in 2 γ); from 1.10 to 1.40 (mt, 5H: 1H of the CH$_2$ in 3 β and 1H of the CH$_2$ in 3 γ and CH$_3$ of the ethyl); 1.32 (d, J=7 Hz, 3H: CH$_3$ in 1 γ); from 1.45 to 1.85 (mt, 3H: the other H of the CH$_2$ in 3 γ and CH$_2$ in 2 β); 2.02 (mt, 1H: the other H of the CH$_2$ in 3 β); 2.18 and 2.37 (respectively, mt and broad d, J=16.5 Hz, 1H each: CH$_2$ in 5 δ); 2.45 (broad d, J=16 Hz, 1H: the other H of the CH$_2$ in 5 β); 2.85 (dt, J=13 and 4 Hz, 1H: 1H of the CH$_2$ in 5 ε); 2.90 (mt, 2H: ArSCH$_2$ ethyl); 2.98 (dd, J=12 and 4 Hz, 1H: 1H of the CH$_2$ in 4 β); 3.25 (s, 3H: NCH$_3$); 3.35 (mt, 1H: 1H of the CH$_2$ in 3 δ); 3.39 (t, J=12 Hz, 1H: the other H of the CH$_2$ in 4 β); 3.57 (mt, 1H: the other H of the CH$_2$ in 3 δ); 4.55 (t, J=7.5 Hz, 1H: 3 α); 4.75 (broad dd, J=13 and 7.5 Hz, 1H,: the other H of the CH$_2$ in 5 ε); 4.85 (mt, 1H: 2 α); 4.89 (dd, J=10 and 1 Hz, 1H: 1 α); from 5.25 to 5.40 (mt, 2H: 5 α and 4 α); 5.88 (d, J=9.5 Hz, 1H: 6 α); 5.91 (mt, 1H: 1 β); 6.55 (d, J=9.5 Hz, 1H: NH in 2); 7.10 (d, J=8 Hz, 2H: aromatic Hs in 4 δ); from 7.10 to 7.35 (mt, 7H: aromatic Hs in 6 and 4 ε); 7.44 (limiting AB, 2H: 1'H$_4$ and 1'H5); 7.74 (mt, 1H: 1'H$_6$); 8.38 (d, J=10 Hz, 1H: NH in 1); 8.75 (d, J=9.5 Hz, 1H: NH in 6); 11.62 (s, 1H: OH).

EXAMPLE 32

Preparation of 4ζ-ethyl-de(4ζ-dimethylamino) pristinamycin I$_A$

Strain SP92::pVRC508 is cultured in production medium using 2 erlenmeyer flasks, as described in Example 3, with 1 ml of a 20 g/l solution of (R,S)-4-ethylphenylalanine, synthesized as in Example 33, in 0.1N sodium hydroxide solution being added at 16 h. At the end of 40 h of culture, the 60 ml of must recovered from the 2 erlenmeyer flasks is extracted with 2 volumes of a mixture consisting of 66% 100 mM phosphate buffer, pH 2.9, and 34% acetonitrile, and then centrifuged. The supernatant is extracted with 2 times [lacuna] volumes of dichloromethane. The chloromethylene phases are washed with water and then combined, dried over sodium sulphate and evaporated. The dry extract is taken up in 20 ml of dichloromethane and injected onto a silica (30 g) column which is mounted in dichloromethane and eluted successively with plateaus of from 0 to 10% methanol in dichloromethane. The fractions containing 4ζ-ethyl-de(4ζ-dimethylamino)pristinamycin I$_A$ are combined and evaporated. The dry residue is taken up in 7 ml of a mixture consisting of 52% of water and 48% acetonitrile and injected onto a semi-preparative Nucleosil 7μ C8 10×250 mm (Macherey Nagel) column, which is eluted with a mixture consisting of 52% 100 mM phosphate buffer, pH 2.9, and 48% of acetonitrile. The fractions containing 4ζ-ethyl-de (4ζ-dimethylamino)pristinamycin I$_A$ are combined and extracted with one volume of dichloromethane. The organic phase is washed with water, dried over sodium sulphate and then evaporated. 0.50 mg of 4ζ-ethyl-de(4ζ-dimethylamino) pristinamycin I$_A$ are obtained.

NMR spectrum. $^1$H (400 MHz, CDCl$_3$, δ in ppm, ref. TMS): 0.42 (dd, J=16 and 5.5 Hz, 1H: 1H of the CH$_2$ in 5 β); 0.92 (t, J=7.5 Hz, 3H: CH$_3$ in 2 γ); from 1.10 to 1.40 (mt, 2H: 1H of the CH$_2$ in 3 β and 1H of the CH$_2$ in 3 γ); 1.23 (t, J=7.5 Hz, 3H: CH$_3$ of the ethyl); 1.35 (d, J=7 Hz, 3H: CH$_3$ in 1 γ); from 1.45 to 1.85 (mt, 3H: the other H of the CH$_2$ in 3 γ and CH$_2$ in 2 β); 2.02 (mt, 1 H: the other H of the CH$_2$ in 3 β); 2.15 and from 2.25 to 2.40)2 mts, 1H each: CH$_2$ in 5 δ); from 2.25 to 2.40 (mt, 1H: the other H of the CH$_2$ in 5 β); 2.60 (q, J=7.5 Hz, 2H: ArCH$_2$ of the ethyl); 2.83 (dt, J=13 and 4 Hz, 1H: 1H of the CH$_2$ in 5 ε); 2.98 (dd, J=12 and 4 Hz, 1H: 1H of the CH$_2$ in 4 β); from 3.25 to 3.35 (mt, 1H: 1H of the CH$_2$ in 3 δ); 3.27 (s, 3H: NCH$_3$); 3.39 (t, J=12 Hz, 1H: the other H of the CH$_2$ in 4 β); 3.59 (mt, 1H: the other H of the CH$_2$ in 3 δ); 4.58 (dd, J=7 and 6.5 Hz, 1H: 3 α); 4.75 (broad dd, J=13 and 8 Hz, 1H: the other H of the CH$_2$ in 5 ε); 4.87 (mt, 1H: 2 α); 4.89 (dd, J=10 and 1 Hz, 1H: 1 α); 5.24 (broad d, J=5.5 Hz, 1H: 5 α); 5.29 (dd, J=12 and 4 Hz, 1H: 4 α); 5.88 (d, J=10 Hz, 1H: 6 α); 5.92 (mt, 1H: 1 β); 6.73 (d, J=10 Hz, 1H: NH in 2); from 7.10 to 7.35 (mt, 9H: aromatic Hs in 6-4 ε and 4 δ); 7.44 (dd, J=8.5 and 1.5 Hz, 1H: 1'H$_4$); 7.50 (dd, J=8.5 and 4.5 Hz, 1H: 1'H$_5$); 7.80 (dd, J=4.5 and 1.5 Hz, 1H: 1'H6); 8.38 (d, J=10 Hz, 1H: NH in 1); 8.75 (d, J=10 Hz, 1H: NH in 6); 11.66 (s, 1H: OH).

Using the same fractions derived from the silica column described above, which fractions also contain the novel pristinamycin I$_H$ derivative, 0.3 mg of ζ-ethyl-de(4ζ-dimethylamino)pristinamycin I$_H$ is isolated by carrying out semi-preparative column chromatography as described above.

NMR spectrum. $^1$H (400 MHz, CDCl$_3$, δ in ppm): 0.04 (mt 1H: 1H of the CH$_2$ in 5 β); 0.92 (t, J=7.5 Hz, 3H: CH$_3$ in 2 γ); from 1.10 to 1.40 (mt, 2H: 1H of the CH$_2$ in 5 δ and 1H of the CH$_2$ in 5 γ); 1.18 (t, J=7.5 Hz, 3H: CH$_3$ of the ethyl); 1.30 (d, J=6.5 Hz, 3H: CH$_3$ in 1 γ); from 1.45 to 1.85 (mt, 7H: the other H of the CH$_2$ in 5 γ- the other H of the CH$_2$ in 5 δ-1H of the CH$_2$ in 3 β-CH$_2$ in 3 γ and CH$_2$ in 2 β); 1.81 (broad d, J=13 Hz, 1H: the other H of the CH$_2$ in 5 β); 2.02 (mt, 1H: the other H of the CH$_2$ in 3 β); 2.40 (dt, J=13 and 4 Hz, 1H: 1H of the CH$_2$ in 5 ε); 2.65 (q, J=7.5 Hz, 2H: ArCH$_2$ of the ethyl); 2.97 and 3.09 (respectively, dd and t, J=12 and 5 Hz and J=12 Hz, 1H each: CH$_2$ in 4 β); 3.50 and 3.60 (2 mts, 1H each: CH$_2$ in 3 δ); 4.13 (dd, J=8 and 5 Hz, 1H: 3 α); 4.49 (broad d, J=13 Hz, 1H: the other H of the CH$_2$ in 5 ε); 4.70 (mt, 2H: 5 α and 4 α); 4.77 (mt, 1H: 2 α); 4.83 (dd, J=10 and 1 Hz, 1H: 1 α); 5.50 (d, J=7 Hz, 1H: 6 α); 5.74 (mt, 1H: 1 β); 6.09 (d, J=4 Hz, 1H: NH in 4); 6.72 (unres. comp., 1H: NH in 2); 7.07 (d, J=8 Hz, 2H: aromatic Hs in 4 ε); 7.15 (d, J=8 Hz, 2H: aromatic Hs in 4 δ); from 7.15 to 7.35 (mt, 5H: aromatic Hs in 6); 7.40 (dd, J=8 and 1 Hz, 1H: 1'H$_4$); 7.45 (dd, J=8 and 4 Hz, 1H: 1'H$_5$); 7.92 (dd, J=4 and 1 Hz, 1H: 1'H6); 8.40 (unres. comp., 1H: NH in 6); 8.50 (d, J=10 Hz, 1H: NH in 1); 11.72 (s, 1H: OH).

EXAMPLE 33

Preparation of Derivatives of Phenylalanine and of Phenylpyruvic Acid which Have Already Been Described Phenylalanine, and its derivatives 4-methoxyphenylalanine, 4-bromophenylalanine, 4-chlorophenylalanine, 4-iodophenylalanine, 4-trifluoromethylphenylalanine, 4-aminophenylalanine and 3-methoxyphenylalanine, which are employed in this work, are commercially available.

The following derivatives of phenylalanine can be prepared in accordance with methods described in the literature.

(RS)-4-dimethylaminophenylalanine

D. F. Elliott, A. T. Fuller, C. R. Harrington, J. Chem. Soc., 1948, 85–89.

(RS)-4-diethylaminophenylalanine

Moldaver B. L., Pushkareva Z. V., Zhur. Obshchei Khim., 31, 1560–1569 (1961); C. A. 1961, 22226f.; J. A. Stock, J. Chem. Soc, 1959, 90–97

(RS)-4-ethylaminophenylalanine

F. Bergel, J. A. Stock, J. Chem. Soc, 1959, 90–97.

(RS)-4-phenylphenylalanine

J. V. Braun, J. Nelles, Berichte, 66B, 1933, 1464–1470.

(RS)-4-methylphenylalanine

R. R., Herr, T. Enjoki, J. P. Dailey, J. Am. Chem. Soc, 1957, 79, 4229–4231.

(RS)-4-methylthiophenylalanine and (R,S)-4-ethylthiophenylalanine

R. L. Colescott, R. R. Herr, J. P. Dailey J. Am. Chem. Soc, 1957, 79, 4232–4235.

(RS)-4-methoxycarbonylphenylalanine

H. Cleland, J. Org. Chem., 1969, 34, 747.

(RS)-2,4-dimethylphenylalanine

R. R., Herr, T. Enjoki, J. P. Dailey, J. Am. Chem. Soc, 1957, 79, 4229–4231.

(RS)-3,4-dimethylphenylalanine

R. R., Herr, T. Enjoki, J. P. Dailey, J. Am. Chem. Soc, 1957, 79, 4229–4231.

(RS)-3-trifluoromethylphenylalanine hydrochloride

R. Filler and H. Novar. J. Org. Chem, 1960, 25, 733–736.

(S)-4-aminomethylphenylalanine

G. E. Stokker, W. F. Hoffman and C. F. Homnick, J. Org. Chem., 1993, 58, 5015–5017.

(R,S)-3-methylphenylalanine

J. H. Burckhalter, V. C. Stephens, J.A.C.S. 1951, 73, 56–58.

(R,S)-4-acetylphenylalanine

J. I. Degaw et al., J. Med.Chem., 1969, 11, 225–227

(S)-4-O-allyltyrosine

A. Loffet, H. Zang, Int. J. Pept. Protein. Res., 1993, 42, 346

(S)-4-O-ethyltyrosine

Y. Sasaki et al., Chem. Pharm. Bull., 1982, 30, 4435

(R,S)-4-ethylphenylalanine

A. Zhuze et al., Coll., Czech. Chem. Comm., 1965, 62, 2648

4-tert-butylphenylpyruvic acid can be prepared in accordance with R. Breslow, J. W. Canary, M. Varney, S. T. Waddell and D. Yang, J. Am. Chem. Soc., 1990, 112, 5212–5219.

The other derivatives of phenylalanine were prepared in accordance with Examples 34 to 42 which are given below. In these examples, flash chromatography was carried out under a mean nitrogen pressure of 50 kPa using a silica of granule size 40–53 μm, in accordance with Still et al., J. Org. Chem., 43, 2923, (1978).

EXAMPLE 34

Preparation of Derivatives of Phenylalanine and of a Derivative of Phenylpyruvic Acid Using Method A

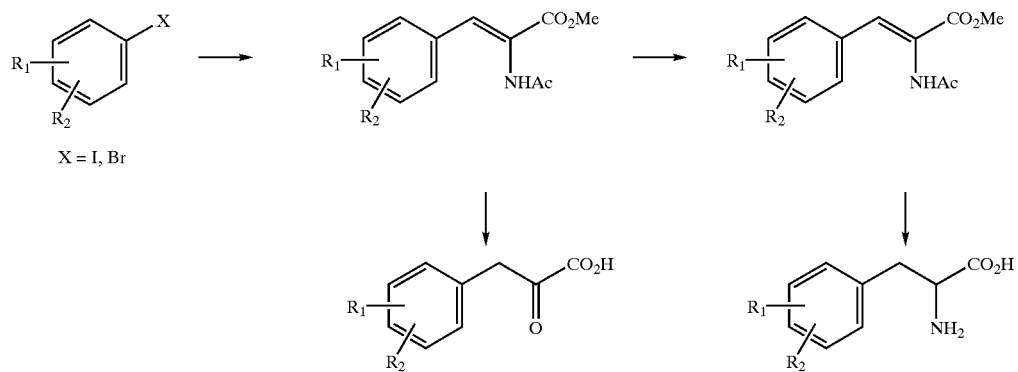

34-1 (RS)-4-methylaminophenylalanine, dihydrochloride 37 ml of 12 N hydrochloric acid are added to 3.70 g of methyl N-acetyl-4-methylaminophenylalaninate, and the mixture is heated to reflux, while stirring, for 8 h. After one night at room temperature, the reaction medium is concentrated to dryness under reduced pressure (50 kPa), and the residue is taken up in a mixture of 50 ml of toluene and 50 ml of ethanol, and this mixture is concentrated once again. After drying in a desiccator under reduced pressure (2.6 kPa), 4.18 g (100%) of (R,S)-4-methylaminophenylalanine dihydrochloride are obtained in the form of a hygroscopic light beige solid which melts at 158° C.

34-2: Methyl (RS)-N-acetyl-4-methylaminophenylalaninate 0.4 g of 10% palladium on charcoal, and then 50 ml of absolute ethanol, are added to 4 g of methyl 4-methylamino-2-acetamidocinnamate which is placed under a nitrogen atmosphere in an autoclave. The mixture is placed under a pressure of 5.5 bar of hydrogen and heated at 50° C. for 15 h with stirring. After stabilizing the temperature at 26° C., and returning the pressure to atmospheric, the medium is filtered through Clarcel®, washed with ethanol and then concentrated to dryness under reduced pressure (2.6 kPa). This results in 3.73 g of methyl N-acetyl-4-methylaminophenylalaninate in the form of white crystals which melt at 118° C.

34-3: Methyl 4-methylamino-2-acetamidocinnamate 5.75 g of methyl 2-acetamidoacrylate, 0.185 g of palladium acetate, 8.1 g of tetrabutylammonium chloride and 6.03 g of sodium hydrogen carbonate are added to a 3-necked flask which is placed under nitrogen, and then 6.5 g of 4-iodo-N-methylalanine, in solution in 200 ml of DMF, are added to this mixture. The mixture is heated at 82° C. for 16 h 30 min and then, after having been cooled down, is poured into 1000 ml of distilled water. The medium is extracted with 250 ml of $CH_2Cl_2$ and the organic phase is separated off; the aqueous phase is then washed twice with 250 ml of $CH_2Cl_2$. The organic phases are combined, dried over sodium sulphate, filtered and concentrated under reduced pressure (50 kPa) at 70° C. to yield a brown oil which is purified by flash chromatography (eluent, AcOEt/cyclohexane and then pure AcOEt).

In this way, 4 g of methyl 4-methylamino-2-acetamidocinnamate is obtained in the form of a yellow solid (Merck Silica 5719, Rf=0.48), which is employed in this form.

N-Methyl-p-iodoanaline can be prepared in accordance with: S. Krishnamurthy, Tetrahedron Letters, 33, 3315–3318, 1982.

34-4: 4-methylaminophenylpyruvic acid 2.4 g of methyl 4-methylamino-2-acetamidocinnamate and 32 ml of 12 N hydrochloric acid are placed in a round-bottomed flask. The mixture is heated to reflux for 3 h and then cooled down and washed twice with 20 ml of diethyl ether. The aqueous phase is cooled down to −10° C. and the precipitate which is obtained is filtered and then rinsed with a minimum of cold hydrochloric acid. The solid which is obtained is dried in a desiccator under reduced pressure in order to yield 1.1 g of 4-methylaminophenylpyruvic acid in the form of a light beige solid which melts at 210° C.

34-5: (R,S)-3-Fluoro-4-methylphenylalanine hydrochloride 0.6 g of (R,S)-3-fluoro-4-methylphenylalanine hydrochloride is obtained in the form of white crystals which melt at a temperature greater than 260° C. by proceeding as in Example 34-1 but using 1.6 g of methyl N-acetyl(3-fluoro-4-methyl)phenylalaninate.

34-6: Methyl (R,S)-N-acetyl-(3-fluoro-4-methyl) phenylalaninate 1.6 g of methyl N-acetyl-(3-fluoro-4-methyl) phenylalaninate are obtained in the form of a colourless oil (Merck Silica 5719, $R_f$=0.46; eluent $CH_2Cl_2$/AcOEt 50/50), by proceeding as in Example 34-2 but using 1.9 g of methyl (4-methyl-3-fluoro)-2-acetamidocinnamate and 0.2 g of 10% palladium on charcoal in 230 ml of ethanol.

34-7: Methyl (3-fluoro-4-methyl)-2-acetamidocinnamate 2.6 g of methyl (3-fluoro-4-methyl)-2-acetamidocinnamate are obtained in the form of a white solid which melts at 163° C. by proceeding as in Example 34-3 but using 3.6 g of methyl 2-acetamidoacrylate, 0.12 g of palladium acetate, 5.2 g of tetrabutylammonium chloride, 3.8 g of sodium hydrogen carbonate and 4 g of 2-fluoro-4-bromotoluene in solution in 120 ml of anhydrous DMF.

34-8: (R,S)-4-Trifluoromethoxyphenylalanine hydrochloride or (R,S)-O-trifluoromethyltyrosine hydrochloride 1.5 g of (R,S)-4-trifluoromethoxyphenylalanine hydrochloride are obtained in the form of white crystals which melt at 260° C. by proceeding as in Example 34-1 but using 3 g of methyl N-acetyl-(4-trifluoromethoxy)phenylalaninate and 30 ml of 12 N hydrochloric acid.

34-9: Methyl (R,S)-N-acetyl-(4-trifluoromethoxy) phenylalaninate 3 g of methyl N-acetyl-(4-trifluoroethoxy)-phenylalaninate are obtained in the form of a white solid which melts at 80° C. by proceeding as in Example 34-2 but using 3.1 g of methyl (4-trifluoromethoxy)-2-acetamidocinnamate and 0.3 g of 10% palladium on charcoal in 50 ml of ethanol.

34-10: Methyl 4-trifluoromethoxy-2-acetamidocinnamate 3.1 g of methyl (4-trifluoromethoxy)-2-acetamidocinnamate are obtained in the form of a white solid which melts at 135° C. by proceeding as in Example 34-3 but using 4.3 g of methyl 2-acetamido acrylate, 0.14 g of palladium acetate, 6.1 g of tetrabutyl-mmonium chloride, 4.6 g of sodium hydrogen carbonate and 5 g of 4-trifluoromethoxybromobenzene in solution in 150 ml of anhydrous DMF.

34-11: (R,S)-3-Methylthiophenylalanine hydrochloride 1.38 g of (R,S)-3-methylthiophenylalanine hydrochloride are obtained in the form of white crystals which melt at 190° C. by proceeding as in Example 34-1 but using 3.3 g of methyl N-acetyl-3-methylthiophenylalaninate and 40 ml of 12 N hydrochloric acid.

34-12: Methyl (RS)-N-acetyl-3-methylthiophenylalaninate 3.72 g of methyl 3-methylthio-2-acetamidocinnamate, dissolved in 100 ml of methanol, and 30 ml of tetrahydrofuran are placed in a round-bottomed flask, and 1.4 g of magnesium are then added. After reacting for 20 min, the mixture is cooled in an ice bath and a further 1.4 g of magnesium are then added. The mixture is stirred at room temperature for 18 h and then poured into 1.4 l of distilled water and 300 ml of $CH_2Cl_2$; this mixture is then filtered through Clarcel®. The aqueous phase is adjusted to pH 6 by adding 12 N hydrochloric acid and then separated off and washed with 100 ml of $CH_2Cl_2$. The organic phases are collected, dried over magnesium sulphate, filtered and then concentrated to dryness under reduced pressure in order to yield 3.42 g of methyl N-acetyl-3-methylthiophenylalaninate in the form of a colourless oil (Merck Silica 5719, Rf=0.5; AcOEt).

34-13: Methyl 3-methylthio-2-acetamidocinnamate 4.8 g of methyl (3-methylthio)-2-acetamidocinnamate are obtained in the form of a white solid which melts at 139° C. by proceeding as in Example 34-3 but using 5.6 g of methyl 2-acetamidoacrylate, 0.18 g of palladium acetate, 8.2 g of tetrabutylammonium chloride, 5.86 g of sodium hydrogen carbonate and 6.5 g of 3-iodo-1-methylthiobenzene dissolved in 160 ml of anhydrous DMF.

34-14: 3-Iodomethylthiobenzene 20 ml of distilled water and 20 ml of 12 N hydrochloric acid are placed, with stirring, in a three-necked flask, and 10 ml of 3-methylthioaniline are then added using a dropping funnel. The mixture is warmed to ensure dissolution and is then cooled down to 5° C. 5.86 g of sodium nitrite dissolved in 15 ml of water are subsequently added slowly, using a dropping funnel, while maintaining the temperature between 5 and 8° C. 20 min after having completed the addition, 13.57 g of potassium iodide dissolved in 15 ml of water are added over a period of 10 min and the mixture is then stirred at room temperature for 15 h. The oil which forms is separated from the aqueous phase by decantation, and an aqueous solution of sodium thiosulphate is then added to it. The aqueous phase is decanted and the product is extracted with 100 ml of dichloromethane. The organic phase is washed with 100 ml of water, and the aqueous phase is adjusted to pH 9 with concentrated sodium hydroxide solution, and then separated off. The organic phase is washed with 2 times 100 ml of water, separated off, dried over magnesium sulphate, filtered and then concentrated to dryness under reduced pressure (50 kPa) at 40° C. The resulting product is purified by flash chromatography (eluent, cyclohexane) in order to yield 13 g of 3-iodo-1-methylthiobenzene in the form of a yellow liquid (Merck Silica 5719, $R_f$=0.8/cyclohexane).

EXAMPLE 35

Preparation of Derivatives of Phenylalanine Using Method B

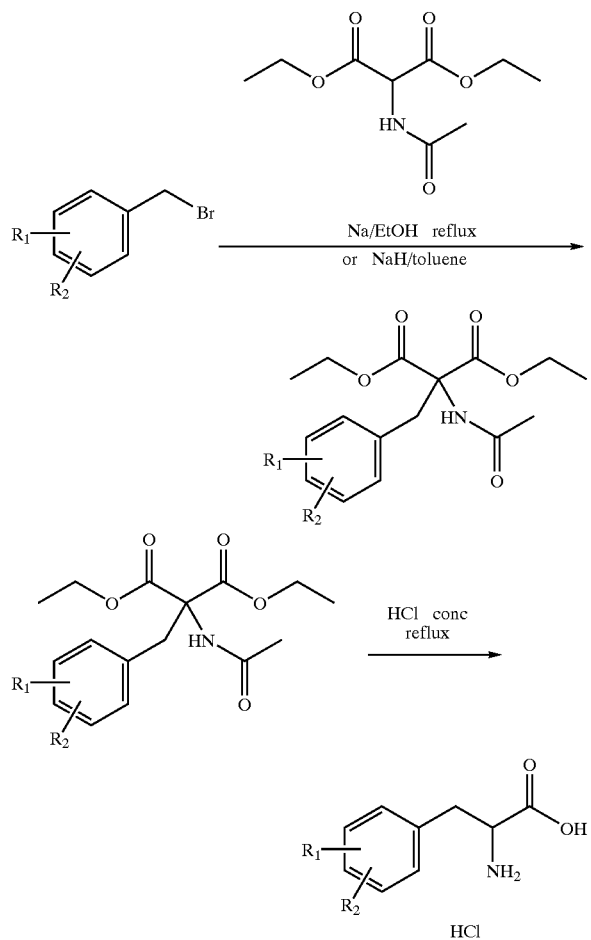

35-1: (RS)-4-tert-butylphenylalanine 25 g of diethyl 4-(tert-butyl)benzyl acetamidomalonate and 250 ml of 37% hydrochloric acid are added to a three-necked flask which is surmounted by a condenser. The mixture is stirred and heated to reflux until there is no further evolution of gas. After the reaction medium has been cooled down, the precipitate which is obtained is filtered and then recrystallized in acetonitrile to yield 25.6 g of (R,S)-4-tert-butylphenylalanine hydrochloride in the form of a white solid which melts at 234° C.

35-2: Diethyl 4-(tert-butyl)benzylacetamidomalonate 25 g of 4-(tert-butyl)benzyl bromide, 50 ml of anhydrous toluene and 3.1 g of sodium hydride in 80% suspension in oil are added to a three-necked flask which is surmounted by a condenser, followed by 21.8 g of diethyl acetamidomalonate. The mixture is heated at 110° C. for 17 h. After it has been cooled down, 15 ml of absolute ethanol, then 15 ml of 50% ethanol and then 50 ml of water are added slowly to it using a dropping funnel. The organic phase is decanted and the aqueous phase is washed with 3 times 50 ml of diethyl ether. The organic phases are combined, washed with water and then dried over sodium sulphate. Following filtration and concentration under reduced pressure, the product is crystallized in petroleum ether in order to yield 25 g of diethyl 4-(tert-butyl)benzylacetamidomalonate in the form of a white solid which melts at 80° C.

35-3: (R,S)-3-Methylaminophenylalanine dihydrochloride 1.03 g of a yellow-beige solid are obtained by proceeding as in Example 35-1 but using 1.17 g of diethyl 3-methylaminobenzylacetamidomalonate and 20 ml of 12 N hydrochloric acid. This yellow-beige solid is dissolved in 20 ml of absolute ethanol, and 0.4 g of animal charcoal is added to this solution. The solution is filtered through Clarcel and then filtered and concentrated under reduced pressure (50 kPa). The same procedure is repeated starting with 1 g of animal charcoal, and the solid which is obtained is triturated in 20 ml of ether. Following filtration and drying under reduced pressure (2.7 kPa) at 50° C., 0.65 g of (R,S)-3-methylaminophenylalanine dihydrochloride is obtained in the form of a white powder which melts at a temperature approaching 135° C. (decomposition).

35-4: Diethyl 3-methylamino benzyl acetamido malonate 3.11 ml of acetic anhydride are placed in a three-necked flask which is maintained under a nitrogen atmosphere. 1.51 ml of formic acid are subsequently added within 3 min at 0° C., and the mixture is then heated at 50° C. for 2 hours. The mixture is allowed to return to room temperature, while shaking for 3 h 20 min, and 4 ml of anhydrous THF are added under nitrogen; the mixture is then cooled to −20° C. A solution of 4 g of diethyl 3-aminobenzylacetamidomalonate in a mixture of 15 ml of anhydrous THF and 15 ml of anhydrous dichloromethane is added within 10 min. Stirring is continued for 1 h 10 min at −20° C. and then for 16 h at 20° C. The reaction mixture is concentrated to dryness under reduced pressure (50 kPa) at 30° C. and then co-evaporated with 30 ml of anhydrous toluene in order to yield a white solid, which is dissolved in a mixture of 10 ml of anhydrous THF and 20 ml of anhydrous 1,2-dichloroethane, which solution is then placed in a three-necked flask under nitrogen.

The medium is cooled down to −5° C., and 1.55 ml of borane-dimethyl sulphide complex (2M solution in THF) are then added within 10 min. The mixture is allowed to return to room temperature, and the solution is heated to reflux for 3 h and then stirred at room temperature for 15 h. The reaction medium is cooled to 0° C., and 10 ml of MeOH are then added within 25 min. The mixture is stirred for 45 min at 0° C. and then for 30 min at room temperature. It is then cooled to 0° C. and HCl gas is bubbled in until a pH of 2 is reached. The mixture is heated at reflux for 1 h and is then concentrated to dryness under reduced pressure at 30° C. in order to yield 5 g of a product which is taken up in 30 ml of an aqueous solution of $NaHCO_3$ and 30 ml of $CH_2Cl_2$. The organic phase is decanted and the aqueous phase is washed with 20 ml of water. The organic phases are pooled, dried over magnesium sulphate, filtered and then concentrated to dryness under reduced pressure (2.6 kPa) in order to yield 3.43 g of a yellow oil, which is purified by flash chromatography (eluent, AcOEt/cyclohexane 50/50). After drying under reduced pressure (2.7 kPa) at 20° C., 1.18 g of diethyl 3-methylaminobenzylacetamidomalonate are thus obtained in the form of a light beige solid which melts at 122° C.

35-5: Diethyl 3-aminobenzylacetamidomalonate

Diethyl 3-aminobenzylacetamidomalonate can be prepared as described in:

T. S. Osdene, D. N. Ward, W. H. Chapman and H. Rakoff, J. Am. Chem. Soc., 81, 1959, 3100–3102.

35-6: (R,S)-3-Ethylaminophenylalaninedihydrochloride 1.7 g of (R,S)-3-ethylaminophenylalanine dihydrochloride are obtained in the form of a hygroscopic light beige solid, which contains 10 molar % of (R,S)-3-diethylaminophenylalanine dihydrochloride, by proceeding as in Example 34-1 but using 2 g of ethyl (R,S)-N-acetyl-3-ethylamino-phenyl-alaninate and 30 ml of 12N hydrochloric acid.

35-7: (R,S)-N-acetyl-3-ethylaminophenyl-alaninate 3 g of ethyl (R,S)-N-acetyl-3-aminophenyl-alaninate, 40 ml of ethanol and 14 g of Raney nickel, which has previously been washed with distilled water and ethanol, are placed in a round-bottomed flask under a nitrogen atmosphere. The mixture is heated to reflux for 19 h, cooled down, filtered through Clarcel®, and then concentrated to dryness under reduced pressure (50 kPa) in order to yield 3.07 g of a colourless oil, which is purified by flash chromatography (eluent, AcOet) in order to yield 2.1 g of ethyl (R,S)-N-acetyl-3-ethylaminophenylalaninate in the form of a colourless oil (Merck Silica 5719, $R_f$=0.6: AcOEt) which contains 10% ethyl (R,S)-N-acetyl-3-diethylaminophenylalaninate.

35-8: Ethyl (R,S)-N-acetyl-3-aminophenylalaninate 25 g of a mixture of ethyl (R,S)-N-acetyl-3-nitrophenylalaninate (75 mol %/mol) and diethyl 3-nitrobenzylacetamidomalonate (25 mol %/mol) are placed under nitrogen in an autoclave. 2.5 g of 10% palladium on charcoal and then 200 ml of dichloromethane are added. The mixture is placed under a hydrogen pressure of 9 bar and then stirred at 18° C. for 4 h. After returning the pressure to atmospheric, the reaction medium is filtered through Clarcel®, washed with dichloromethane and then concentrated to dryness under reduced pressure (50 kPa) in order to yield a solid, which is recrystallized in 450 ml of distilled water under reflux and in the presence of 4 g of 3S animal charcoal. Following hot filtration through Clarcel®, the mixture is left to crystallize at 4° C., with the crystals being filtered and then dried in order to yield 9.9 g of ethyl (R,S)-N-acetyl-3-aminophenylalaninate in the form of a light beige solid which melts at 106° C. and which contains 5% of diethyl 3-aminobenzylacetamidomalonate.

35-9: Ethyl (R,S)-N-acetyl-3-nitrophenyl-alaninate and diethyl 3-nitrobenzylacetamidomalonate 600 ml of absolute ethanol and then 7.9 g of sodium are placed, under a nitrogen atmosphere, in a three-necked flask which is surmounted by a condenser. Once dissolution is complete, 74.5 g of diethyl acetamidomalonate and then 60 g of 4-nitrobenzyl chloride in 200 ml of anhydrous ethanol are added. The mixture is heated to reflux for 16 h 30 min. After cooling, the reaction medium is concentrated under reduced pressure (50 kPa) and then taken up in a mixture of 500 ml of $CH_2Cl_2$ and 500 ml of water. The pH is adjusted to 7 by adding 0.5N sulphuric acid, and the organic phase is then separated off and the aqueous phase is washed with 2 times 200 ml of $CH_2Cl_2$. The organic phases are pooled, washed with 200 ml of water saturated with sodium bicarbonate, separated off and then dried over magnesium sulphate. Following filtration and concentration under reduced pressure (50 kPa), the product is recrystallized in 600 ml of ethanol at reflux in order to yield, after crystallizing at ambient temperature, filtering and drying, 70.4 g of diethyl 3-nitrobenzylacetamido-malonate in the form of white crystals which melt at 156° C. The mother liquors are concentrated and then purified by flash chromatography (eluent, AcOEt) in order to yield 25.6 g of a mixture of ethyl N-acetyl-3-nitrophenylalaninate (75 mol %/mol) and diethyl 3-nitrobenzylacetamidomalonate (25 mol %/mol) in the form of a light beige solid, which is used in this form in the following step.

35-10: (RS,)-3-Dimethylaminophenylalanine dihydrochloride

A solid is obtained, after evaporation, by proceeding as in Example 35-1 but using 0.72 g of ethyl (RS)-N-acetyl-3-dimethylaminophenylalaninate and 8.6 ml of 10N hydrochloric acid; the solid is subsequently triturated in 50 ml of acetone, filtered and then dried under reduced pressure (2.7 kPa) at 40° C. 0.68 g (93%) of (RS)-3-dimethylaminophenylalanine dihydrochloride is obtained in the form of a white solid which melts in the region of 120° C. (decomposition).

35-11: Ethyl (RS)-N-acetyl-3-dimethylaminophenylalaninate 4 g of ethyl (RS)-N-acetyl-3-aminophenylalaninate, prepared as described in Example 35-8, in 15 ml of DMF are placed in a three-necked flask under a nitrogen atmosphere, and 5.5 ml of triethylamine, and then 2.5 ml of methyl iodide and 4 ml of dichloromethane, are added while maintaining the temperature in the region of 30° C. using an icebath. The mixture is then warmed at 35° C. for 18 h. 1 ml of methyl iodide dissolved in 1 ml of DMF is then added slowly while maintaining the temperature in the region of 30° C.; 2.2 ml of triethylamine are then added and the mixture is subsequently warmed for a further 5 h at 35° C. The mixture is brought to room temperature and then extracted with 100 ml of ethyl acetate and 150 ml of distilled water. The aqueous phase is separated off after settling and then rewashed with 2 times 70 ml of ethyl acetate. The organic phases are combined, washed with 2 times 80 ml of distilled water and then with 50 ml of distilled water which is saturated with NaCl. The organic phase is separated off after settling, dried over magnesium sulphate, filtered and then concentrated to dryness under reduced pressure in order to yield 2.4 g of a product which is purified by flash chromatography (dichloromethane, MeOH 90/10). 0.72 g (16%) of ethyl (RS)-3-N-acetyl-3-dimethylamino phenylalaninate is thus obtained in the form of yellow crystals.

EXAMPLE 36

Preparation of Derivatives of Phenylalanine Using Method C

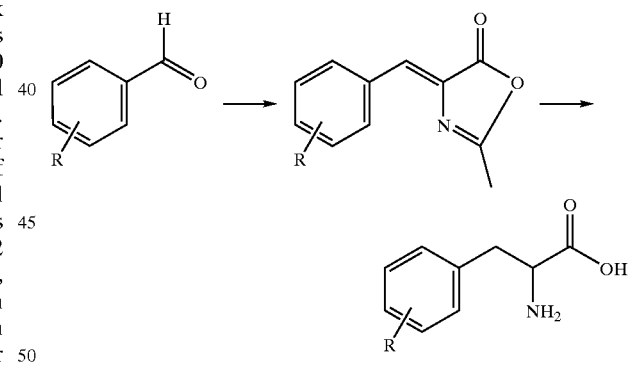

36-1: (R,S)-4-Isopropylphenylalanine 7 g of red phosphorus and 8 g of 4-(isopropylbenzylidene)-2-methyl-5-oxazolone, in 45 ml of acetic anhydride, are placed in a three-necked flask, and then 35 ml of 57% hydriodic acid are added slowly, with stirring, using a dropping funnel. Once the addition is complete, the mixture is heated to reflux for 3 h 30 min and then left at room temperature for 3 days. The reaction mixture is filtered and the solid which is obtained is rinsed twice with 10 ml of acetic acid on each occasion, and the filtrate is then concentrated to dryness under reduced pressure. The residue which is obtained is taken up in 100 ml of distilled water, and this solution is concentrated to dryness under reduced pressure in order to yield a solid which is taken up in 50 ml of distilled water; this solution is then extracted with 3 times 50 ml of diethyl ether after 0.5 g of sodium sulphite have been added. The ether is separated off and the aqueous phase is placed under reduced pressure in order to eliminate traces of diethyl ether. 2 g of animal charcoal are added to the aqueous phase, which is heated at 40–50° C., and then filtered through Clarcel®; rinsing then takes place with a minimum of water. The pH is adjusted to 5 by adding 32% ammonia at 4° C. The precipitate which is obtained is filtered in the cold, rinsed with 2 times 10 ml of water, with 10 ml of ethanol and then with 2 times 10 ml of ether in order to yield, after drying under reduced pressure at 20° C., 3.97 g of (R,S)-4-isopropylphenylalanine in the form of a white solid which melts at a temperature greater than 260° C. (See also Journal of the Takeda Research Laboratories, vol. 43; nos. 3/4, December 1984, pp 53–76).

36-2: 4-(Isopropylbenzylidene)-2-methyl-5-oxazolone 18.52 g of N-acetylglycine, 10.6 g of sodium acetate, 20 ml of 4-isopropylbenzaldehyde and 57 ml of acetic anhydride are placed in a round-bottomed flask which is provided with a condenser. The mixture is stirred for 30 min and then stirred for 1 h at 110° C. and subsequently for 15 h at room temperature. The reaction medium is poured into 600 ml of water and 400 ml of petroleum ether which has previously been heated to 50° C. The organic phase is separated off and the aqueous phase is washed with 2 times 150 ml of petroleum ether.

The organic phases are combined, dried over magnesium sulphate, filtered and concentrated under reduced pressure until the volume is 100 ml and a precipitate is obtained. The latter is filtered and washed with 2 times 50 ml of pentane in order to yield 8.2 g of 4-(isopropylbenzylidene)-2-methyl-5-oxazolone in the form of a yellow solid which melts at 77° C.

36-3: (R,S)-4-Butylphenylalanine 0.35 g of (R,S)-4-butylphenylalanine is obtained in the form of a light beige solid which melts at a temperature greater than 260° by proceeding as in Example 36-1 but using 1.49 g of red phosphorus, 1.8 g of 4-(butylbenzylidene)-2-methyl-5-oxazolone, in 9.23 ml of acetic anhydride, and 7.39 ml of 57% hydriodic acid.

36-4: 4-(Butylbenzylidene)-2-methyl-5-oxazolone 1.89 g of 4-(butylbenzylidene)-2-methyl-5-oxazolone are obtained in the form of a yellow solid which melts at 74° C. by proceeding as in Example 36-2 but using 8.43 g of N-acetylglycine, 4.92 g of sodium acetate, 9.8 g of 4-butylbenzaldehyde and 26 ml of acetic anhydride.

EXAMPLE 37

Preparation of a Derivative of Phenylalanine Using Method D 37-1: (R,S)-3-Ethoxyphenylalanine hydrochloride (or (R,S)-3-O-ethyltyrosine hydrochloride)

1 g of (R,S)-N-tert-butoxycarbonyl-3-ethoxyphenylalanine, dissolved in 3.6 ml of hydrochloric dioxane, is placed in a round-bottomed flask, and the mixture is then stirred at room temperature for 5 h. The precipitate which forms is filtered, rinsed with dioxane and then ether, and then dried under reduced pressure (2.7 kPa) at 40° C. to yield 0.65 g of (R,S)-3-ethoxyphenylalanine hydrochloride in the form of a white solid which melts at 200° C.

37-2: (R,S)-N-tert-Butoxycarbonyl-3-ethoxyphenylalanine 1.33 g of ethyl (R,S)-N-tert-butoxycarbonyl-3-ethoxyphenylalaninate, dissolved in 8 ml of methanol, are placed in a round-bottomed flask, and 8 ml of 1N sodium hydroxide solution are then added. After the mixture has been stirred at room temperature for 18 h, it is evaporated under reduced pressure and then acidified with 8.56 ml of 1N hydrochloric acid. The product is extracted with 2 times 10 ml of ethyl acetate, and the organic phases are pooled, washed with 2 times 10 ml of water, dried, filtered and then concentrated to dryness under reduced pressure to yield 1 g of (R,S)-N-tert-butoxycarbonyl-3-ethoxyphenylalanine in the form of a yellow oil (Merck Silica 5719, $R_f$=0.7, eluent: toluene 80/MeOH 10/diethylamine 10).

37-3: (R,S)-N-tert-Butoxycarbonyl-3-ethoxyphenylalaninate 1.5 g of (R,S)-N-tert-butoxycarbonyl-3-tyrosine, dissolved in 7.5 ml of dry DMF, are placed in a three-necked flask under a nitrogen atmosphere, and 0.508 g of sodium hydride, as a 50% dispersion in oil, is then added. After the mixture has been stirred at room temperature for 2 h, 0.86 ml of iodoethane is added and the mixture is then stirred at room temperature for 4 h. The medium is filtered and the resulting solid is washed with 3 times 10 ml of water and then 2 times 10 ml of petroleum ether to yield, after drying under reduced pressure (2.7 kPa) at 30° C., 1.33 g of ethyl (R,S)-N-tert-butoxycarbonyl-3-ethoxyphenylalaninate in the form of a white solid.

37-4: (R,S)-N-tert-Butoxycarbonyl-3-tyrosine 18 g of (R,S)-3-tyrosine, dissolved in 180 ml of dioxane, are placed, with stirring, in a three-necked flask, and 99 ml of 1N sodium hydroxide solution, followed by 26 g of di-tert-butyl dicarbonate, dissolved in 160 ml of dioxane, are then added. After the mixture has been stirred for 36 h, it is concentrated under reduced pressure at 30° C. and the residue is taken up in 100 ml of distilled water; this solution is acidified to pH 5 with 1N hydrochloric acid and then extracted with 2 times 200 ml of ethyl acetate. The organic phase is dried over magnesium sulphate, filtered and then concentrated to dryness under reduced pressure at 30° C. to yield 30 g of (R,S)-N-tert-butoxycarbonyl-3-tyrosine in the form of a white solid (Merck Silica 5719, $R_f$=0.25, eluent: toluene 80, MeOH 10, diethylamine 10).

EXAMPLE 38

Preparation of Derivatives of Phenylalanine Using Method E 38-1: (RS)-4-Diallylaminophenylalanine dihydrochloride A solid is obtained, after evaporation, by proceeding as in Example 35-1 but using 5.8 g of diethyl 4-diallylaminobenzylacetamido malonate and 48 ml of 10N hydrochloric acid; the solid is then triturated in 50 ml of acetone, filtered, then triturated in 10 ml of dichloromethane, filtered and then rinsed with 3 times 10 ml of ethyl ether. After drying under reduced pressure (2.7 kPa) at 40° C., 4.41 g of (RS)-4-diallylaminophenylalanine dihydrochloride are obtained in the form of an off-white solid which melts in the region of 135° C. (decomposition).

38-2: (RS)-4-Allylaminophenylalanine dihydrochloride

A solid is obtained, after evaporation, by proceeding as in Example 35-1 but using 3.27 g of diethyl 4-allylaminobenzylacetamidomalonate and 30 ml of 10N hydrochloric acid; the solid is then triturated in 50 ml of acetone, filtered and then dried under reduced pressure (2.7 kPa) at 40° C. 2.3 g of (RS)-4-allylaminophenylalanine dihydrochloride are obtained in the form of a white solid which melts in the region of 134° C. (decomposition).

38-3: Diethyl 4-diallylaminobenzylacetamidomalonate and diethyl 4-allylaminobenzylacetamidomalonate 10 g of diethyl 4-aminobenzylacetamidomalonate dissolved in 150 ml of DMF are placed in a three-necked flask which is surmounted with a dropping funnel and maintained under a nitrogen atmosphere. 6.57 ml of allyl bromide, and then 10.76 ml of triethylamine, are added slowly, at room temperature and while stirring. After stirring for 19 h, a further 1.31 ml of allylbromide and 2.15 ml of triethylamine are then added and the mixture is stirred for 26 h. The reaction medium is poured onto 1.5 l of distilled water and this mixture is extracted with 1 l of ethyl acetate. The aqueous phase is separated off after settling and washed with 2 times 500 ml of ethyl acetate. The organic phases are combined, washed with 500 ml of distilled water and then with 500 ml of water which is saturated with sodium chloride, separated off, dried over magnesium sulphate, filtered and then concentrated to dryness in order to yield a chestnut oil; this oil is purified by flash chromatography (eluant, $CH_2Cl_2$ 90/AcOEt 10) in order to yield 6.66 g of diethyl 4-diallylaminobenzyl-acetamidomalonate in the form of a beige solid which melts at 94–96° C. (Rf=0.6, AcOEt 50/cyclohexane 50) and 3.49 g of diethyl 4-allylaminobenzylacetamidomalonate in the form of a beige solid which melts at 104–106° C. (Rf=0.45 AcOEt 50/cyclohexane 50).

The diethyl 4-aminobenzylacetamidomalonate can be prepared as described in J. B. Burckhalter, V C Stephens, J. Am. Chem. Soc. 5, 1951, 73.

EXAMPLE 39

Preparation of Derivatives of Phenylalanine Using Method F

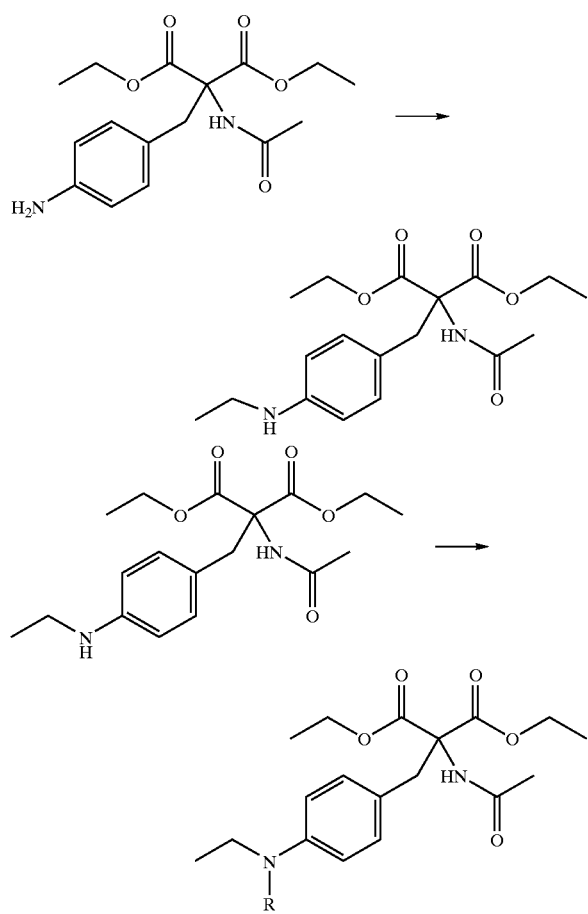

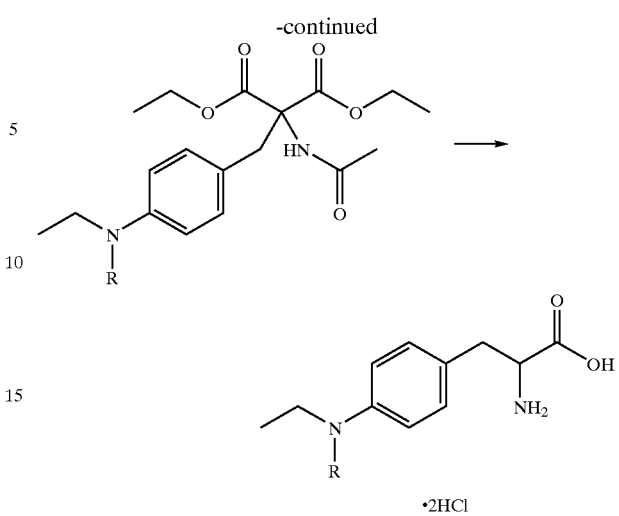

39-1: (RS)-4-ethylisopropylphenylalanine dihydrochloride

A solid is obtained, after evaporation, by proceeding as in Example 35-1 but using 2.9 g of diethyl 4-ethylisopropylbenzylacetamidomalonate and 24.6 ml of 10N hydrochloric acid; the solid is then triturated in 20 ml of acetone, filtered and then dried under reduced pressure (2.7 kPa) at 40° C. 2 g of (RS)-4-ethylisopropylaminophenylalanine dihydrochloride are obtained in the form of a white solid which melts in the region of 147° C. (decomposition).

39-2: Diethyl 4-ethylisopropylaminobenzylacetamidomalonate 15 g of diethyl 4-ethylaminobenzylacetamidomalonate in 70 ml of THF are placed in a three-necked flask which is maintained under a nitrogen atmosphere; 6.4 ml of 2-iodopropane, and then 8.4 ml of 1,5-diazabicyclo[4.3.0]non-5-ene are added and the mixture is then heated at 60° C. for 24 h. 2.13 ml of 2-iodopropane, and then 8.4 ml of 1,5-diazabicyclo[4.3.0]non-5-ene, are subsequently added and the mixture is then heated for a further 24 h at 60° C. The mixture is brought to room temperature and then extracted with 50 ml of dichloromethane and 50 ml of distilled water. The aqueous phase is separated off after settling and then rewashed with 2 times 30 ml of dichloromethane. The organic phases are combined, washed with 60 ml of distilled water and then with 50 ml of distilled water which is saturated with NaCl. The organic phase is separated off after settling, dried over magnesium sulphate, filtered and then concentrated to dryness under reduced pressure in order to yield 16.2 g of a product which is purified by flash chromatography (dichloromethane, MeOH 90/10). This results in 4.59 g of a product which is recrystallized in 45 ml of cyclohexane in order to yield 3.44 g of diethyl 4-ethylisopropylamino-benzylacetamidomalonate in the form of white crystals which melt at 80° C.

39-3: Diethyl 4-ethylaminobenzylacetamidomalonate

Diethyl 4-ethylaminobenzylacetamidomalonate can be prepared by proceeding as in Example 35-7 but using 22 g of diethyl 4-aminobenzylacetamidomalonate, 500 ml of ethanol and 70 g of Raney nickel. This results in 23.8 g of diethyl 4-ethylaminobenzylacetamidomalonate in the form of an off-white solid which melts at 136° C.

39-4: (RS)-4-Allylethylaminophenylalanine dihydrochloride

A solid is obtained, after evaporation, by proceeding as in Example 35-1 but using 4.54 g of diethyl 4-allylethylbenzylacetamidomalonate and 37.9 ml of 10N hydrochloric acid; the solid is then dried under reduced pressure (2.7 kPa) at 40° C. 3.67 g of (RS)-4-allylethylaminophenylalanine dihydrochloride are obtained in the form of a brown solid which melts in the region of 130° C. (decomposition).

39-5: Diethyl 4-allylethylaminobenzylacetamidomalonate 5.6 g of a solid are obtained, after purification by flash chromatography (eluant, CH2Cl2/AcOET 90-10 by volume), by proceeding as in Example 39-2 but using 8 g of diethyl 4-ethylaminobenzylacetamidomalonate, 4 ml of allyl bromide and 5.82 ml of 1,5-diazabicyclo[4.3.0]non-5-ene in 50 ml of THF; the solid is then recrystallized in 35 ml of cyclohexane. This results in 5.43 g of diethyl 4-allylethylaminobenzylacetamidomalonate in the form of a white solid which melts at 86° C.

39-6: (RS)-4-Ethylpropylaminophenylalanine dihydrochloride

A solid is obtained, after evaporation, by proceeding as in Example 35-1 but using 2.5 g of diethyl 4-ethylpropylaminobenzylacetamidomalonate and 21 ml of 10N hydrochloric acid. The solid is then dried under reduced pressure (2.7 kPa) at 40° C. 2 g (97%) of (R,S)-4-ethylpropylaminophenylalanine dihydrochloride are obtained in the form of a white solid which melts in the region of 147° C. (decomposition).

39-7: Diethyl 4-ethylpropylaminobenzylacetamidomalonate 2.8 g of a solid are obtained, after reacting for 36 hours and then purifying by flash chromatography (eluant, CH2Cl2/MeOH 97-3 by volume), by proceeding as in Example 39-2 but using 10 g of diethyl 4-ethylaminobenzylacetamidomalonate, 5.6 ml of 1-iodopropane and 7.2 ml of 1,5-diazabicyclo[4.3.0]non-5-ene in 70 ml of THF; the solid is then recrystallized in 26 ml of cyclohexane. This results in 2.9 g of diethyl 4-ethylpropylaminobenzylacetamidomalonate in the form of a white solid which melts at 84–86° C.

39-8: (RS)-4-Ethylmethylcyclopropylaminophenylalanine dihydrochloride

A solid is obtained, after reacting for 3 days and then evaporating, by proceeding as in Example 35-1 but using 3 g of diethyl 4-ethylmethylcyclopropylaminobenzylacetamidomalonate and 25 ml of 10N hydrochloric acid; the solid is then triturated in 40 ml of acetone, filtered and then dried under reduced pressure (2.7 kPa) at 40° C. 2.24 g of (RS)-4-ethylmethylcyclopropylamino-phenylalanine dihydrochloride are obtained in the form of a white solid which melts in the region of 140° C. (decomposition).

39-9: Diethyl 4-ethylmethylcyclopropylaminobenzylacetamidomalonate

By proceeding as in Example 39-2, but using 8 g of diethyl 4-ethylaminobenzylacetamidomalonate, 2.6 ml of bromomethylcyclopropane and 2.97 ml of 1,5-diazabicyclo[4.3.0]non-5-ene in 50 ml of THF, 3.3 g of diethyl 4-ethylmethylcyclopropylaminobenzylacetamidomalonate are obtained, after reacting for 3 days and then purifying by flash chromatography (eluant CH2Cl2/AcOEt 90-10 by volume), in the form of a white solid which melts at 112–114° C.

EXAMPLE 40

Preparation of Derivatives of Phenylalanine Using Method G

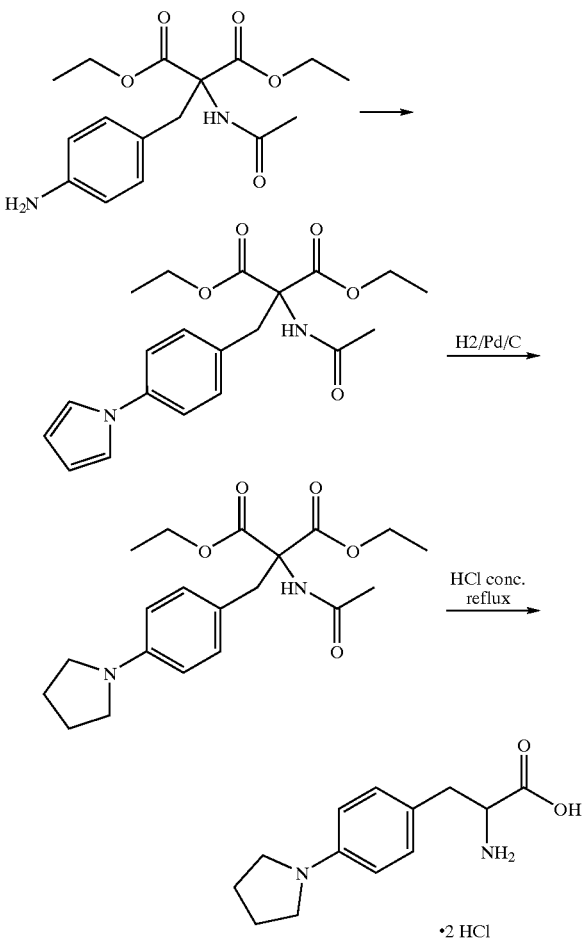

40-1: (RS)-4-(1-Pyrrolidinyl)phenylalanine dihydrochloride

A solid is obtained, after evaporation, by proceeding as in Example 35-1 but using 1.5 g of diethyl 4-(1-pyrrolidinyl) benzylacetamidomalonate and 40 ml of 5N hydrochloric acid; the solid is then triturated in 15 ml of acetone, filtered and then dried under reduced pressure (2.7 kPa) at 40° C. 0.6 g of (RS)-4-(1-pyrrolidinyl)phenylanaline dihydrochloride is obtained in the form of an off-white solid.

40-2: Diethyl 4-(1-pyrrolidinyl)benzylacetamidomalonate 4 g of diethyl 4-(1-pyrrolyl)benzylacetamidomalonate, dissolved in 100 ml of MeOH, and 1 g of 10% palladium on charcoal are placed in an autoclave. After having purged the autoclave 3 times with nitrogen, the product is hydrogenated at 19° C. under a pressure of 14 bars of hydrogen. After stirring for 25 hours, the hydrogenation is stopped and the product is filtered through Clarcel® and rinsed with dichloromethane; the solution is then concentrated under reduced pressure in order to yield 3.85 g of a solid which is triturated in a mixture of 50 ml of heptane and 10 ml of ethyl ether. The resulting solid is filtered, dried and then purified by flash chromatography (eluant CH$_2$Cl$_2$/acetone 90/10 by volume) in order to yield 1.6 g of diethyl 4-(1-pyrrolidinyl) benzylacetamidomalonate in the form of a white solid which melts at 132° C.

40-3: Diethyl 4-(1-pyrroyl)benzylacetamidomalonate 4.6 g of diethyl 4-aminobenzylacetamidomalonate in 104 ml of acetic acid are placed in a three-necked flask which is maintained under nitrogen. 7.02 g of sodium acetate are added, followed by 1.87 ml of 2,5-dimethoxytetrahydrofuran. The mixture is heated at 65° C. for 1 h 15 min, then cooled down and extracted with 100 ml of dichloromethane and 100 ml of distilled water. The aqueous phase is separated off after settling and then washed with 3 times 100 ml of dichloromethane. The organic phases are combined, washed with 100 ml of water and then with 100 ml of a saturated solution of NaCl, separated off after settling and then dried over magnesium sulphate; the phases are filtered and then evaporated to dryness under reduced pressure (50 kPa) in order to yield 6.2 g of a solid which is purifed by flash chromatography (eluent CH2Cl2/acetone 75/25 by volume). This results in 3.57 g of diethyl 4-(1-pyrrolyl)benzylacetamidomalonate in the form of a beige solid which melts at 110° C.

EXAMPLE 41

Preparation of Derivatives of Phenylalanine Using Method H 41-1: (RS)-4-Ethylthiomethylphenylalanine 300 ml of anhydrous methanol are placed in a three-necked flask which is maintained under nitrogen; subsequently, 1.72 g of sodium methoxide, and then 5.55 ml of ethyl mercaptan, are added while stirring. The solvent is concentrated under reduced pressure at 40° C. in order to yield 8.5 g of the sodium salt of ethyl mercaptan, which is dissolved in 100 ml of anhydrous THF. 3.6 g of (RS)-4-chloromethylphenylalanine are added at room temperature and the mixture is then heated to reflux for 18 h. The solvent is evaporated under reduced pressure at 40° C. and the residue is taken up in 100 ml of distilled water. The turbid solution which is obtained is acidified with 5 ml of acetic acid. The resulting precipitate is filtered, rinsed with distilled water and then dried at 60)C under reduced pressure in order to yield 3.6 g of a solid which is purified by flash chromatography (eluant AcOEt 60, AcOH 12, water 10). This results in 256 mg of (RS)-4-ethylthiomethylphenylalanine in the form of a white solid which melts at 251° C.

The (RS)-4-chloromethylphenylalanine can be obtained by analogy with (S)-4-chloromethylphenylalanine as described in: R. Gonzalez-Muniz, F. Cornille, F. Bergeron, D. Ficheux, J. Pothier, C. Durieux and B. Roques, Int. J. Pept. Protein. Res., 1991, 37 (41), 331–340.

EXAMPLE 42

Preparation of Derivatives of Phenylalanine Using Method I 42-1: (S)-4-O-(2-Chloroethyl)tyrosine hydrochloride 5 g of (S)-N-tert-butoxycarbonyl-4-O-(2-chloroethyl) tyrosine, dissolved in 50 ml of hydrochloric dioxane, are placed in a round-bottomed flask. After having been stirred for 28 h, the mixture is concentrated to dryness under reduced pressure. The resulting residue is taken up in 50 ml of ether and this solution is then stirred and filtered. The resulting solid is washed with 2 times 25 ml of ether and then dried under reduced pressure in order to yield 1.58 g of (S)-4-O-(2-chloroethyl)tyrosine hydrochloride in the form of a white solid which melts at 260° C.

42-2: (S)-N-tert-Butoxycarbonyl-4-O-(2-chloroethyl) tyrosine 14 g of (S)-N-tert-butoxycarbonyltyrosine, dissolved in 140 ml of DMF, are placed in a three-necked flask under a nitrogen atmosphere. 4.8 g of 50% sodium hydride in oil are added slowly using a spatula. 16.87 g of 1-tosyl-2-chloroethanol are added after the mixture has been stirred for 2 h at room temperature. 2.4 g of 50% sodium hydride in oil, and a further 8.4 ml of 1-tosyl-2-chloroethanol, are added after the mixture has been stirred for 2 days. The same procedure is carried out after 24 h and the stirring is continued for a further 24 h. The reaction is stopped by adding 100 ml of distilled water, and the reaction mixture is concentrated to dryness under reduced pressure. The residue which is obtained is taken up in 100 ml of distilled water and then extracted with 3 times 100 ml of ethyl acetate. The aqueous phase is separated off after settling and acidified to $pH_3$ with 50 ml of 1N HCl, and the product is extracted with 3 times 100 ml of ethyl acetate. The organic phases are combined, washed with 2 times 50 ml of water, separated off, dried over magnesium sulphate, filtered and then concentrated to dryness under reduced pressure in order to yield 13.51 g of (S)-N-tert-butoxycarbonyl-4-O-(2-chloroethyl) tyrosine in the form of a chestnut oil (Rf=0.5, toluene 70%/methanol 20%/diethylamine 10%), which is used as such in the following step.

TABLE V

| MICROORGANISMS | ANTIBIOTICS |
|---|---|
| FUNGI | |
| Micromonospora sp. | Vernamycins |
| STREPTOMYCES | |
| S. alborectus | Virginiamycins |
| S. conganensis (ATCC13528) | F1370 A, B |
| S. diastaticus | Plauracins, Streptogramins |
| S. graminofasciens | Streptogramins |
| S. griseus (NRRL2426) | Viridogrisein (Etamycin) |
| S. griseoviridus | Griseoviridin |
| S. griseoviridus (FERMP3562) | Neoviridogriseins |
| S. lavendulae | Etamycins |
| S. loidensis (ATCC11415) | Vernamycins |
| S. mitakaensis (ATCC15297) | Mikamycins |
| S. olivaceus (ATCC12019) | Synergistins (PA 114 A, B) |
| S. ostreogriseus (ATCC27455) | Ostreogrycins |
| S. pristinaespiralis (ATCC25486) | Pristinamycins |
| S. virginiae (ATCC13161) | Virginiamycins (Staphylomycins) |
| ACTINOMYCETES | |
| A. auranticolor (ATCC31011) | Plauracins |
| A. azureus (ATCC31157) | Plauracins |
| A. daghestanicus | Etamycin |
| A. philippinensis | A-2315 A,B,C |
| Actinoplanes sp. (ATCC3302) | A15104 |
| Actinoplanes sp. | A17002 A,B,C,F |
| Actinomadura flava | Madumycins |

| Abbreviations employed: | |
|---|---|
| AcOEt | ethyl acetate |
| DNA | deoxyribonucleic acid |
| AMP | adenosine 5'-monophosphate |
| HPLC | high-performance liquid chromatography |
| dCTP | deoxycytosine 5'-triphosphate |
| DMF | dimethylformamide |
| DMPAPA | 4-dimethylamino-L-phenylalanine |
| HCl | hydrochloric acid |
| HT7 | Hickey Tresner solid medium |
| 3-HPA | 3-hydroxypicolinic acid |
| IPTG | isopropyl-β-D-thiogalactopyranoside |
| kb | kilobase |
| LB | Luria broth (rich growth medium for E. coli) |

-continued

| Abbreviations employed: | |
|---|---|
| MeOH | methanol |
| MMPAPA | 4-methylamino-L-phenylalanine |
| NaOH | sodium hydroxide |
| PAPA | 4-amino-L-phenylalanine |
| PEG | polyethylene glycol |
| P I | pristinamycin I |
| P II | pristinamycin II |
| bp | base pair |
| SAM | S-adenosylmethionine |
| TE | 10 mM Tris-HCl buffer, 1 mM EDTA, pH 7.5 |
| THF | tetrahydrofuran |
| Tris | 2-amino-2-(hydroxymethyl)-1,3-propanediol |
| UV | ultraviolet rays |
| X-gal | 5-bromo-4-chloro-3-indoyl-β-D-galactoside |
| YEME | yeast extract-malt extract medium (rich growth medium for Streptomyces) |

Bibliography

Bibb M. J., Findlay P. R. and Johnson M. W. (1984) *Gene*, 30: 157–166.
Bibb M. J., Janssen G. R., and Ward J. M. (1985) *Gene*, 38: 215–226.
Cocito C. G. (1979) *Microbiol. Rev.*, 43: 145–198.
Cocito C. G. (1983) *In Antibiotics*, 6: (Ed. F. E. Hahn), 296–332.
Dessen P. C., Fondrat C., Valencien C. and Mugnier C. (1990) *Compl. Appl. in Biosciences*, 6: 355–356.
Di Giambattista M., Chinali G. and Cocito C. G. (1989) *J. Antim. Chemother.*, 24: 485–507
Gibson T. J. (1984) Ph.D. thesis, Cambridge University, England.
Hillemann D., Pülher A. and Wohlleben W. (1991) *Nucl. Acids Res.*, 19: 727–731.
Hopwood D. A., Bibb M. J., Chater K. F., Kieser T., Bruton C. J., Kieser H. M., Lydiate D. J., Smith C. P., Ward J. M. and Scrempf H. (1985) *A laboratory manual.*, The John Innes Foundation, Norwich, England.
Hudson G. S. and Davidson B. E. (1984) *J. Mol. Biol.*, 180: 1023–1051.
Kuhstoss S., Richardson M. A., and Rao R. N. (1991) *Gene* 97: 143–146.
Maniatis T., Fritsch E. F. and Sambrook J. (1989) Molecular cloning: a laboratory manual. Cold Spring Harbor, N.Y.,
Messing J., Crea R. and Seeburg P. H. (1981) *Nucleic Acid Res.* 9: 309.
Molinero A. A., Kingston D. G. I. and Reed J. W. (1989) *J. Nat. Prod.*, 52: 99–108.
Omer C. A., Lenstra R., Litle P. J., Dean J., Tepperman J. M., Leto K. J., Romesser J. A., and O'Keefe D. P. (1990) *J. Bact.* 172: 3335–3345.
Reed J. W., Purvis M. B., Kingston D. G. I., Biot A., and Gosselé F. (1989) *J. Org. Chem.* 54: 1161–1165.
Staden R. and McLachlan A. D. (1982) *Nucleic Acids Res.*, 10: 141–156.
Schindler U., Sans N., and Schröder J. (1989) *J. Bact.* 171: 847–854.
Thorson J. S., Lo S. F., and Liu H-W (1993) *J. Am. Chem. Soc.* 115: 6993–6994.
Videau D. (1982) *Path. Biol.*, 30: 529–534.

What is claimed is:
1. A compound of formula I

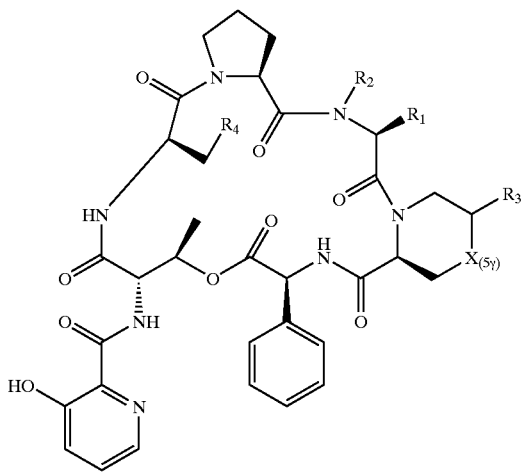

wherein:
R$_2$ and R$_4$ are, independently of each other, a hydrogen atom or a methyl group;
R$_3$ is a hydrogen atom or a hydroxyl group;
X is a CO, CHOH or CH$_2$ group; and
R$_1$ is:

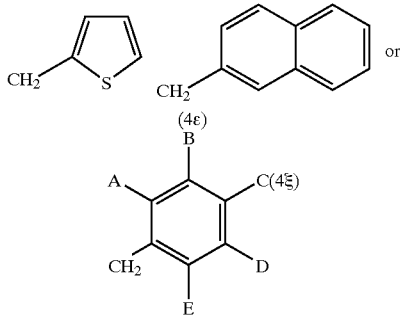

wherein
A, C, D, and E each is a hydrogen atom, and B is:
  a halogen,
  a monoalkylamino or dialkylamino group,
  an ether group,
  a thioether group,
  a C$_1$ to C$_3$ alkyl group, or
  a trihalogenomethyl group, or:
A, B, D, and E each is a hydrogen atom, and C is:
  a halogen,
  an NR$_1$R$_2$ group, wherein R$_1$ and R$_2$ each is, independently of one another, a group selected from
    hydrogen,
    a straight-chain or branched C$_1$ to C$_4$ alkyl group wherein if one of the substituents R$_1$ or R$_2$ is a methyl group, the other necessarily is an ethyl group,
    an alkyl-cycloalkylmethyl group, wherein said cycloalkyl is a C$_3$ to C$_4$ cycloalkyl,
    a substituted or unsubstituted C$_3$ to C$_4$ cycloalkyl group,
    a straight-chain or branched C$_2$ to C$_4$ alkenyl group, wherein if one of the substituents R$_1$ to R$_2$ is an alkenyl group, the other is not a methyl group and is not a C$_3$ to C$_6$ cycloalkyl group,
  a substituted or unsubstituted N-pyrrolidinyl group,
  an ether group,
  a thioether group,
  an acyl or alkoxycarbonyl group,
  a C$_1$ to C$_6$ alkyl group, wherein said alkyl group is straight-chain or branched,
  an alkythiomethyl group,
  an aryl group, or
  a trihalogenomethyl group, and or:
A, D, and E each is a hydrogen atom, and B is:
  a halogen,
  a monoalkylamino or dialkylamino group,
  an ether group
  a thioether group,
  a C$_1$ to C$_3$ alkyl group, and C is:
  a halogen,
  an amino, monoalkylamino or dialkylamino group, with the proviso that B is not a bromine atom, a chlorine atom, or a substituted or unsubstituted allyl group,
  an ether group,
  a thioether group,
  a C$_1$ to C$_6$ alkyl group, or
  a trihalogenomethyl group, and or:
B, E, and D each is a hydrogen atom, and A and C each is a methyl group.

2. A compound according to claim 1, wherein said compound is chosen from:

4ζ-methylthio-de(4ζ-dimethylamino)pristinamycin I$_\lambda$;
4ζ-methyl-de(4ζ-dimethylamino)pristinamycin I$_\lambda$;
4ζ-methoxy-de(4ζ-dimethylamino)pristinamycin I$_\lambda$;
4ζ-methoxycarbonyl-de(4ζ-dimethylamino)pristinamycin I$_\lambda$;
4ζ-chloro-de(4ζ-dimethylamino)pristinamycin I$_\lambda$;
4ζ-bromo-de(4ζ-dimethylamino)pristinamycin I$_\lambda$;
4ζ-iodo-de(4ζ-dimethylamino)pristinamycin I$_\lambda$;
4ζ-trifluoromethyl-de(4ζ-dimethylamino)pristinamycin I$_\lambda$;
4ζ-tert-butyl-de(4ζ-dimethylamino)pristinamycin I$_\lambda$;
4ζ-isopropyl-de(4ζ-dimethylamino)pristinamycin I$_\lambda$;
4ε-methylamino-de(4ζ-dimethylamino)pristinamycin I$_\lambda$;
4ζ-ethylamino-de(4ζ-dimethylamino)pristinamycin I$_\lambda$;
4ζ-diethylamino-de(4ζ-dimethylamino)pristinamycin I$_\lambda$;
4ζ-allylamino-de(4ζ-dimethylamino)pristinamycin I$_\lambda$;
4ζ-diallylamino-de(4ζ-dimethylamino)pristinamycin I$_\lambda$; and
4ζ-allylethylamino-de(4ζ-dimethylamino)pristinamycin I$_\lambda$.

3. A compound according to claim 1, wherein said compound is chosen from:

4ζ-ethylpropylamino-de(4ζ-dimethylamino)pristinamycin I$_\lambda$;
4ζ-ethylisopropylamino-de(4ζ-dimethylamino) pristinamycin I$_\lambda$;
4ζ-ethylmethylcyclopropylamino-de(4ζ-dimethylamino) pristinamycin I$_\lambda$;
4ζ-(1pyrrolidinyl)-de(4ζ-dimethylamino)pristinamycin I$_\lambda$;
4ζ-trifluoromethoxy-de(4ζ-dimethylamino)pristinamycin I$_\lambda$;
4ζ-allyloxy-de(4ζ-dimethylamino)pristinamycin I$_\lambda$;
4ζ-ethoxy-de(4ζ-dimethylamino)pristinamycin I$_\lambda$;
4ζ-ethylthio-de(4ζ-dimethylamino)pristinamycin I$_\lambda$;
4ζ-methylthiomethyl-de(4ζ-dimethylamino)pristinamycin I$_\lambda$;
4ζ-(2-chloroethoxy)-de(4ζ-dimethylamino)pristinamycin I$_\lambda$;

4ζ-acetyl-de(4ζ-dimethylamino)pristinamycin I$_\lambda$;
4ζ-ethyl-de(4ζ-dimethylamino)pristinamycin I$_\lambda$;
4ζ-dimethylamino-de(4ζ-dimethylamino)pristinamycin I$_\lambda$;
4ε-methylthio-de(4ζ-dimethylamino)pristinamycin I$_\lambda$; and
4ε-ethoxy-de(4ζ-dimethylamino)pristinamycin I$_\lambda$.

4. A compound according to claim 1, wherein said compound is chosen from:

4ζ-methylthio-de(4ζ-dimethylamino)pristinamycin I$_H$;
5γ-hydroxy-4ζ-methylthio-de(4ζ-dimethylamino) pristinamycin I$_H$;
4ζ-methyl-de(4ζ-dimethylamino)pristinamycin I$_H$;
4ζ-bromo-de(4ζ-dimethylamino)pristinamycin I$_H$;
4ζ-iodo-de(4ζ-dimethylamino)pristinamycin I$_H$;
4ζ-trifluoromethyl-de(44dimethylamino)pristinamycin I$_H$;
4ε-methoxy-de(4ζ-dimethylamino)pristinamycin I$_H$; and
4ζ-ethyl-de(4ζ-dimethylamino)pristinamycin I$_H$.

5. A compound according to claim 1, wherein said compound is chosen from:

4ζ-isopropyl-de(4ζ-dimethylamino)pristinamycin I$_E$;
4ε-methoxy-de(4ζ-dimethylamino)pristinamycin I$_A$;
4ε-fluoro 4ζ-methyl-de(4ζ-dimethylamino)pristinamycin I$_A$; and
4ζ-amino-de(4ζ-dimethylamino)pristinamycin I$_A$.

6. A compound, wherein said compound is chosen from:

4-trifluoromethoxyphenylalanine;
3-methylaminophenylalanine;
3-methylthiophenylalanine;
3-fluoro-4-methylphenylalanine;
4-methylaminophenylpyruvic acid;
3-ethoxyphenylalanine;
4-allylaminophenylalanine;
4-diallylaminophenylalanine;
4-allylethylaminophenylalanine;
4-ethylpropylaminophenylalanine;
4-ethylisopropylaminophenylalanine;
4-ethylmethylcyclopropylaminophenylalanine;
4-(1-pyrrolidinyl)phenylalanine;
4-ethylthiomethylphenylalanine;
4-O-(2-chloroethyl)tyrosine;
3-dimethylaminophenylalanine; and
3-ethylaminophenylalanine.

7. A pharmaceutical composition, comprising at least one compound according to claim 1 and at least one pharmaceutically acceptable excipient.

8. A pharmaceutical composition, comprising at least one compound according to claim 2 and at least one pharmaceutically acceptable excipient.

9. A pharmaceutical composition, comprising at least one compound according to claim 3 and at least one pharmaceutically acceptable excipient.

10. A pharmaceutical composition, comprising at least one compound according to claim 4 and at least one pharmaceutically acceptable excipient.

11. A pharmaceutical composition, comprising at least one compound according to claim 5 and at least one pharmaceutically acceptable excipient.

12. The pharmaceutical composition according to claim 7, further comprising a Group A streptogramin.

13. The pharmaceutical composition according to claim 8, further comprising a Group A streptogramin.

14. The pharmaceutical composition according to claim 9, further comprising a Group A streptogramin.

15. The pharmaceutical composition according to claim 10, further comprising a Group A streptogramin.

16. The pharmaceutical composition according to claim 11, further comprising a Group A streptogramin.

17. The compound according to claim 1, wherein, for meta derivatives, B is fluorine.

18. The compound according to claim 1, wherein, for meta derivatives, B is a methyl or ethyl group.

19. The compound according to claim 1, wherein, for meta derivatives, B is a trifluoromethyl group.

20. The compound according to claim 1, wherein, for para derivatives, at least one of $R_1$ and $R_2$ is a methyl, isopropyl, or tert-butyl group.

21. The compound according to claim 1, wherein, for para derivatives, at least one of $R_1$ and $R_2$ is a trifluoromethyl group.

22. The compound according to claim 1, wherein, for meta-para disubstituted derivatives, B is fluorine.

23. The compound according to claim 1, wherein, for meta-para disubstituted derivatives, B is a methyl or ethyl group.

24. The compound according to claim 1, wherein, for meta-para disubstituted derivatives, C is fluorine.

25. The compound according to claim 1, wherein, for meta-para disubstituted derivatives, C is a methyl amino or diakylamino group, wherein at least one of the alkyl groups of the diakylamino group is a methyl group, and B is not a bromine atom, a chlorine atom, or a substituted or unsubstituted allyl group.

26. The compound according to claim 1, wherein, for meta-para disubstituted derivatives, C is a trifluromethyl group.

27. The compound according to claim 1, wherein, for para derivatives, at least one of $R_1$ and $R_2$ is a phenyl group.

* * * * *

SEQUENCE LISTING

<160> NUMBER OF SEQ ID NOS: 17

<210> SEQ ID NO 1
<211> LENGTH: 2888
<212> TYPE: DNA
<213> ORGANISM: Streptomyces pristinaespiralis

<400> SEQUENCE: 1

```
ctgcagttcc ccggggccac cgtgctcagc tcctcacccg aacggttcct gcgcatcggc      60
gcggacggct gggcggagtc caaacccatc aagggcaccc gccccgcgg cgccggcccc     120 gcccaggacg ccgccgtcaa ggcctccctc gccgcggccg agaaggaccg cagcgagaac     180
ctgatgatcg tcgacctggt ccgcaacgac ctcggccagg tctgcgacat cggctccgtc     240
cacgtaccgg gcctgttcga ggtggagacc tacgccaccg tccaccagct cgtcagcacg     300
gtccgcggcc gcctggcggc cgacgtctcc cgccccgcg cggtacgggc cgccttcccc     360
ggcgggtcga tgaccggcgc gcccaaggtc cgcaccatgc agttcatcga ccggctcgag     420
aagggcccgc gcggcgtgta ctcggcgcg ctgggctact tcgccctcag cggcgcggcc     480
gacctcagca tcgtcatccg caccatcgtc gccaccgagg aggccgccac catcggcgtg     540
ggcggcgccg tcgtcgccct gtccgacccc gacgacgagg tccgcgaaat gctcctcaag     600
gcgcagacca ccctcgccgc cctgcgccag gcacacgcgg gcgccaccgc ctcggaccgt     660
gaactcctgg ccggcagcct gcggtgaccc acccaccgcc ccaccccggc caccgcaacc     720
ccggctcacc cccggggcgg ccgcgcgcgg tgccgcccgg cggccgaccc ggcgacgggt     780
ccgctcgcgg accgggtgac ggaccggcg gcggggccgg cggcgggccg ggacgtgggc     840
```

```
cgggacgtgg gcccggcgtc cccggcgacc ggcacggcgg cgggcccgga cgtgggcccg     900
gcgtgcccgg cgaccggcac ggtggcgggg cggggcgggg gacggtcagt gcagggcggt     960
gaacatccgc gcgcacagcc gttccagctc cgcgccgtgc tcgcccagca caccgcgcag    1020
ttcggcgaac agggcggcga acgtctcctc gtcgcccctc tcgacggcct gccccagccg    1080
caccaggccg cggcccagcg cctgccgcgc ggccggcgcg ccggggttgg cggcctggat    1140
gtcgaaatac acctccggcg tcccgccggc gatccgggcc agcagcgcca gcatcgccag    1200
atgcggcggc ggggcactgt cccgcagcgc ccccacgtcc accgacagct cacccaggcc    1260
cagcccgaag gccagcaccg cggcatgcgt ggcggcctgc tgcgcggcgg tcagctcgtc    1320
gtgccgccgc gccggcatct ccaccacccg ggcccccac ccggccacca gctccaccag    1380
ggcccgcaca ccgggcccgt cggtgaccac caccgccgcc accggccgcc cctgaagacc    1440
cagcgagggg gcgaacatcg ggttcagccc caccgcctgc agcccggcg ccgcctcacg    1500
cagccgcccg gcgatccggc tcttgaccga caaggtgtcc gcgagcaccg caccgggccg    1560
catcaccccc gccagcacct ccaccgcctc ccacgccacc ggctccggca ccgccagcac    1620
caccacgtcc gccgccgcca gcgccgcgac cgcctccggc cccggccgcc gcacatcacc    1680
ggccaccacc cgcaccccgt ccgccgcacc ggccccggcc acgtccagcc aggtcaccgc    1740
cacccccgaa cgcaccagcc agtggctgaa catgcgcccc accgcaccgg ccccgcccac    1800
caccacacaa cgcccgaaca ccgaaccacc cctcatccgc gttcccgatc ccccggtac    1860
ggaggaagaa ccatgacccc gcccgccatc cccgccgccc cgcccgccac cgggcccgcc    1920
cccgccaccg accccctcga cgcgctgcgc gcccgcctgg acgccgcgga cgccgccctg    1980
ctggacgccg tccgcacacg cctggacatc tgcctgcgca tcggcgagta caagcgcctc    2040
caccaggtgc cgatgatgca gccccaccgg atcgcccagg tccacgccaa cgccgcccgc    2100
tacgccgccg accacggcat cgaccccgcc ttcctgcgca ccctgtacga cacgatcatc    2160
accgagacct gccgcctcga ggacgagtgg atcgcctccg gcggcgcccc cgtcccacg    2220
cccgtgcacg cgtccgcgtc cgcgcggggg gccgtgtcgt gaccgccgcc gcacccaccc    2280
tcgcccaggc gctggacgag gccaccgggc agctgaccgg cgccgggatc accgccgacg    2340
ccgcccgggc cgacacccgg ctgctggccg cccacgcctg ccaggtcgcc ccggggggacc    2400
tcgacacctg cctggccggc ccggtgccgc cccggttctg gcactacgtc cggcgccgtc    2460
tgacccgcga acccgccgaa cgcatcgtcg gccacgccta cttcatgggc caccgcttcg    2520
acctggcccc cggcgtcttc gtccccaaac ccgagaccga ggagatcacc cgggacgcca    2580
tcgcccgcct ggaggccctc gtccgccgcg caccaccgc accccctggtc gtcgacctgt    2640
gcgccggacc gggcaccatg gccgtcaccc tggcccgcca cgtaccggcc gcccgcgtcc    2700
tgggcatcga actctcccag gccgccgccc gcgccgcccg gcgcaacgcc gcggcaccg    2760
gcgcccgcat cgtgcagggc gacgcccgcg acgccttccc cgaactgagc ggcaccgtcg    2820
acctcgtcgt caccaacccg ccctacatcc ccatcggact gcgcacctcc gcacccgaag    2880
tgctcgag                                                             2888
```

<210> SEQ ID NO 2
<211> LENGTH: 888
<212> TYPE: DNA
<213> ORGANISM: Streptomyces pristinaespiralis

<400> SEQUENCE: 2

-continued

```
atgagggtg gttcggtgtt cgggcgttgt gtggtggtgg gcggggccgg tgcggtgggc    60
cgcatgttca gccactggct ggtgcgttcg ggggtggcgg tgacctggct ggacgtggcc   120
ggggccggtg cggcggacgg ggtgcgggtg gtggccggtg atgtgcggcg gccggggccg   180
gaggcggtcg cggcgctggc ggcggcggac gtggtggtgc tggcggtgcc ggagccggtg   240
gcgtgggagg cggtggaggt gctggcgggg gtgatgcggc ccggtgcggt gctcgcggac   300
accttgtcgg tcaagagccg gatcgccggg cggctgcgtg aggcggcgcc ggggctgcag   360
gcggtggggc tgaacccgat gttcgccccc tcgctgggtc ttcaggggcg gccggtggcg   420
gcggtggtgg tcaccgacgg gcccggtgtg cgggccctgg tggagctggt ggccgggtgg   480
ggggcccggg tggtggagat gccggcgcgg cggcacgacg agctgaccgc cgcgcagcag   540
gccgccacgc atgccgcggt gctggccttc gggctgggcc tgggtgagct gtcggtggac   600
gtgggggcgc tgcgggacag tgccccgccg ccgcatctgg cgatgctggc gctgctggcc   660
cggatcgccg gcgggacgcc ggaggtgtat ttcgacatcc aggccgccaa ccccggcgcg   720
ccggccgcgc ggcaggcgct gggccgcggc ctggtgcggc tggggcaggc cgtcgagagg   780
ggcgacgagg agacgttcgc cgccctgttc gccgaactgc gcggtgtgct gggcgagcac   840
ggcgcggagc tggaacggct gtgcgcgcgg atgttcaccg ccctgcac                888
```

<210> SEQ ID NO 3
<211> LENGTH: 297
<212> TYPE: PRT
<213> ORGANISM: Streptomyces pristinaespiralis

<400> SEQUENCE: 3

```
Met Arg Gly Gly Ser Val Phe Gly Arg Cys Val Val Gly Ala
 1               5                  10                  15

Gly Ala Val Gly Arg Met Phe Ser His Trp Leu Val Arg Ser Gly Val
                20                  25                  30

Ala Val Thr Trp Leu Asp Val Ala Gly Ala Gly Ala Ala Asp Gly Val
            35                  40                  45

Arg Val Val Ala Gly Asp Val Arg Arg Pro Gly Pro Glu Ala Val Ala
        50                  55                  60

Ala Leu Ala Ala Ala Asp Val Val Val Leu Ala Val Pro Glu Pro Val
    65                  70                  75                  80

Ala Trp Glu Ala Val Glu Val Leu Ala Gly Val Met Arg Pro Gly Ala
                85                  90                  95

Val Leu Ala Asp Thr Leu Ser Val Lys Ser Arg Ile Ala Gly Arg Leu
            100                 105                 110

Arg Glu Ala Ala Pro Gly Leu Gln Ala Val Gly Leu Asn Pro Met Phe
        115                 120                 125

Ala Pro Ser Leu Gly Leu Gln Gly Arg Pro Val Ala Ala Val Val Val
    130                 135                 140

Thr Asp Gly Pro Gly Val Arg Ala Leu Val Glu Leu Val Ala Gly Trp
145                 150                 155                 160

Gly Ala Arg Val Val Glu Met Pro Ala Arg Arg His Asp Glu Leu Thr
                165                 170                 175

Ala Ala Gln Gln Ala Ala Thr His Ala Ala Val Leu Ala Phe Gly Leu
            180                 185                 190

Gly Leu Gly Glu Leu Ser Val Asp Val Gly Ala Leu Arg Asp Ser Ala
        195                 200                 205

Pro Pro Pro His Leu Ala Met Leu Ala Leu Leu Ala Arg Ile Ala Gly
    210                 215                 220
```

```
Gly Thr Pro Glu Val Tyr Phe Asp Ile Gln Ala Ala Asn Pro Gly Ala
225                 230                 235                 240

Pro Ala Ala Arg Gln Ala Leu Gly Arg Gly Leu Val Arg Leu Gly Gln
            245                 250                 255

Ala Val Glu Arg Gly Asp Glu Glu Thr Phe Ala Ala Leu Phe Ala Glu
        260                 265                 270

Leu Arg Gly Val Leu Gly Glu His Gly Ala Glu Leu Glu Arg Leu Cys
    275                 280                 285

Ala Arg Met Phe Thr Ala Leu His Pro
290                 295

<210> SEQ ID NO 4
<211> LENGTH: 387
<212> TYPE: DNA
<213> ORGANISM: Streptomyces pristinaespiralis

<400> SEQUENCE: 4
atgaccccgc cgccatccc cgccgccccg cccgccaccg ggcccgcccc cgccaccgac      60 ccctcgacg cgctgcgcgc cgcctggac gccgcggacg ccgccctgct ggacgccgtc     120
cgcacacgcc tggacatctg cctgcgcatc ggcgagtaca agcgcctcca ccaggtgccg    180
atgatgcagc cccaccggat cgcccaggtc acgccaacg ccgcccgcta cgccgccgac    240
cacggcatcg accccgcctt cctgcgcacc ctgtacgaca cgatcatcac cgagacctgc    300
cgcctcgagg acgagtggat cgcctccggc ggcgcccccg tccccacgcc cgtgcacgcg    360
tccgcgtccg cgcgggggc cgtgtcg                                         387

<210> SEQ ID NO 5
<211> LENGTH: 130
<212> TYPE: PRT
<213> ORGANISM: Streptomyces pristinaespiralis

<400> SEQUENCE: 5

Met Thr Pro Pro Ala Ile Pro Ala Ala Pro Ala Thr Gly Pro Ala
1               5                   10                  15

Ala Ala Thr Asp Pro Leu Asp Ala Leu Arg Ala Arg Leu Asp Ala Ala
            20                  25                  30

Asp Ala Ala Leu Leu Asp Ala Val Arg Thr Arg Leu Asp Ile Cys Leu
        35                  40                  45

Arg Ile Gly Glu Tyr Lys Arg Leu His Gln Val Pro Met Met Gln Pro
    50                  55                  60

His Arg Ile Ala Gln Val His Ala Asn Ala Ala Arg Tyr Ala Ala Asp
65                  70                  75                  80

His Gly Ile Asp Pro Ala Phe Leu Arg Thr Leu Tyr Asp Thr Ile Ile
                85                  90                  95

Thr Glu Thr Cys Arg Leu Glu Asp Glu Trp Ile Ala Ser Gly Gly Ala
            100                 105                 110

Pro Val Pro Thr Pro Val His Ala Ser Ala Ser Ala Arg Gly Ala Val
        115                 120                 125

Ser Pro
    130

<210> SEQ ID NO 6
<211> LENGTH: 4496
<212> TYPE: DNA
<213> ORGANISM: Streptomyces pristinaespiralis
```

-continued

```
<400> SEQUENCE: 6
ctcgagcagg tgccccacct cggcggcacg gtgcgcgggc agcgcgaaca ccggcagcgc      60
gcccagacgg aacagcgcga agcacaccgc gacgaactcg ggcgtgttcg gcagctgcac     120
cagcacccgc tcgccggcgc cgatcccgcg cgccgcgaac cccgccgcca gccggtcgca     180
ccagcggtcc agggcacggt aggtgacacg ggagcacccg tccgcgccga ccagcgcctc     240
ccgctcgccg tactgctccg cccagcggcc cagcagcatg cccagcggct cgccccgcca     300
gtagccggcc gcccggtact cgcggccac atcctcgggc agggaacgc atccgtccag       360 catcgttggt cctttccggc ttcgtcctcg cgtcgcgccc agtgtcggca gcgccgttga     420
cacgccgctg atgcgccgcg cccgcgcgcc gccgctccgt caggagccga tcagggcggc     480
gtcagccggg ccggacagga tgccgcccac ggggcccggc acaccgggcc gcggcgacag     540
cgggccggcg accggcaggc cgacaccacg cacggacgag aagaaacaac acaaggggag     600
cacccgatgg agacctgggt cctgggccgg cgcgacgtcg ccgaggtggt ggccgccgtc     660
ggccgcgacg aactcatgcg ccgcatcatc gaccgcctca ccggcggact ggccgagatc     720
ggccgcggcc agcggcacct gtccccgctg cgcggcggac tggaacgcag cgaacccgtg     780
cccggcatct gggaatggat gccgcaccgc gaacccggcg accacatcac cctcaagacc     840
gtcggctaca gccccgccaa ccccggccgc ttcggcctgc cgaccatcct gggcaccgtc     900
gcccgctacg acgacaccac cggcgccctg accgccctga tggacggcgt gctgctcacc     960
gccctgcgca ccggcgccgc ctccgccgtc gcctcccgcc tgctggcccg ccccgacagc    1020
cacaccctgg gactgatcgg caccggcgcc caggccgtca cccaactgca cgccctgtcc    1080
ctggtactgc ccctgcaacg ggccctggtg tgggacaccg accccgccca ccgggaaagc    1140
ttcgcccggc gcgccgcgtt caccggcgtc agcgtcgaga tcgccgagcc cgcccggatc    1200
gccgccgagg ccgacgtcat ctccaccgcc acctcggtag ccgtcggcca gggcccggtc    1260
ctgcccgaca ccggcgtccg cgagcacctg cacatcaacg ccgtcggcgc ggacctcgtc    1320
ggcaagacgg aactgccgct cggcctgctc gagcgggcgt tcgtcaccgc cgaccacccc    1380
gagcaggcgc tgcgcgaggg cgagtgccag caactctccg ccgaccggct cggccgcag    1440 ctggcccacc tgtgcgccga cccggcggcc gccgccggcc ggcaggacac cctgagcgtc    1500
ttcgactcca ccggcttcgc cttcgaggac gccctggcga tggaagtgtt cctcgaggcc    1560
gccgccgaac gggacctggg catccgggtg ggcatcgaac accacccgg cgacgccctg     1620 gaccctacg cccctccagcc cctgcccctg ccctggccg ccccgccca ctgaccccc       1680 cctttttcg ggaccccgc tcttttcga gacccccgcc cggccggccc ggccctcctc      1740
ccgccggccc ccatgcccgg ccgggccggg gcacccacga cgcccctcgcg aggagagaga   1800 tgcccccac ccccggccc accaccgacg acggcggccg tgaactgctc gcctggctgc      1860
gcgagatgcg ccaccaccac cccgtccacg aggacgaata cggtgccttc cacgtcttcc    1920
ggcacgccga cgtcctcacc gtcgcctccg accccggcgt ctactcctcc cagctcagcc    1980
ggctacggcc cggctcccag gcgttgagcg aacagatcct gtcggtcatc gacccgccga    2040
tgcaccgcac cctgcgccgc ctggtcagcc aggccttcac ccccgcacc gtcgccgacc     2100 tcgaaccacg cgtcaccgaa ctggccgggc aactgctcga cgccgtcgac ggcgacacgt    2160
tcgacctcgt cgccgacttc gcctacccgc tgcccgtgat cgtgatcgcc gaactcctcg    2220
gcgtgccgcc cgccgaccgc accctgttcc gctcctggtc cgaccggatg ctgcagatgc    2280
aggtcgccga cccggcggac atgcagttcg gcgacgacgc cgacgaggac taccaacgcc    2340
```

-continued

```
tcgtcaaaga acccatgcgc gccatgcacg cctacctcca cgaccacgtc accgaccgcc       2400
gcgcccgccc cgcgaacgac ctgatctccg cactcgtcgc cgcccgcgtg gagggcgaac       2460
gactcaccga cgagcagatc gtcgaattcg gggcgctgct gctgatggcc ggccacgtct       2520
ccacctccat gctgctcggc aacaccgtgc tgtgcctgaa ggaccacccc cgggccgagg       2580
ccgccgcccg cgccgaccgg tccctgatcc ccgccctgat cgaagaagta ctgcggctgc       2640
ggccgccgat caccgtcatg gcccgcgtca ccaccaagga caccgtcctc gccggcacca       2700
ccatccccgc cggacgcatg gtcgtgccct ccctgctgtc cgccaaccac gacgaacagg       2760
tcttcaccga ccccgaccac ctcgacctcg cccgcgaagg ccgccagatc gccttcggcc       2820
acggcatcca ctactgcctg ggcgccccgc tcgcccgcct ggagggccgc atcgccctgg       2880
aagccctctt cgaccgattc cccgacttct cgcccaccga cggcgcaaaa ctgcgctacc       2940
accgcgacgg actgttcggc gtcaagaacc tgccgctgac cgtacggcgc ggctgacaca       3000
gacaaggggg ccacctggtg cgcaccgtgc gaaccctgct gatcgacaac tacgactcgt       3060
tcacctacaa cctcttccag atgctggccg aggtgaacgg cgccgctccg ctcgtcgtcc       3120
gcaacgacga cacccgcacc tggcaggccc tggcgccggg cgacttcgac aacgtcgtcg       3180
tctcacccgg ccccggccac cccgccaccg acaccgacct gggcctcagc cgccgggtga       3240
tcaccgaatg ggacctgccg ctgctcgggg tgtgcctggg ccaccaggcc ctgtgcctgc       3300
tcgccggcgc cgccgtcgtc cacgcacccg aaccctttca cggccgcacc agcgacatcc       3360
gccacgacgg gcagggcctg ttcgcgaaca tcccctcccc gctgaccgtg gtccgctacc       3420
actcgctgac cgtccggcaa ctgcccgccg acctgcgcgc caccgcccac accgccgacg       3480
ggcagctgat ggccgtcgcc caccgccacc tgccccgctt cggcgtgcag ttccaccccg       3540
aatcgatcag cagcgaacac ggccaccgga tgctcgccaa cttcgcgcga ctgtccctgc       3600
gcgcggccgg ccaccgcccc ccgcacaccg aacgcatacc cgcacccgca cccgcccccg       3660
cccccgcccc cgcaccggca ccgcccgcgt ccgcgccggt gggggagtac cggctgcatg       3720
tgcgcgaggt cgcctgcgtg cccgacgcgg acgccgcgtt caccgccctg ttcgccgacg       3780
ccccggcccg gttctggctc gacagcagcc gcgtcgagcc gggcctcgcc cgcttcacct       3840
tcctcggcgc ccccgccggc ccgctcggcg aacagatcac ctacgacgtc gccgaccggg       3900
ccgtgcgcgt caaggacggt tcaggcggcg agacccgccg gcccggcacc ctcttcgacc       3960
acctggaaca cgaactggcc gcccgcgccc tgcccgccac cggcctgccc ttcgagttca       4020
acctcggcta cgtcggctac ctcggctacg agaccaaggc cgacagcggc ggcgaggacg       4080
cccaccgcgg cgaactgccc gacggcgcct tcatgttcgc cgaccggatg ctcgccctcg       4140
accacgaaca ggggcgggcc tggctcctgg cactgagcag cacccgacgg cccgccaccg       4200
cacccgccgc cgaacgctgg ctcaccgacg ccgcccggac cctcgccacc accgcccccg       4260
gcccgccctt caccctgctg cccgacgacc aactgcccgc cctggacgtc cactaccgcc       4320
acagcctgcc ccgctaccgg gaactggtcg aggaatgccg ccgcctgatc accgacggcg       4380
agacctacga ggtgtgcctg acgaacatgc tccgggtgcc cggccggatc gacccgctca       4440
ccgcctaccg cgccctgcgc accgtcagcc ccgcccccta cgccgcctac ctgcag         4496
```

<210> SEQ ID NO 7
<211> LENGTH: 1065
<212> TYPE: DNA
<213> ORGANISM: Streptomyces pristinaespiralis

<400> SEQUENCE: 7

```
atggagacct gggtcctggg ccggcgcgac gtcgccgagg tggtggccgc cgtcggccgc      60
gacgaactca tgcgccgcat catcgaccgc ctcaccggcg gactggccga gatcggccgc     120
ggcgagcggc acctgtcccc gctgcgcggc ggactggaac gcagcgaacc cgtgcccggc     180
atctgggaat ggatgccgca ccgcgaaccc ggcgaccaca tcaccctcaa gaccgtcggc     240
tacagccccg ccaaccccgg ccgcttcggc ctgccgacca cctgggcac cgtcgcccgc     300
tacgacgaca ccaccggcgc cctgaccgcc ctgatggacg gcgtgctgct caccgccctg     360
cgcaccggcg ccgcctccgc cgtcgcctcc cgcctgctgg cccgccccga cagccacacc     420
ctgggactga tcggcaccgg cgcccaggcc gtcacccaac tgcacgccct gtccctggta     480
ctgcccctgc aacgggccct ggtgtgggac accgaccccg cccaccggga agcttcgcc      540
cggcgcgccg cgttcaccgg cgtcagcgtc gagatcgccg agcccgcccg gatcgccgcc     600
gaggccgacg tcatctccac cgccacctcg gtagccgtcg gccagggccc ggtcctgccc     660
gacaccggcg tccgcgagca cctgcacatc aacgccgtcg gcgcggacct cgtcggcaag     720
acggaactgc cgctcggcct gctcgagcgg cgttcgtca ccgccgacca ccccgagcag      780
gcgctgcgcg agggcgagtg ccagcaactc tccgccgacc ggctcggccc gcagctggcc     840
cacctgtgcg ccgaccccgc ggccgccgcc ggccggcagg acaccctgag cgtcttcgac     900
tccaccggct cgccttcga ggacgccctg cgcatggaag tgttcctcga ggccgccgcc      960
gaacgggacc tgggcatccg ggtgggcatc gaacaccacc ccggcgacgc cctggacccc    1020
tacgccctcc agcccctgcc cctgcccctg ccgccccccg cccac                    1065
```

<210> SEQ ID NO 8
<211> LENGTH: 356
<212> TYPE: PRT
<213> ORGANISM: Streptomyces pristinaespiralis

<400> SEQUENCE: 8

```
Met Glu Thr Trp Val Leu Gly Arg Arg Asp Val Ala Glu Val Val Ala
  1               5                  10                  15

Ala Val Gly Arg Asp Glu Leu Met Arg Arg Ile Ile Asp Arg Leu Thr
             20                  25                  30

Gly Gly Leu Ala Glu Ile Gly Arg Gly Glu Arg His Leu Ser Pro Leu
         35                  40                  45

Arg Gly Gly Leu Glu Arg Ser Glu Pro Val Pro Gly Ile Trp Glu Trp
     50                  55                  60

Met Pro His Arg Glu Pro Gly Asp His Ile Thr Leu Lys Thr Val Gly
 65                  70                  75                  80

Tyr Ser Pro Ala Asn Pro Gly Arg Phe Gly Leu Pro Thr Ile Leu Gly
                 85                  90                  95

Thr Val Ala Arg Tyr Asp Asp Thr Thr Gly Ala Leu Thr Ala Leu Met
            100                 105                 110

Asp Gly Val Leu Leu Thr Ala Leu Arg Thr Gly Ala Ala Ser Ala Val
        115                 120                 125

Ala Ser Arg Leu Leu Ala Arg Pro Asp Ser His Thr Leu Gly Leu Ile
    130                 135                 140

Gly Thr Gly Ala Gln Ala Val Thr Gln Leu His Ala Leu Ser Leu Val
145                 150                 155                 160

Leu Pro Leu Gln Arg Ala Leu Val Trp Asp Thr Asp Pro Ala His Arg
                165                 170                 175
```

```
Glu Ser Phe Ala Arg Arg Ala Ala Phe Thr Gly Val Ser Val Glu Ile
            180                 185                 190

Ala Glu Pro Ala Arg Ile Ala Ala Glu Ala Asp Val Ile Ser Thr Ala
        195                 200                 205

Thr Ser Val Ala Val Gly Gln Gly Pro Val Leu Pro Asp Thr Gly Val
    210                 215                 220

Arg Glu His Leu His Ile Asn Ala Val Gly Ala Asp Leu Val Gly Lys
225             230                 235                 240

Thr Glu Leu Pro Leu Gly Leu Leu Glu Arg Ala Phe Val Thr Ala Asp
                245                 250                 255

His Pro Glu Gln Ala Leu Arg Glu Gly Glu Cys Gln Gln Leu Ser Ala
            260                 265                 270

Asp Arg Leu Gly Pro Gln Leu Ala His Leu Cys Ala Asp Pro Ala Ala
        275                 280                 285

Ala Ala Gly Arg Gln Asp Thr Leu Ser Val Phe Asp Ser Thr Gly Phe
    290                 295                 300

Ala Phe Glu Asp Ala Leu Ala Met Glu Val Phe Leu Glu Ala Ala Ala
305             310                 315                 320

Glu Arg Asp Leu Gly Ile Arg Val Gly Ile Glu His His Pro Gly Asp
                325                 330                 335

Ala Leu Asp Pro Tyr Ala Leu Gln Pro Leu Pro Leu Pro Leu Ala Ala
            340                 345                 350

Pro Ala His Pro
        355

<210> SEQ ID NO 9
<211> LENGTH: 1194
<212> TYPE: DNA
<213> ORGANISM: Streptomyces pristinaespiralis

<400> SEQUENCE: 9 atgccccca cccccggcc caccaccgac gacggcggcc gtgaactgct cgcctggctg      60
cgcgagatgc gccaccacca ccccgtccac gaggacgaat acggtgcctt ccacgtcttc    120
cggcacgccg acgtcctcac cgtcgcctcc gaccccggcg tctactcctc ccagctcagc    180
cggctacggc ccggctccca ggcgttgagc gaacagatcc tgtcggtcat cgacccgccg    240
atgcaccgca ccctgcgccg cctggtcagc caggccttca ccccccgcac cgtcgccgac    300
ctcgaaccac gcgtcaccga actggccggg caactgctcg acgccgtcga cggcgacacg    360
ttcgacctcg tcgccgactt cgcctaccccg ctgcccgtga tcgtgatcgc cgaactcctc    420
ggcgtgccgc ccgccgaccg caccctgttc cgctcctggt ccgaccggat gctgcagatg    480
caggtcgccg accggcgga catgcagttc ggcgacgacg ccgacgagga ctaccaacgc     540
ctcgtcaaag aacccatgcg cgccatgcac gcctacctcc acgaccacgt caccgaccgc    600
cgcgcccgcc ccgcgaacga cctgatctcc gcactcgtcg ccgcccgcgt ggagggcgaa    660
cgactcaccg acgagcagat cgtcgaattc ggggcgctgc tgctgatggc cggccacgtc    720
tccacctcca tgctgctcgg caacaccgtg ctgtgcctga ggaccacccc cgggccgag    780 gccgccgccc gcgccgaccg gtccctgatc cccgccctga tcgaagaagt actgcggctg    840
cggccgccga tcaccgtcat ggcccgcgtc accaccaagg acaccgtcct cgccggcacc    900
accatccccg ccggacgcat ggtcgtgccc tccctgctgt ccgccaacca cgacgaacag    960
gtcttcaccg accccgacca cctcgacctc gcccgcgaag ccgccagat cgccttcggc     1020 cacggcatcc actactgcct gggcgccccg ctcgcccgcc tggagggccg catcgccctg    1080
```

```
gaagccctct tcgaccgatt ccccgacttc tcgcccaccg acggcgcaaa actgcgctac   1140
caccgcgacg gactgttcgg cgtcaagaac ctgccgctga ccgtacggcg cggc         1194
```

<210> SEQ ID NO 10
<211> LENGTH: 399
<212> TYPE: PRT
<213> ORGANISM: Streptomyces pristinaespiralis

<400> SEQUENCE: 10

```
Met Pro Pro Thr Pro Arg Pro Thr Thr Asp Asp Gly Gly Arg Glu Leu
  1               5                  10                  15

Leu Ala Trp Leu Arg Glu Met Arg His His Pro Val His Glu Asp
             20                  25                  30

Glu Tyr Gly Ala Phe His Val Phe Arg His Ala Asp Val Leu Thr Val
             35                  40                  45

Ala Ser Asp Pro Gly Val Tyr Ser Ser Gln Leu Ser Arg Leu Arg Pro
 50                  55                  60

Gly Ser Gln Ala Leu Ser Glu Gln Ile Leu Ser Val Ile Asp Pro Pro
 65                  70                  75                  80

Met His Arg Thr Leu Arg Arg Leu Val Ser Gln Ala Phe Thr Pro Arg
                 85                  90                  95

Thr Val Ala Asp Leu Glu Pro Arg Val Thr Glu Leu Ala Gly Gln Leu
            100                 105                 110

Leu Asp Ala Val Asp Gly Asp Thr Phe Asp Leu Val Ala Asp Phe Ala
            115                 120                 125

Tyr Pro Leu Pro Val Ile Val Ile Ala Glu Leu Leu Gly Val Pro Pro
130                 135                 140

Ala Asp Arg Thr Leu Phe Arg Ser Trp Ser Asp Arg Met Leu Gln Met
145                 150                 155                 160

Gln Val Ala Asp Pro Ala Asp Met Gln Phe Gly Asp Asp Ala Asp Glu
                165                 170                 175

Asp Tyr Gln Arg Leu Val Lys Glu Pro Met Arg Ala Met His Ala Tyr
            180                 185                 190

Leu His Asp His Val Thr Asp Arg Arg Ala Arg Pro Ala Asn Asp Leu
            195                 200                 205

Ile Ser Ala Leu Val Ala Arg Val Glu Gly Glu Arg Leu Thr Asp
            210                 215                 220

Glu Gln Ile Val Glu Phe Gly Ala Leu Leu Leu Met Ala Gly His Val
225                 230                 235                 240

Ser Thr Ser Met Leu Leu Gly Asn Thr Val Leu Cys Leu Lys Asp His
                245                 250                 255

Pro Arg Ala Glu Ala Ala Arg Ala Asp Arg Ser Leu Ile Pro Ala
            260                 265                 270

Leu Ile Glu Glu Val Leu Arg Leu Arg Pro Pro Ile Thr Val Met Ala
            275                 280                 285

Arg Val Thr Thr Lys Asp Thr Val Leu Ala Gly Thr Thr Ile Pro Ala
290                 295                 300

Gly Arg Met Val Val Pro Ser Leu Leu Ser Ala Asn His Asp Glu Gln
305                 310                 315                 320

Val Phe Thr Asp Pro Asp His Leu Asp Leu Ala Arg Glu Gly Arg Gln
                325                 330                 335

Ile Ala Phe Gly His Gly Ile His Tyr Cys Leu Gly Ala Pro Leu Ala
            340                 345                 350
```

```
Arg Leu Glu Gly Arg Ile Ala Leu Glu Ala Leu Phe Asp Arg Phe Pro
        355                 360                 365

Asp Phe Ser Pro Thr Asp Gly Ala Lys Leu Arg Tyr His Arg Asp Gly
    370                 375                 380

Leu Phe Gly Val Lys Asn Leu Pro Leu Thr Val Arg Arg Gly Pro
385                 390                 395

<210> SEQ ID NO 11
<211> LENGTH: 1561
<212> TYPE: DNA
<213> ORGANISM: Streptomyces pristinaespiralis

<400> SEQUENCE: 11
aagcttcccg accgggtgga ggtcgtcgac gcgttcccgc tgaccggcct caacaaggtc      60
gacaagaagg ccctggcggc cgacatcgcc gccaagaccg cccccacccg ccccaccacc     120
gccggccacg gcccgaccac ggacggcgat acggccggtg ggggtgggtc cgcgggcggg     180
gtgacggccg ccggtggcgg cgggaggag gcggcgtgag cgggcccggg cccgagggcg     240
gctaccgggt gccgttcgcg cgacgcggtt cggtggtggg cgaggcggac ctggcggcgc     300
tgggcgaact ggtccgctcg gccggtcgc tgacgtcggg ggtgtggcgg gagcggttcg     360
aggaacagtt cgcccgcctg accggcgccc ggcacgcgct cagtgtcacc agcggcaccg     420
tcgcgctgga actggcggtg cggatgctgg acctggcgcc gggcgacgag gtgatcgcca     480
ccccgcagac gttccaggcg acggtgcagc cgctgctcga ccacgacgtg cggctgcggt     540
tctgcgacat cgacccggac accctcaacc tcgaccggc ggtgctggag acgctgatca     600
ccgaccgcac ccgggcgatc ctgctcgtcc actacggcgg caacccggcc gacatggacc     660
gcatcatggc cctggcccgc aagcgcggca tcatcgtcgt cgaggacagc gcgcacgcgc     720
tgggcgccgt gtaccggggg cggcggccgg gggcactggc ggacatcggc tgcttcactt     780
tccactccac gaagaacatc accaccctcg gcgaggcgg catgatcacc ctgtcgcgtg     840
acgagtgggc ccagcgggtg ggacgtatcc gcgacaacga ggccgacggc gtgtacgcgg     900
cgctgccgga ctccgcgcgg gcgggtgctc cggcgctgct gccgtggatg aagttcgcgg     960
agggtgtgta cggtcaccgg gcggtcgggg tccgcggggc gggcacgaac gcgacgatgt    1020
cggaggcggc ggcggcggtg ggcgtggtgc aactggcgtc gctggagcgg ttcgtggccc    1080
ggcgccggag catcgcgcag cggctggacg aggccgtggc ctcggtggcc ggcacccggc    1140
tgcaccgggc ggcggcggac agtctgcacg cctaccacct gtacacgttc ttcctcaccg    1200
gcggccggca ggtgcgggag cggttcgtgc gcgccctgga ccggctgggt gtggaggtcc    1260
agttgcggta cttcccgctc catctgtcgc ccgagtggcg gctgcgcggc acgggccgg    1320
gcgagtgtcc gacggccgaa cgggtctggt tcgaggagca catgaacctg ccgtgccatc    1380
ccggtctgag tgacgccag gtcgactaca tggtcgaggc ggtcacccgc gccctgcacg    1440
aggcccacgg cacggggacg cgggtggcgg ccgggcacct gtgacaccgt ccgcatccgg    1500
ccggtggttt tccaagaccg agggagaggc aggcgtatgc cgttcatcga agtgaagatc    1560
t                                                                    1561

<210> SEQ ID NO 12
<211> LENGTH: 1233
<212> TYPE: DNA
<213> ORGANISM: Streptomyces pristinaespiralis

<400> SEQUENCE: 12
```

-continued

```
gtgccgttcg cgcgacgcgg ttcggtggtg ggcgaggcgg acctggcggc gctgggcgaa        60
ctggtccgct cgggccggtc gctgacgtcg ggggtgtggc gggagcggtt cgaggaacag       120
ttcgcccgcc tgaccggcgc ccggcacgcg ctcagtgtca ccagcggcac cgtcgcgctg       180
gaactggcgg tgcggatgct ggacctggcg ccgggcgacg aggtgatcgc cacccccgcag      240
acgttccagg cgacggtgca gccgctgctc gaccacgacg tgcggctgcg gttctgcgac       300
atcgacccgg acaccctcaa cctcgacccg gcggtgctgg agacgctgat caccgaccgc       360
acccgggcga tcctgctcgt ccactacggc ggcaacccgg ccgacatgga ccgcatcatg       420
gccctggccc gcaagcgcgg catcatcgtc gtcgaggaca cgcgcacgc gctgggcgcc        480
gtgtaccggg gcggcggcc gggggcactg gcggacatcg gctgcttcac tttccactcc       540
acgaagaaca tcaccaccct cggcgagggc ggcatgatca ccctgtcgcg tgacgagtgg       600
gcccagcggg tgggacgtat ccgcgacaac gaggccgacg gcgtgtacgc ggcgctgccg       660
gactccgcgc gggcgggtgc tccggcgctg ctgccgtgga tgaagttcgc ggagggtgtg       720
tacggtcacc gggcggtcgg ggtccgcggg gcgggcacga acgcgacgat gtcggaggcg       780
gcggcggcgg tgggcgtggt gcaactggcg tcgctggagc ggttcgtggc ccggcgccgg       840
agcatcgcgc agcggctgga cgaggccgtg gcctcggtgg ccggcacccg gctgcaccgg       900
gcggcggcg acagtctgca cgcctaccac ctgtacacgt tcttcctcac cggcggccgg       960
caggtgcggg agcggttcgt gcgcgccctg gaccggctgg gtgtggaggt ccagttgcgg      1020
tacttcccgc tccatctgtc gcccgagtgg cggctgcgcg ccacgggcc gggcgagtgt       1080
ccgacggccg aacgggtctg gttcgaggag cacatgaacc tgccgtgcca tcccggtctg      1140
agtgacggcc aggtcgacta catggtcgag gcggtcaccc gcgccctgca cgaggcccac      1200
ggcacgggga cgcgggtggc ggccgggcac ctg                                    1233
```

<210> SEQ ID NO 13
<211> LENGTH: 412
<212> TYPE: PRT
<213> ORGANISM: Streptomyces pristinaespiralis

<400> SEQUENCE: 13

```
Val Pro Phe Ala Arg Arg Gly Ser Val Val Gly Glu Ala Asp Leu Ala
  1               5                  10                  15

Ala Leu Gly Glu Leu Val Arg Ser Gly Arg Ser Leu Thr Ser Gly Val
             20                  25                  30

Trp Arg Glu Arg Phe Glu Glu Gln Phe Ala Arg Leu Thr Gly Ala Arg
         35                  40                  45

His Ala Leu Ser Val Thr Ser Gly Thr Val Ala Leu Glu Leu Ala Val
     50                  55                  60

Arg Met Leu Asp Leu Ala Pro Gly Asp Glu Val Ile Ala Thr Pro Gln
 65                  70                  75                  80

Thr Phe Gln Ala Thr Val Gln Pro Leu Leu Asp His Asp Val Arg Leu
                 85                  90                  95

Arg Phe Cys Asp Ile Asp Pro Asp Thr Leu Asn Leu Asp Pro Ala Val
            100                 105                 110

Leu Glu Thr Leu Ile Thr Asp Arg Thr Arg Ala Ile Leu Leu Val His
        115                 120                 125

Tyr Gly Gly Asn Pro Ala Asp Met Asp Arg Ile Met Ala Leu Ala Arg
    130                 135                 140

Lys Arg Gly Ile Ile Val Val Glu Asp Ser Ala His Ala Leu Gly Ala
145                 150                 155                 160
```

Val Tyr Arg Gly Arg Arg Pro Gly Ala Leu Ala Asp Ile Gly Cys Phe
                165                 170                 175

Thr Phe His Ser Thr Lys Asn Ile Thr Thr Leu Gly Glu Gly Gly Met
            180                 185                 190

Ile Thr Leu Ser Arg Asp Glu Trp Ala Gln Arg Val Gly Arg Ile Arg
        195                 200                 205

Asp Asn Glu Ala Asp Gly Val Tyr Ala Ala Leu Pro Asp Ser Ala Arg
    210                 215                 220

Ala Gly Ala Pro Ala Leu Leu Pro Trp Met Lys Phe Ala Glu Gly Val
225                 230                 235                 240

Tyr Gly His Arg Ala Val Gly Val Arg Gly Ala Gly Thr Asn Ala Thr
                245                 250                 255

Met Ser Glu Ala Ala Ala Val Gly Val Val Gln Leu Ala Ser Leu
            260                 265                 270

Glu Arg Phe Val Ala Arg Arg Ser Ile Ala Gln Arg Leu Asp Glu
        275                 280                 285

Ala Val Ala Ser Val Ala Gly Thr Arg Leu His Arg Ala Ala Ala Asp
    290                 295                 300

Ser Leu His Ala Tyr His Leu Tyr Thr Phe Phe Leu Thr Gly Gly Arg
305                 310                 315                 320

Gln Val Arg Glu Arg Phe Val Arg Ala Leu Asp Arg Leu Gly Val Glu
                325                 330                 335

Val Gln Leu Arg Tyr Phe Pro Leu His Leu Ser Pro Glu Trp Arg Leu
            340                 345                 350

Arg Gly His Gly Pro Gly Glu Cys Pro Thr Ala Glu Arg Val Trp Phe
        355                 360                 365

Glu Glu His Met Asn Leu Pro Cys His Pro Gly Leu Ser Asp Gly Gln
    370                 375                 380

Val Asp Tyr Met Val Glu Ala Val Thr Arg Ala Leu His Glu Ala His
385                 390                 395                 400

Gly Thr Gly Thr Arg Val Ala Ala Gly His Leu Pro
                405                 410

<210> SEQ ID NO 14
<211> LENGTH: 2220
<212> TYPE: DNA
<213> ORGANISM: Streptomyces pristinaespiralis

<400> SEQUENCE: 14
ggcgtcaaga acctgccgct gaccgtacgg cgcggctgac acagacaagg gggccacctg     60
gtgcgcaccg tgcgaaccct gctgatcgac aactacgact cgttcaccta caacctcttc    120
cagatgctgg ccgaggtgaa cggcgccgct ccgctcgtcg tccgcaacga cgacacccgc    180
acctggcagg ccctggcgcc gggcgacttc gacaacgtcg tcgtctcacc cggccccggc    240
caccccgcca ccgacaccga cctgggcctc agccgccggg tgatcaccga atgggacctg    300
ccgctgctcg gggtgtgcct ggccaccag gccctgtgcc tgctcgccgg cgccgccgtc    360
gtccacgcac ccgaacccct tcacggccgc accagcgaca tccgccacga cgggcagggc    420
ctgttcgcga acatcccctc ccgctgaccg tggtccgct accactcgct gaccgtccgg    480
caactgcccg ccgacctgcg cgccaccgcc cacaccgccg acgggcagct gatggccgtc    540
gcccaccgcc acctgccccg cttcggcgtg cagttccacc ccgaatcgat cagcagcgaa    600
cacggccacc ggatgctcgc caacttccgc gacctgtccc tgcgcgcggc cggccaccgc    660

```
cccccgcaca ccgaacgcat acccgcaccc gcacccgccc ccgccccgc ccccgcaccg      720
gcaccgcccg cgtccgcgcc ggtggggag taccggctgc atgtgcgcga ggtcgcctgc       780
gtgcccgacg cggacgccgc gttcaccgcc ctgttcgccg acgccccggc ccggttctgg      840
ctcgacagca gccgcgtcga gccgggcctc gcccgcttca ccttcctcgg cgccccgcc       900
ggcccgctcg gcgaacagat cacctacgac gtcgccgacc gggccgtgcg cgtcaaggac      960
ggttcaggcg gcgagacccg ccggcccggc accctcttcg accacctgga acacgaactg     1020
gccgccgcg ccctgcccgc caccggcctg cccttcgagt tcaacctcgg ctacgtcggc      1080
tacctcggct acgagaccaa ggccgacagc ggcggcgagg acgccaccg cggcgaactg      1140
cccgacggcg ccttcatgtt cgccgaccgg atgctcgccc tcgaccacga acaggggcgg     1200
gcctggctcc tggcactgag cagcaccga cggcccgcca ccgcacccgc cgccgaacgc      1260
tggctcaccg acgccgcccg gaccctcgcc accaccgccc ccgcccgcc cttcaccctg      1320
ctgcccgacg accaactgcc cgccctggac gtccactacc gccacagcct gccccgctac    1380
cgggaactgg tcgaggaatg ccgccgcctg atcaccgacg gcgagaccta cgaggtgtgc    1440
ctgacgaaca tgctccgggt gcccggccgg atcgacccgc tcaccgccta ccgcgccctg    1500
cgcaccgtca gccccgcccc ctacgccgcc tacctgcagt tccccggggc caccgtgctc    1560
agctcctcac ccgaacggtt cctgcgcatc ggcgcggacg gttgggcgga gtccaaaccc    1620
atcaagggca cccgcccccg cggcgccggc cccgcccagg acgccgccgt caaggcctcc    1680
ctcgccgcgg ccgagaagga ccgcagcgag aacctgatga tcgtcgacct ggtccgcaac    1740
gacctcggcc aggtctgcga catcggctcc gtccacgtac cgggcctgtt cgaggtggag    1800
acctacgcca ccgtccacca gctcgtcagc acggtccgcg gccgcctggc ggccgacgtc    1860
tcccgccccc gcgcggtacg ggccgccttc cccggcgggt cgatgaccgg cgcgcccaag    1920
gtccgcacca tgcagttcat cgaccggctc gagaagggcc cgcgcggcgt gtactcgggc    1980
gcgctgggct acttcgccct cagcggcgcg ccgacctca gcatcgtcat ccgcaccatc     2040
gtcgccaccg aggaggccgc caccatcggc gtgggcggcg ccgtcgtcgc cctgtccgac    2100
cccgacgacg aggtccgcga aatgctcctc aaggcgcaga ccaccctcgc cgccctgcgc    2160
caggcacacg cgggcgccac cgcctcggac cgtgaactcc tggccggcag cctgcggtga    2220
```

<210> SEQ ID NO 15
<211> LENGTH: 719
<212> TYPE: PRT
<213> ORGANISM: Streptomyces pristinaespiralis

<400> SEQUENCE: 15

Val Arg Thr Val Arg Thr Leu Leu Ile Asp Asn Tyr Asp Ser Phe Thr
 1               5                  10                  15

Tyr Asn Leu Phe Gln Met Leu Ala Glu Val Asn Gly Ala Ala Pro Leu
             20                  25                  30

Val Val Arg Asn Asp Asp Thr Arg Thr Trp Gln Ala Leu Ala Pro Gly
         35                  40                  45

Asp Phe Asp Asn Val Val Ser Pro Gly Pro His Pro Ala Thr
     50                  55                  60

Asp Thr Asp Leu Gly Leu Ser Arg Arg Val Ile Thr Glu Trp Asp Leu
 65                  70                  75                  80

Pro Leu Leu Gly Val Cys Leu Gly His Gln Ala Leu Cys Leu Leu Ala
                 85                  90                  95

Gly Ala Ala Val Val His Ala Pro Glu Pro Phe His Gly Arg Thr Ser

-continued

```
                100                 105                 110
Asp Ile Arg His Asp Gly Gln Gly Leu Phe Ala Asn Ile Pro Ser Pro
            115                 120                 125

Leu Thr Val Val Arg Tyr His Ser Leu Thr Val Arg Gln Leu Pro Ala
130                 135                 140

Asp Leu Arg Ala Thr Ala His Thr Ala Asp Gly Gln Leu Met Ala Val
145                 150                 155                 160

Ala His Arg His Leu Pro Arg Phe Gly Val Gln Phe His Pro Glu Ser
                165                 170                 175

Ile Ser Ser Glu His Gly His Arg Met Leu Ala Asn Phe Arg Asp Leu
            180                 185                 190

Ser Leu Arg Ala Ala Gly His Arg Pro Pro His Thr Glu Arg Ile Pro
        195                 200                 205

Ala Pro Ala Pro Ala Pro Ala Pro Ala Pro Ala Pro Ala Pro Pro Ala
    210                 215                 220

Ser Ala Pro Val Gly Glu Tyr Arg Leu His Val Arg Glu Val Ala Cys
225                 230                 235                 240

Val Pro Asp Ala Asp Ala Ala Phe Thr Ala Leu Phe Ala Asp Ala Pro
                245                 250                 255

Ala Arg Phe Trp Leu Asp Ser Ser Arg Val Glu Pro Gly Leu Ala Arg
            260                 265                 270

Phe Thr Phe Leu Gly Ala Pro Ala Gly Pro Leu Gly Glu Gln Ile Thr
        275                 280                 285

Tyr Asp Val Ala Asp Arg Ala Val Arg Val Lys Asp Gly Ser Gly Gly
    290                 295                 300

Glu Thr Arg Arg Pro Gly Thr Leu Phe Asp His Leu Glu His Glu Leu
305                 310                 315                 320

Ala Ala Arg Ala Leu Pro Ala Thr Gly Leu Pro Phe Glu Phe Asn Leu
                325                 330                 335

Gly Tyr Val Gly Tyr Leu Gly Tyr Glu Thr Lys Ala Asp Ser Gly Gly
            340                 345                 350

Glu Asp Ala His Arg Gly Glu Leu Pro Asp Gly Ala Phe Met Phe Ala
        355                 360                 365

Asp Arg Met Leu Ala Leu Asp His Glu Gln Gly Arg Ala Trp Leu Leu
    370                 375                 380

Ala Leu Ser Ser Thr Arg Arg Pro Ala Thr Ala Pro Ala Ala Glu Arg
385                 390                 395                 400

Trp Leu Thr Asp Ala Ala Arg Thr Leu Ala Thr Thr Ala Pro Arg Pro
                405                 410                 415

Pro Phe Thr Leu Leu Pro Asp Asp Gln Leu Pro Ala Leu Asp Val His
            420                 425                 430

Tyr Arg His Ser Leu Pro Arg Tyr Arg Glu Leu Val Glu Glu Cys Arg
        435                 440                 445

Arg Leu Ile Thr Asp Gly Glu Thr Tyr Glu Val Cys Leu Thr Asn Met
    450                 455                 460

Leu Arg Val Pro Gly Arg Ile Asp Pro Leu Thr Ala Tyr Arg Ala Leu
465                 470                 475                 480

Arg Thr Val Ser Pro Ala Pro Tyr Ala Ala Tyr Leu Gln Phe Pro Gly
                485                 490                 495

Ala Thr Val Leu Ser Ser Pro Glu Arg Phe Leu Arg Ile Gly Ala
            500                 505                 510

Asp Gly Trp Ala Glu Ser Lys Pro Ile Lys Gly Thr Arg Pro Arg Gly
        515                 520                 525
```

```
Ala Gly Pro Ala Gln Asp Ala Val Lys Ala Ser Leu Ala Ala Ala
        530                 535                 540

Glu Lys Asp Arg Ser Glu Asn Leu Met Ile Val Asp Leu Val Arg Asn
545                 550                 555                 560

Asp Leu Gly Gln Val Cys Asp Ile Gly Ser Val His Val Pro Gly Leu
                565                 570                 575

Phe Glu Val Glu Thr Tyr Ala Thr Val His Gln Leu Val Ser Thr Val
            580                 585                 590

Arg Gly Arg Leu Ala Ala Asp Val Ser Arg Pro Arg Ala Val Arg Ala
        595                 600                 605

Ala Phe Pro Gly Gly Ser Met Thr Gly Ala Pro Lys Val Arg Thr Met
    610                 615                 620

Gln Phe Ile Asp Arg Leu Glu Lys Gly Pro Arg Gly Val Tyr Ser Gly
625                 630                 635                 640

Ala Leu Gly Tyr Phe Ala Leu Ser Gly Ala Ala Asp Leu Ser Ile Val
                645                 650                 655

Ile Arg Thr Ile Val Ala Thr Glu Glu Ala Ala Thr Ile Gly Val Gly
            660                 665                 670

Gly Ala Val Val Ala Leu Ser Asp Pro Asp Asp Glu Val Arg Glu Met
        675                 680                 685

Leu Leu Lys Ala Gln Thr Thr Leu Ala Ala Leu Arg Gln Ala His Ala
    690                 695                 700

Gly Ala Thr Ala Ser Asp Arg Glu Leu Leu Ala Gly Ser Leu Arg
705                 710                 715
```

<210> SEQ ID NO 16
<211> LENGTH: 962
<212> TYPE: DNA
<213> ORGANISM: Streptomyces pristinaespiralis

<400> SEQUENCE: 16

```
ctcgaggacg agtggatcgc ctccggcggc gccccgtcc  ccacgcccgt gcacgcgtcc    60
gcgtccgcgc gggggggccgt gctgtgaccg ccgccgcacc caccctcgcc caggcgctgg   120
acgaggccac cgggcagctg accggcgccg ggatcaccgc cgacgccgcc cgggccgaca   180
cccggctgct ggccgcccac gcctgccagg tcgccccggg ggacctcgac acctgcctgg   240
ccggcccggt gccgccccgg ttctggcact acgtccggcg ccgtctgacc cgcgaacccg   300
ccgaacgcat cgtcggccac gcctacttca tgggccaccg cttcgacctg gccccggcg   360
tcttcgtccc caaacccgag accgaggaga tcacccggga cgccatcgcc gcctggagg   420
ccctcgtccg ccgcggcacc accgcacccc tggtcgtcga cctgtgcgcc ggaccgggca   480
ccatggccgt caccctggcc cgccacgtac cggccgcccg cgtcctgggc atcgaactct   540
cccaggccgc cgcccgcgcc gccggcgca acgcccgcgg caccggcgcc cgcatcgtgc   600
agggcgacgc ccgcgacgcc ttccccgaac tgagcggcac cgtcgacctc gtcgtcacca   660
acccgcccta catcccatc ggactgcgca cctccgcacc cgaagtgctc gagcacgacc   720
```

```
cgccgctggc cctgtgggcc ggggaggagg gcctcggcat gatccgcgcc atggaacgca    780
ccgcggcccg gctgctggcc cccggcggcg tcctgctcct cgaacacggc tcctaccaac    840
tcgcctccgt gcccgccctg ttccgcgcaa ccggccgctg gagccacgcc tcgtcccgtc    900
ccacctgcaa cgacggctgc ctgaccgccg tacgcaacca cacctgcgca ccgccccgcct    960 ga                                                                   962
```

<210> SEQ ID NO 17
<211> LENGTH: 292
<212> TYPE: PRT
<213> ORGANISM: Streptomyces pristinaespiralis

<400> SEQUENCE: 17

```
Val Thr Ala Ala Pro Thr Leu Ala Gln Ala Leu Asp Glu Ala Thr
 1               5                  10                  15

Gly Gln Leu Thr Gly Ala Gly Ile Thr Ala Asp Ala Ala Arg Ala Asp
                20                  25                  30

Thr Arg Leu Leu Ala Ala His Ala Cys Gln Val Ala Pro Gly Asp Leu
         35                  40                  45

Asp Thr Cys Leu Ala Gly Pro Val Pro Pro Arg Phe Trp His Tyr Val
     50                  55                  60

Arg Arg Arg Leu Thr Arg Glu Pro Ala Glu Arg Ile Val Gly His Ala
 65                  70                  75                  80

Tyr Phe Met Gly His Arg Phe Asp Leu Ala Pro Gly Val Phe Val Pro
                 85                  90                  95

Lys Pro Glu Thr Glu Glu Ile Thr Arg Asp Ala Ile Ala Arg Leu Glu
                100                 105                 110

Ala Leu Val Arg Arg Gly Thr Thr Ala Pro Leu Val Val Asp Leu Cys
            115                 120                 125

Ala Gly Pro Gly Thr Met Ala Val Thr Leu Ala Arg His Val Pro Ala
        130                 135                 140

Ala Arg Val Leu Gly Ile Glu Leu Ser Gln Ala Ala Arg Ala Ala
145                 150                 155                 160

Arg Arg Asn Ala Arg Gly Thr Gly Ala Arg Ile Val Gln Gly Asp Ala
                165                 170                 175

Arg Asp Ala Phe Pro Glu Leu Ser Gly Thr Val Asp Leu Val Val Thr
            180                 185                 190

Asn Pro Pro Tyr Ile Pro Ile Gly Leu Arg Thr Ser Ala Pro Glu Val
        195                 200                 205

Leu Glu His Asp Pro Pro Leu Ala Leu Trp Ala Gly Glu Glu Gly Leu
    210                 215                 220

Gly Met Ile Arg Ala Met Glu Arg Thr Ala Ala Arg Leu Leu Ala Pro
225                 230                 235                 240

Gly Gly Val Leu Leu Leu Glu His Gly Ser Tyr Gln Leu Ala Ser Val
                245                 250                 255

Pro Ala Leu Phe Arg Ala Thr Gly Arg Trp Ser His Ala Ser Ser Arg
            260                 265                 270

Pro Thr Cys Asn Asp Gly Cys Leu Thr Ala Val Arg Asn His Thr Cys
        275                 280                 285

Ala Pro Pro Ala
        290
```